(12) United States Patent
Callan et al.

(10) Patent No.: US 11,878,059 B2
(45) Date of Patent: Jan. 23, 2024

(54) SONODYNAMIC THERAPY

(71) Applicant: UNIVERSITY OF ULSTER, Newtownabbey Antrim (GB)

(72) Inventors: John Callan, Newtownabbey Antrim (GB); Anthony Mchale, Newtownabbey Antrim (GB); Sukanta Kamila, Newtownabbey Antrim (GB); Keiran Logan, Newtownabbey Antrim (GB)

(73) Assignee: UNIVERSITY OF ULSTER, Newtownabbey Antrim (GB)

( * ) Notice: Subject to any disclaimer, the term of this patent is extended or adjusted under 35 U.S.C. 154(b) by 721 days.

(21) Appl. No.: 16/618,227

(22) PCT Filed: May 31, 2018

(86) PCT No.: PCT/GB2018/051481
§ 371 (c)(1),
(2) Date: Nov. 29, 2019

(87) PCT Pub. No.: WO2018/220376
PCT Pub. Date: Dec. 6, 2018

(65) Prior Publication Data
US 2020/0114003 A1    Apr. 16, 2020

(30) Foreign Application Priority Data
May 31, 2017  (GB) ..................................... 1708663

(51) Int. Cl.
| A61K 47/69 | (2017.01) |
| A61K 41/00 | (2020.01) |
| A61K 47/54 | (2017.01) |
| A61K 47/55 | (2017.01) |
| A61P 35/00 | (2006.01) |
| A61K 31/337 | (2006.01) |
| A61K 31/7048 | (2006.01) |
| A61K 31/7068 | (2006.01) |
| A61K 47/24 | (2006.01) |

(52) U.S. Cl.
CPC ........ *A61K 41/0033* (2013.01); *A61K 31/337* (2013.01); *A61K 31/7048* (2013.01); *A61K 31/7068* (2013.01); *A61K 41/0042* (2013.01); *A61K 47/24* (2013.01); *A61K 47/542* (2017.08); *A61K 47/549* (2017.08); *A61K 47/55* (2017.08); *A61K 47/557* (2017.08); *A61K 47/558* (2017.08); *A61K 47/6925* (2017.08); *A61P 35/00* (2018.01)

(58) Field of Classification Search
CPC .......................... A61K 47/6925; A61K 47/545
See application file for complete search history.

(56) References Cited

U.S. PATENT DOCUMENTS

| 6,498,945 B1 * | 12/2002 | Alfheim .................. A61P 35/00 424/9.1 |
| 2013/0189519 A1 | 7/2013 | Forrest et al. |
| 2018/0344872 A1 * | 12/2018 | Callan .................. A61K 47/557 |

FOREIGN PATENT DOCUMENTS

| CN | 102294035 | 12/2011 | |
| CN | 106267225 | 1/2017 | |
| EP | 3 120 872 | 1/2017 | |
| WO | 2007/038172 | 4/2007 | |
| WO | 2012/143739 | 10/2012 | |
| WO | WO-2012143739 A1 * | 10/2012 | ......... A61K 41/0033 |
| WO | 2015/089154 | 6/2015 | |
| WO | 2017/019520 | 2/2017 | |
| WO | 2017/089800 | 6/2017 | |

OTHER PUBLICATIONS

International Search Report and The Written Opinion of The International Searching Authority dated Aug. 27, 2018 in International (PCT) Application No. PCT/GB2018/051481.
International Preliminary Report on Patentability dated Dec. 12, 2019 in International (PCT) Application No. PCT/GB2018/051481.
United Kingdom Search Report dated Feb. 19, 2018 in United Kingdom Patent Application No. GB 1708663.8.
McEwan et al., "Combined sonodyarnic and antimetabolite therapy for the improved treatment of pancreatic cancer using oxygen loaded microbubbles as a delivery vehicle," Biomaterials, 2016, vol. 80, pp. 20-32.
McEwan et al., "Oxyen carrying microbubbles for enhanced sonodynamic hypoxic tumours," Journal of Controlled Release, 2016, vol. 203, pp. 51-56.
Maiti et al., "Gemcitabine-Coumarin-Biotin Conjugates: A Target Specific Theaostic Anticancer Prodrug," Journal of the American Chemical Society, 2013, vol. 135, pp. 4567-4572.
Bhuniya et al., "A fluorescence off-on reporter for real time monitoring of gemcitabine delivery to the cancer cells," Chem. Commun., 2013, vol. 49, pp. 7141-7143.
Rabideau et al., "Translocation of Non-Canonical Polypeptides into Cells Using Protective Antigen," Scientific Reports, 2015, vol. 5, pp. 1-11.
Allart et al., "A Stable Bis-Allyloxcarbonyl Biotin Aldehyde Derivative for Biotinylation via Reductive Alkylation: Application to the Synthesis of a Biotinylated Doxorubicin Derivative," Bioconjugate Chem., 2003, vol. 14, pp. 187-194.

(Continued)

Primary Examiner — Micah Paul Young
(74) Attorney, Agent, or Firm — Wenderoth, Lind & Ponack, L.L.P.

(57) ABSTRACT

The invention relates to microbubble complexes for use in methods of sonodynamic therapy which comprise a microbubble attached to or otherwise associated with one or more linking groups, each linking group being bound to at least one sonosensitising agent and at least one chemotherapeutic agent. It further relates to the microbubble complexes themselves and to pharmaceutical compositions which contain them. The invention is particularly suitable for the treatment of deep-sited tumors, in particular pancreatic cancer.

21 Claims, 12 Drawing Sheets

(56) References Cited

OTHER PUBLICATIONS

Kusayanagi et al., "The antitumor agent doxorubicin binds to Faconi anemia group F protein," Bioorganic & Medicinal Chemistry, 2012, vol. 20, pp. 6248-6255.
Koevary, Steven B., "Selective toxicity of rose bengal to ovarian cancer cells in vitro," Int. J. Physiol. Pathophysiol Pharmacol., 2012, vol. 4, pp. 99-107.
Oddo et al., "Next generation ultrasound platforms for theranostics," Journal of Collid and Interface Science, 2016, vol. 491, pp. 151-160.
Office Action dated Dec. 29, 2021 in corresponding Chinese Patent Application No. 201880050562.3.
Vutukuru, Srinavya et al., "An Affinity-Based Strategy for the Design of Selective Displacers for the Chromatographic Separation of Proteins", Langmuir, vol. 24, No. 13, 2008, pp. 6768-6773.

\* cited by examiner

SONODYNAMIC THERAPY

TECHNICAL FIELD

The present invention relates generally to improvements in and relating to methods of sonodynamic therapy and, more specifically, to such methods for the treatment of diseases characterised by hyperproliferative and/or abnormal cells.

More particularly, the invention relates to the targeted treatment of deeply-sited tumours, such as pancreatic cancer, using a combined sonodynamic and anti-cancer therapy.

BACKGROUND OF THE INVENTION

Conventional treatment of deeply-sited tumours typically involves major surgery, chemotherapy, radiotherapy or combinations of all of these. All three interventions may result in various complications including sepsis. Therefore, the development of more targeted and less invasive therapeutic approaches with improved efficacy to treat such patients is highly sought after. Pancreatic cancer is one example of a deeply-sited tumour. It remains one of the most lethal types of cancer known with less than 20% of those diagnosed being eligible for curative surgical treatment. It accounts for approximately 2% of all cancers with a five year survival of 15-21% in patients who have a surgical resection followed by systemic chemotherapy.

Methods known for use in the treatment of cancer include photodynamic therapy (PDT). PDT involves the application of photosensitising agents to the affected area, followed by exposure to photoactivating light to convert these into cytotoxic form. This results in the destruction of cells and surrounding vasculature in a target tissue. Photosensitisers which are currently approved for use in PDT absorb light in the visible region (below 700 nm). However, light of this wavelength has limited ability to penetrate the skin; this penetrates to a surface depth of only a few mm. Whilst PDT may be used to treat deeper sited target cells, this generally involves the use of a device, such as a catheter-directed fibre optic, for activation of the photosensitiser. Not only is this a complicated procedure, but it precludes access to certain areas of the body. It also compromises the non-invasive nature of the treatment. Thus, although appropriate for treating superficial tumours, the use of PDT in treating deeply seated cells, such as tumour masses, and anatomically less accessible lesions is limited.

Sonodynamic therapy (SDT) is a more recent concept and involves the combination of ultrasound and a sonosensitising drug (also referred to herein as a "sonosensitiser" or "sonosensitising agent"). In a manner similar to PDT, activation of the sonosensitiser by acoustic energy results in the generation of reactive oxygen species (ROS), such as singlet oxygen, at the target site of interest. Such species are cytotoxic, thereby killing the target cells or at least diminishing their proliferative potential. Many known photosensitising agents can be activated by acoustic energy and are thus suitable for use in SDT. Since ultrasound readily propagates through several cm of tissue, SDT provides a means by which tumours which are located deep within the tissues may be treated. As with light, ultrasound energy can also be focused on a tumour mass in order to activate the sonosensitiser thereby restricting its effects to the target site.

SDT offers some significant advantages over PDT: ultrasound is widely accepted as a cost effective and safe clinical imaging modality and, unlike light, can be tightly focused with penetration in soft tissue up to several tens of centimetres depending on the ultrasound frequency used.

In WO 2012/143739 sonosensitisers are conjugated to a gas-filled microbubble (MB) to provide a microbubble-sonosensitiser "complex" for use in SDT. These complexes permit effective delivery of the active sonosensitiser in a site-specific manner by a controlled destruction of the bubble using ultrasound. Subsequent or simultaneous sono-activation of the targeted sonosensitiser results in cell destruction at the target site and regression of tumour tissues.

Recently, the inventors have demonstrated the effectiveness of SDT using microbubble-sonosensitiser complexes for the treatment of pancreatic cancer in a pre-clinical model (McEwan et al. J Control Release. 2015; 203, 51-6). These studies have shown that an injection of ultrasound-responsive microbubbles (MB) filled with gaseous oxygen and bearing a Rose Bengal sensitiser provides a statistically significant SDT-mediated reduction in tumour growth in mice bearing human xenograft BxPC-3 tumours when compared to tumours treated with a similar MB conjugate comprising $SF_6$ as the core gas. The rationale for the incorporation of oxygen in the core of the MB was to enhance the amount of ROS generated in the tumour microenvironment during the sonodynamic event, as oxygen is a substrate for ROS production in SDT. Pancreatic tumours, in particular, are known to be highly hypoxic and this further negatively impacts the efficacy of approaches such as PDT/SDT that depend on oxygen for the generation of cytotoxic ROS.

It has also been demonstrated that combining the benchmark pancreatic cancer anti-metabolite therapeutics 5-fluorouracil (5-FU) and gemcitabine with complimentary chemotherapies such as irinotecan and oxaliplatin can improve the mean survival rate for pancreatic cancer sufferers (Lee et al., Chemotherapy. 2013; 59, 273-9). However, this combination, known as FOLFIRINOX, results in significant side-effects and is only indicated for patients who are otherwise fit and healthy.

A need thus exists for alternative methods for the treatment of deeply-sited, inaccessible tumours, such as pancreatic cancer, in particular methods which are non-invasive or minimally invasive and which are without adverse side-effects. Such methods would have obvious socio-economic benefits, e.g. in terms of reduced patient trauma, reduced treatment expense and reduced costs associated with any hospital stay. The present invention addresses this need.

SUMMARY OF THE INVENTION

The inventors now propose that as anti-metabolite therapy and SDT exert their cytotoxic effects via different mechanisms (the former through thymidylate synthase inhibition and the latter through oxidation of cellular substrates) their combination in a single therapeutic regime may provide significant patient benefit.

Specifically, the inventors have now found that the use of a microbubble to simultaneously deliver both a sonosensitiser and an anti-metabolite confers a number of advantages when used in methods of sonodynamic therapy. Specifically, what they have found is that the delivery of both a sonosensitiser and an anti-metabolite in the form of a complex with a microbubble (a "microbubble complex") permits effective delivery of both agents in a site-specific manner (e.g. to an internal tumour) by a controlled destruction of the bubbles using ultrasound. Sono-activation of the targeted sonosensitiser results in the generation of ROS which destroy tumour cells at the target site. This action is complimented by the action of the anti-metabolite which exerts its cytotoxic effect directly at the intended target site. By using a microbubble as a carrier for both agents, non-specific uptake of these by non-target tissues is reduced, thus providing a significant advantage over systemic delivery. This therapy is thus expected to reduce side-effects and, in turn, provide significant patient benefit.

As described herein, the inventors propose the use of a ligand (herein referred to as a "linking group") which enables the attachment of both a sonosensitiser and an anti-metabolite to the surface of a single microbubble (e.g. via the "biotin-avidin" interaction). This enables combined anti-metabolite/SDT treatment using a single microbubble. By attaching both agents to the same microbubble rather than to separate microbubbles, an increase in drug loading can be achieved. The ligand may also be modified to carry two or more anti-metabolites and/or two or more sonosensitisers to further enhance drug loading.

The microbubble complexes herein described are particularly suitable for the treatment of pancreatic cancer. However, their use extends to the treatment of other diseases and conditions characterised by hyperproliferative and/or abnormal cells, in particular to the treatment of other deeply-sited tumours. As will be described herein, these therefore have broader application which extends to the treatment of other such diseases and conditions using various chemotherapeutic drugs.

By further modifying the microbubble complex to incorporate a chemotherapeutic drug within its shell structure the inventors also propose that a highly targeted anti-cancer therapy can be realised having enhanced therapeutic effects.

DETAILED DESCRIPTION OF THE INVENTION

In one aspect the invention provides a microbubble complex which comprises a microbubble attached to or otherwise associated with one or more linking groups, each linking group being bound to at least one sonosensitising agent and at least one chemotherapeutic agent.

In another aspect the invention provides a microbubble complex which comprises a microbubble attached to or otherwise associated with one or more linking groups, each linking group being bound to at least one sonosensitising agent and at least one chemotherapeutic agent (a "first chemotherapeutic agent"), wherein said microbubble comprises a shell having incorporated therein one or more additional chemotherapeutic agents (a "second chemotherapeutic agent"). In this aspect of the invention the first and second chemotherapeutic agents may be different or they may be identical. Preferably, they will be different.

In a further aspect the invention provides a microbubble complex as herein described for use in a method of sonodynamic therapy.

In a yet further aspect the invention provides a method of sonodynamic therapy in which a microbubble complex as herein described is administered to affected cells or tissues of a patient, and said cells or tissues are subjected to ultrasound irradiation.

To the extent that the microbubble complexes according to the invention are intended for use in methods of SDT, it will be understood that they will be ultrasound-responsive. Specifically, it is intended that the microbubble component of the complexes can be ruptured by application of ultrasound, thereby releasing the sonosensitising agent(s) and chemotherapeutic agent(s) at the desired target site.

As used herein, the term "microbubble" is intended to refer to a microsphere comprising a shell having an approximately spherical shape and which surrounds an internal void which comprises a gas or mixture of gases. The "shell" refers to the membrane which surrounds the internal void of the microbubble.

The terms "sonosensitiser", "sonosensitising agent" and "sonosensitising drug" are used interchangeably herein and are intended to refer to any compound which is capable of converting acoustic energy (e.g. ultrasound) into reactive oxygen species (ROS), such as singlet oxygen, that results in cell toxicity.

As used herein, the term "chemotherapeutic agent" is intended to broadly encompass any chemical or biological compound useful in the treatment of cancer. It includes growth inhibitory agents and other cytotoxic agents. The term "growth inhibitory agent" refers to a compound which inhibits growth of a cell, especially a cancer cell either in vitro or in vivo.

As used herein, the term "sonodynamic therapy" is intended to refer to a method involving the combination of ultrasound and a sonosensitising agent in which activation of the sonosensitising agent by acoustic energy results in the generation of reactive oxygen species, such as singlet oxygen.

The microbubble complexes according to the invention comprise a microbubble attached to or otherwise associated with at least one sonosensitising agent and at least one chemotherapeutic agent. These agents are attached to or otherwise associated with the microbubble via one or more linking groups which each carry at least one sonosensitising agent and at least one chemotherapeutic agent. As will be understood, the sonosensitising agent and chemotherapeutic agent carried by any given linking group will not be the same chemical entity, i.e. these will be different chemical entities.

In one embodiment the microbubble complexes according to the invention comprise a microbubble attached to or otherwise associated with a plurality of sonosensitising agents and/or a plurality of chemotherapeutic agents.

Where the microbubble is bound to more than one sonosensitising agent, these may be the same or different, and may be carried by a single linking group or two or more linking groups. Generally, the sonosensitising agents bound to a particular microbubble will be identical.

Where the microbubble is bound to more than one chemotherapeutic agent, these may be the same or different, and may be carried by a single linking group or two or more linking groups. Generally, the chemotherapeutic agents attached to a particular microbubble via a linking group (or groups) as herein described will be identical.

The chemotherapeutic agent(s) and sonosensitising agent(s) are linked to the microbubble via one or more linking groups. Each linking group may be bound to or otherwise associated with the microbubble and the chemotherapeutic agent(s) and sonosensitising agent(s) through covalent or non-covalent means, e.g. via electrostatic interaction, hydrophobic interactions, van der Waals forces, hydrogen bonding, or any combination thereof.

In one embodiment the interaction between the linking group(s) and the microbubble may involve strong non-covalent bonding such as the biotin-avidin interaction. In this embodiment one component of the binding pair (e.g. the linking group) is functionalised with biotin and the other (e.g. the microbubble) with avidin. Since avidin contains multiple binding sites for biotin, this will typically also be bound to the microbubble via a biotin-avidin interaction. For example, a microbubble may be functionalised with biotin to form a biotinylated microbubble which is then incubated with avidin. Once the avidin is bound to the microbubble, this permits binding of any further biotinylated moieties, such as a linking group which incorporates biotin (or a biotin residue). The resulting linkage between the microbubble and the linking group may thus take the form of a "biotin-avidin-biotin" interaction.

In one embodiment, the chemotherapeutic agent(s) and/or sonosensitising agent(s) are covalently bound to the linking group(s), i.e. the chemotherapeutic agent(s) and/or sonosensitising agent(s) are attached to the linking group(s) via one or more covalent bonds.

As will be understood, the precise nature of the linking group(s) for use in the invention is not critical provided these are capable of linking at least one chemotherapeutic agent and at least one sonosensitising agent to the microbubble (or to a suitably 'functionalised' microbubble as herein described, e.g. a microbubble which carries one or more biotin-avidin functionalities). As will be appreciated, any linking group should be biocompatible.

Any of the microbubbles herein described may be bound to or otherwise associated with a plurality of linking groups in order to further increase the loading of sonosensitising and chemotherapeutic agents. In this embodiment, the linking groups need not be identical to one another although generally they will be the same.

Suitable linking groups may readily be selected by those skilled in the art. Typically each linking group will comprise an organic group comprising a chain of up to about 200 atoms, e.g. up to about 100 atoms, between its points of attachment to the microbubble (or 'functionalised' microbubble) and to the chemotherapeutic agent and sonosensitising agent. The organic chain may comprise aliphatic, alicyclic, or aromatic groups, or any combination thereof. In one embodiment, it may comprise aliphatic, alicyclic and aromatic groups. In another embodiment, it may comprise aliphatic and alicyclic groups.

Suitable linking groups may have a molecular weight of up to about 3,000 Da, e.g. up to about 1,500 Da.

Linking groups for use in the invention may be linear or branched. In one embodiment the linking group may be branched. Various degrees of branching may be provided and can be selected depending on the number of agents to be carried by the linking group. For example, the linking group may comprise up to six branches, e.g. one, two, three or four branches, which enable its attachment to the microbubble (or 'functionalised' microbubble), and to the chemotherapeutic agent(s) and sonosensitising agent(s). Attachment of the linking group to the microbubble and to the chemotherapeutic and sonosensitising agents will generally be via terminal groups of the branched structure.

In one embodiment the linking group may comprise three branches, i.e. it is "tri-podal". In this embodiment, a first branch of the linking group will be capable of binding to the microbubble (e.g. via a non-covalent interaction such as "avidin-biotin"), a second branch will be capable of linking to the chemotherapeutic agent (e.g. covalently), and a third branch will be capable of linking to the sonosensitising agent (e.g. covalently).

Suitable linking groups may comprise a straight-chained or branched (preferably branched) $C_{30-50}$ alkylene chain (preferably a $C_{30-40}$ alkylene chain) optionally substituted by one or more groups selected from $C_{1-3}$ alkyl, —O($C_{1-3}$) alkyl, and —OR' (where R' is H or $C_{1-6}$ alkyl, preferably $C_{1-3}$ alkyl, e.g. methyl); and in which one or more (preferably up to 10, e.g. from 4 to 9, or from 6 to 8) —$CH_2$— groups of the alkylene chain may be replaced by a group independently selected from —O—, —CO—, —C(O)O—, —NR"— and —NR"CO— (where each R" is independently H or $C_{1-6}$ alkyl, preferably $C_{1-3}$ alkyl, e.g. methyl). In one embodiment the linking group may also be substituted (e.g. terminally substituted) by biotin or a biotin residue as herein described.

In one embodiment, the linking group may comprise one or more amino acids. For example, it may comprise a peptide, a peptide residue or fragment.

Tri-podal linking groups suitable for use in the invention include those in which the branches are linked to a central N or C atom. Those having a central nitrogen atom are preferred for use in the invention. Such linking groups include those having the following structure:

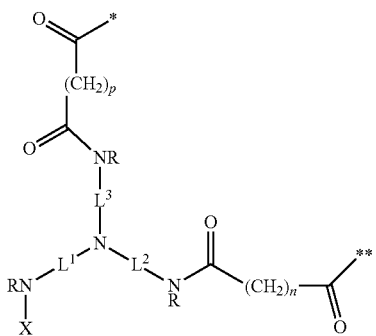

wherein:
$L^1$, $L^2$ and $L^3$ are each independently —$(CH_2)_q$— in which q is an integer from 1 to 4, preferably 2;
each R is independently either H or $C_{1-6}$ alkyl (preferably $C_{1-3}$ alkyl, e.g. $CH_3$), preferably H;
n is an integer from 2 to 10, preferably 4 to 8, more preferably 5 to 7, e.g. 6;
p is an integer from 2 to 10, preferably 4 to 8, more preferably 5 to 7, e.g. 6;
X is a functional group capable of binding to a microbubble or to a 'functionalised' microbubble as herein described;
* denotes the point of attachment of the linking group to a sonosensitising agent, a 'functionalised' sonosensitising agent, or a residue of a sonosensitising agent as herein described; and
* denotes the point of attachment of the linking group to a chemotherapeutic agent, a 'functionalised' chemotherapeutic agent, or a residue of a chemotherapeutic agent as herein described.

As will be understood, linkage of the various components to form the microbubble complexes according to the invention may, in some cases, require that one or more of the components are suitably "functionalised", for example by incorporation of one or more reactive groups which enable their linkage or association with one another (e.g. by the formation of a covalent bond, or any other type of bonding herein described). Any reference herein to a "functionalised" component of the complexes should be construed accordingly. For example, a "functionalised" microbubble may carry a 'biotin-avidin' functional group in order that it may bind to a biotinylated linking group. "Functionalised" sonosensitising agents and "functionalised" chemotherapeutic agents may, for example, carry one or more reactive groups (such as amine, e.g. primary amine, carboxyl, hydroxyl, acid, acid halide, thiol, carbonyl, etc.) which enable their linkage to the chosen linking group. Any suitable functional groups may be used and these may readily be selected by those skilled in the art depending on the nature of the components to be linked to one another.

"Functionalisation" of any component (e.g. the sonosensitising agent or the chemotherapeutic agent) will typically involve reaction with one or more compounds which are capable of providing the desired "functionalised" component. Suitable compounds may readily be determined by any skilled chemist and may include, for example, moieties containing an amine or carboxylic acid group. Following reaction with the agent these may, for example, provide a terminal amine or carboxylic acid functionality which is capable of reaction with the chosen linking group. Examples of compounds which may be used for functionalisation of a sonosensisting agent or a chemotherapeutic agent are illustrated herein in Schemes 2 and 4. In Scheme 2, Br—CH$_2$—CH$_2$—NH$_2$ is used to functionalise the sonosensitising agent Rose Bengal to produce "Rose Bengal-amine". In Scheme 4, Rose Bengal is reacted with 8-bromooctanoic acid to produce "Rose Bengal-octanoic acid", and the chemotherapeutic agent gemcitabine is reacted with HO—(CH$_2$)$_{11}$—CO$_2$H and 4-nitrophenyl chloroformate to produce a carboxylic acid functionalised gemcitabine.

Similarly, it will be understood that following linkage of the various components (e.g. via a chemical reaction) to form the microbubble complexes according to the invention, some or all of the components may no longer retain their original structure but may "lose" one or more terminal groups or atoms (e.g. a H atom) as a result of the reaction involved in their linkage or association with one another (e.g. by the formation of a covalent bond, or any other type of bonding herein described). These components may be considered a "residue" of the original component and any reference to a "residue" of a component of the complexes should be construed accordingly. Schemes 2 and 4 are provided herein as examples of methods which may be used in the preparation of a tri-podal linking group incorporating biotin. In these examples, the terminal carboxyl group of biotin is used to link it to the tri-podal linking group, typically via an amine or ester bond. In the final structure the biotin is present as a "residue" of biotin.

In formula (I), L$^1$, L$^2$ and L$^3$ may be identical. In one embodiment, L$^1$, L$^2$ and L$^3$ are each —(CH$_2$)$_2$—.

In formula (I), each R may be identical. In one embodiment, each R is H.

In formula (I), n and p may be identical. In one embodiment, n and p are both an integer from 4 to 8, e.g. 6.

In one embodiment of formula (I), X is biotin or a biotin residue which is capable of binding to an avidin-functionalised microbubble.

An example of a tri-podal linking group within general formula (I) for use in the invention is as follows:

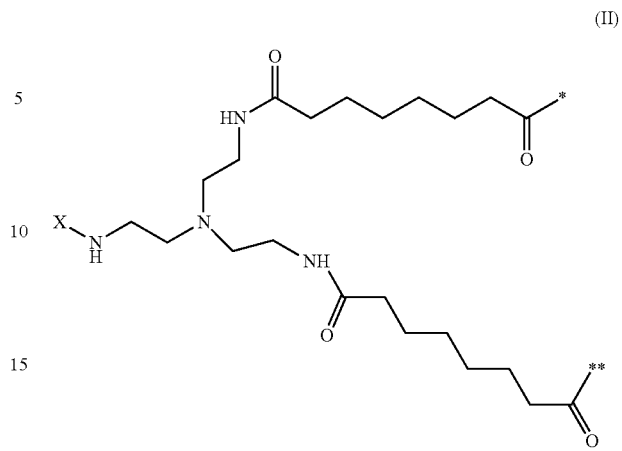

(II)

wherein:
X is a functional group capable of binding to a microbubble or to a 'functionalised' microbubble as herein described;
* denotes the point of attachment of the linking group to a sonosensitising agent, a 'functionalised' sonosensitising agent, or a residue of a sonosensitising agent as herein described; and
** denotes the point of attachment of the linking group to a chemotherapeutic agent, a 'functionalised' chemotherapeutic agent, or a residue of a chemotherapeutic agent as herein described.

In one embodiment of formula (II), X is biotin or a biotin residue which is capable of binding to an avidin-functionalised microbubble.

Other tri-podal linking groups which may be used in the invention are those having the following general structure:

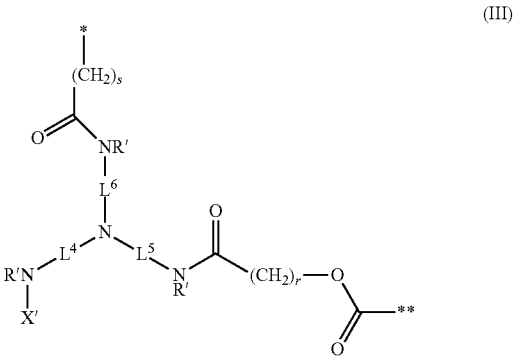

(III)

wherein:
L$^4$, L$^5$ and L$^6$ are each independently —(CH$_2$)$_t$— in which t is an integer from 1 to 4, preferably 2;
each R' is independently either H or C$_{1-6}$ alkyl (preferably C$_{1-3}$ alkyl, e.g. CH$_3$), preferably H;
r is an integer from 2 to 10, preferably 4 to 8, more preferably 5 to 7, e.g. 6;
s is an integer from 2 to 10, preferably 4 to 8, more preferably 5 to 7, e.g. 6 or 7;
X' is a functional group capable of binding to a microbubble or to a 'functionalised' microbubble as herein described;

* denotes the point of attachment of the linking group to a sonosensitising agent, a 'functionalised' sonosensitising agent, or a residue of a sonosensitising agent as herein described; and
* denotes the point of attachment of the linking group to a chemotherapeutic agent, a 'functionalised' chemotherapeutic agent, or a residue of a chemotherapeutic agent as herein described.

In an alternative embodiment of formula (III):
* denotes the point of attachment of the linking group to a chemotherapeutic agent, a 'functionalised' chemotherapeutic agent, or a residue of a chemotherapeutic agent as herein described; and
*denotes the point of attachment of the linking group to a sonosensitising agent, a 'functionalised' sonosensitising agent, or a residue of a sonosensitising agent as herein described.

In formula (III), $L^4$, $L^5$ and $L^6$ may be identical. In one embodiment, $L^4$, $L^5$ and $L^6$ are each —$(CH_2)_2$—.

In formula (III), each R' may be identical. In one embodiment, each R' is H.

In formula (III), r and s may be identical or different. In one embodiment, r and s are both an integer from 4 to 8, e.g. 6 or 7. In one embodiment r is 6 and s is 7.

In one embodiment of formula (III), X' is biotin or a biotin residue which is capable of binding to an avidin-functionalised microbubble.

An example of a tri-podal linking group according to formula (III) which may be used in the invention is as follows:

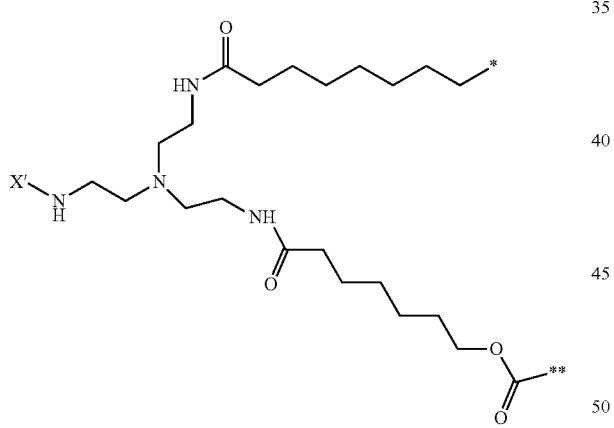

(IV)

wherein:
X' is a functional group capable of binding to a microbubble or to a 'functionalised' microbubble as herein described;
* denotes the point of attachment of the linking group to a sonosensitising agent, a 'functionalised' sonosensitising agent, or a residue of a sonosensitising agent as herein described; and
* denotes the point of attachment of the linking group to a chemotherapeutic agent, a 'functionalised' chemotherapeutic agent, or a residue of a chemotherapeutic agent as herein described.

In one embodiment of formula (IV), X' is biotin or a biotin residue which is capable of binding to an avidin-functionalised microbubble.

Other tri-podal linking groups which may be used in the invention are those having the following general structure:

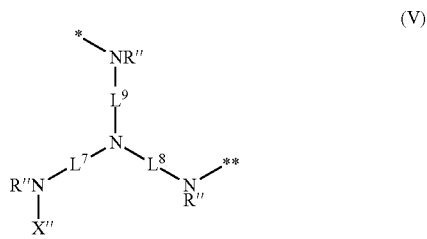

(V)

wherein:
$L^7$, $L^8$ and $L^9$ are each independently —$(CH_2)_u$— in which u is an integer from 1 to 4, preferably 2;
each R" is independently either H or $C_{1-6}$ alkyl (preferably $C_{1-3}$ alkyl, e.g. $CH_3$), preferably H;
X" is a functional group capable of binding to a microbubble or to a 'functionalised' microbubble as herein described;
* denotes the point of attachment of the linking group to a sonosensitising agent, a 'functionalised' sonosensitising agent, or a residue of a sonosensitising agent as herein described; and
* denotes the point of attachment of the linking group to a chemotherapeutic agent, a 'functionalised' chemotherapeutic agent, or a residue of a chemotherapeutic agent as herein described.

In formula (V), $L^7$, $L^8$ and $L^9$ may be identical. In one embodiment, $L^7$, $L^8$ and $L^9$ are each —$(CH_2)_2$—.

In formula (V), each R" may be identical. In one embodiment, each R" is H.

In one embodiment of formula (V), X" is biotin or a biotin residue which is capable of binding to an avidin-functionalised microbubble.

An example of a tri-podal linking group according to formula (V) which may be used in the invention is as follows:

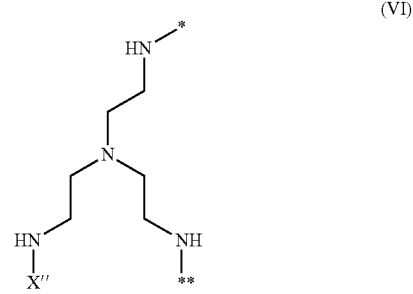

(VI)

wherein:
X" is a functional group capable of binding to a microbubble or to a 'functionalised' microbubble as herein described;
* denotes the point of attachment of the linking group to a sonosensitising agent, a 'functionalised' sonosensitising agent, or a residue of a sonosensitising agent as herein described; and
* denotes the point of attachment of the linking group to a chemotherapeutic agent, a 'functionalised' chemotherapeutic agent, or a residue of a chemotherapeutic agent as herein described.

For use in the invention, suitable classes of chemotherapeutic agents and examples within those classes include the following: antifolates (e.g. methotrexate); 5-fluoropyrimidines (e.g. 5-fluorouracil or 5-FU); cytidine analogues (e.g. gemcitabine); purine antimetabolites (e.g. mercaptopurine); alkylating agents (e.g. cyclophosphamide); non-classical alkylating agents (e.g. dacarbazine); platinum analogues (e.g. cisplatin); antitumour antibiotics (e.g. actinomycin D, bleomycin, mitomycin C); bioreductive drugs (e.g. mitomycin C, Banoxantrone (AQ4N)); anthracyclines (e.g. doxorubicin, mitoxantrone); topoisomerase I inhibitors (e.g. irinotecan); topoisomease II inhibitors (e.g. etoposide); antimicrotubule agents such as vinca alkaloids (e.g. vincristine), taxols (e.g. paclitaxel), and epothilones (e.g. ixabepiline); antioestrogens (e.g. tamoxifen); antiandrogens (e.g. biclutamide, cyproterone acetate); aromatase inhibitors (e.g. anastrazole, formestan); antiangiogenic or hypoxia targeting drugs (either naturally occuring, e.g. endostatin, or synthetic, e.g. gefitinib, lenalidomide); antivascular agents (e.g. cambretastatin); tyrosine kinase inhibitors (e.g. gefitinib, erlotinib, vandetanim, sunitinib); oncogene or signalling pathway targeting agents (e.g. tipfarnib, lonafarnib, naltrindole, rampamycin); agents targeting stress proteins (e.g. geldanamycin and analogues thereof); autophagy targeting agents (e.g. chloroquine); proteasome targeting agents (e.g. bortezomib); telomerase inhibitors (targeted oligonucleotides or nucleotides); histone deacetylase inhibitors (e.g. trichostatin A, valproic acid); DNA methyl transferase inhibitors (e.g. decitabine); alkyl sulfonates (e.g. busulfan, improsulfan and piposulfan); aziridines (e.g. benzodopa, carboquone, meturedopa, and uredopa); ethylenimines and methylamelamines (e.g. altretamine, triethylenemelamine, trietylenephosphoramide, triethylenethiophosphaoramide and trimethylolomelamine); nitrogen mustards (e.g. chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard); nitrosureas (e.g. carmustine, chlorozotocin, fotemustine, lomustine, nimustine, ranimustine); purine analogues (e.g. fludarabine, 6-mercaptopurine, thiamiprine, thioguanine); pyrimidine analogues (e.g. ancitabine, azacitidine, 6-azauridine, carmofur, cytarabine, dideoxyuridine, doxifluridine, enocitabine, floxuridine); androgens (e.g. calusterone, dromostanolone propionate, epitiostanol, mepitiostane, testolactone); anti-adrenals (e.g. aminoglutethimide, mitotane, trilostane); and immune checkpoint inhibitors (e.g. BMS-1001 and BMS-1166). Pharmaceutically acceptable salts, derivatives or analogues of any of these compounds may also be used.

Examples of growth inhibitory agents for use in the invention include agents that block cell cycle progression (at a place other than S phase), such as agents that induce G1 arrest and M-phase arrest. Classical M-phase blockers include the vincas (vincristine and vinblastine); taxane family members, including paclitaxel, docetaxel, and analogues thereof; and topoisomerase inhibitors, such as irinotecan, topotecan, camptothecin, lamellarin D, doxorubicin, epirubicin, daunorubicin, etoposide, and bleomycin. Those agents that arrest G1 include, for example, DNA alkylating agents, such as tamoxifen, prednisone, dacarbazine, mechlorethamine, cisplatin, methotrexate, 5-FU, and ara-C.

The choice of chemotherapeutic agent will be dependent on various factors including the nature of the tumour, the patient to be treated, etc., but can readily be selected by those skilled in the art.

In one particular embodiment the chemotherapeutic agent is an anti-metabolite. Anti-metabolites which are particularly suitable for use in the invention include the 5-fluoropyrimidines, and cytidine analogues. Examples of anti-metabolites which may be used in the treatment of pancreatic cancer are 5-fluorouracil (5-FU) and gemcitabine. Such agents find particular use in the invention and in one embodiment these may be carried by any of the linking groups herein described.

In one embodiment the chemotherapeutic agent is a growth inhibitory agent. Those which are particularly suitable for use in the invention include the anthracycline topoisomerase inhibitors, e.g. doxorubicin.

For incorporation within the shell structure of the microbubble, any of the chemotherapeutic agents herein described may be chosen. The chemotherapeutic agent should be one capable of spontaneously embedding within the hydrophobic lipid chains of the microbubble lipids. This may involve direct hydrophobic interaction in cases where the chemotherapeutic is hydrophobic. In one embodiment, the chemotherapeutic agent for incorporation within the shell of the microbubble may therefore be hydrophobic. Hydrophobic agents may be considered to be those having a LogP value greater than about 2. Alternatively, non-polar chemotherapeutic agents may be suitably modified (e.g. functionalised) by the introduction or one or more non-polar functional groups which enable them to spontaneously embed within the shell (e.g. the lipid shell) of the microbubble.

In one embodiment, the chemotherapeutic agent to be incorporated within the shell of the microbubble may be an anti-microtubule agent. Examples of such agents include, in particular, taxols such as paclitaxel. Paclitaxel (or "PTX") is hydrophobic.

In one embodiment, an immune checkpoint inhibitor (e.g. BMS-1001 or BMS-1166) may be included within the shell of the microbubble in order to stimulate the immune system during therapy.

Microbubbles are well known in the art, for example as ultrasound contrast agents. Their composition and methods for their preparation are thus well known to those skilled in the art. Examples of procedures for the preparation of microbubbles are described in, for example, Christiansen et al., Ultrasound Med. Biol., 29: 1759-1767, 2003; Farook et al., J. R. Soc. Interface, 6: 271-277, 2009; and Stride & Edirisinghe, Med. Biol. Eng. Comput., 47: 883-892, 2009, the contents of which are hereby incorporated by reference.

Microbubbles comprise a shell which surrounds an internal void comprising a gas. Generally, these are approximately spherical in shape, although the shape of the microbubble is not essential in carrying out the invention and is therefore not to be considered limiting. The size of the microbubble should be such as to permit its passage through systemic circulation (e.g. the pulmonary system) following administration, e.g. by intravenous injection. Microbubbles typically have a diameter of less than about 200 µm, preferably in the range from about 0.1 to about 100 µm, e.g. from about 0.5 to about 100 µm. Particularly suitable for use in the invention are microbubbles having a diameter of less than about 10 µm, more preferably 1 to 8 µm, particularly preferably up to 5 µm, e.g. about 2 µm. The shell of the microbubble will vary in thickness and will typically range from about 5 to about 200 nm, e.g. from about 10 to about 200 nm. The precise thickness is not essential provided that the shell performs the desired function of retaining the gas core.

Materials which may be used to form the microbubbles should be biocompatible and suitable materials are well known in the art. Typically, the shell of the microbubble will comprise a surfactant or a polymer. Surfactants which may be used include any material which is capable of forming and maintaining a microbubble by forming a layer at the interface between the gas within the core and an external medium, e.g. an aqueous solution which contains the microbubble. A surfactant or combination of surfactants may be used. Those which are suitable include lipids, in particular phospholipids. Lipids which may be used include lecithins (i.e. phosphatidylcholines), e.g. natural lecithins such as egg yolk lecithin or soya bean lecithin and synthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; and mixtures thereof. In one embodiment, lipids such as 1,2-dibehenoyl-sn-glycero-3-phosphocholine (DBPC) and/or 1,2-distearoyl-sn-glycero-3-phosphoethanolamine (DSPE) may be used to form the shell of the microbubbles. Combinations of DBPC and DSPE are particularly suitable for use in the invention.

Suitable lipids and combinations of lipids may be selected based on their ability to enhance the stability of the microbubbles with regard to oxygen retention. Suitable for use in this regard is 1,2-dibehenoyl-sn-glycero-3-phosphocholine (DBPC). In one embodiment, a combination of lipids may be used in which DBPC is present in an amount of at least 70, preferably at least 80, more preferably at least 80 mol. % (based on the total amount of lipid).

Polymer materials which are suitable for use in forming the shell of the microbubble include proteins, in particular albumin, particularly human serum albumin. Other biocompatible polymers which may be used include poly(vinyl alcohol) (PVA), poly(D,L-lactide-co-glycolide) (PLGA), cyanoacrylate, poloxamers (Pluronics), chitosan and chitosan derivatives, or combinations thereof.

The microbubble shells may comprise single or multiple layers of the same or different materials. Multiple layers may, for example, be formed in cases where the basic shell material (e.g. a lipid) bears one or more polymers or polysaccharides. Examples of such polymers include polyethylene glycol (PEG) and polyvinylpyrrolidone. The microbubble shell may also be coated with polymers, such as poly-L-lysine and PLGA, and/or polysaccharides, such as alginate, dextran, diethylamino-ethyl-dextran hydrochloride (DEAE) or chitosan. Methods for attaching these coating materials may involve electrostatic or covalent interactions. Different coating materials (polymers, polysaccharides, proteins, etc.) may be used in order to improve the properties of the microbubble, for example by increasing the rigidity, stability in circulation and/or tissue permeation capability of the microbubble-based reagents, by manipulating the net surface charge of the microbubble and, perhaps most importantly, by increasing its payload capacity.

Lipids forming either a monolayer, bilayer or multilamellar structure may be used to form the microbubbles for use in the invention. Examples of these include unilamellar or multilammellar liposomes and micelles.

Any of the microbubble shells herein described may comprise further components which aid in accumulation of the microbubbles at the target site. For example, these may be functionalised such that these incorporate or have bound thereto a ligand or targeting agent which is able to bind to a target cell or tissue. Examples of suitable targeting agents include antibodies and antibody fragments, cell adhesion molecules and their receptors, cytokines, growth factors and receptor ligands. Such agents can be attached to the microbubbles using methods known in the art, e.g. by covalent coupling, the use of molecular spacers (e.g. PEG) and/or the avidin-biotin complex method. For example, the incorporation of a lipid-PEG-biotin conjugate in lipid-based microbubbles followed by the addition of avidin enables functionalisation of the microbubble surface with a biotinylated targeting ligand. Herceptin is an example of an antibody which may be conjugated to the microbubble shell for targeting purposes.

The microbubble shell may further comprise components which aid in its attachment to one or more linking groups as herein described. In one embodiment, the microbubble shell may be covalently coupled to biotin or a biotin residue via a molecular spacer, such as PEG (e.g. PEG-2000). This enables functionalisation of the surface of the microbubble with avidin which may then be conjugated to a biotinylated linking group. Incorporation of a lipid-spacer-biotin conjugate (e.g. a lipid-PEG-biotin conjugate) in the shell of the microbubble may be achieved by appropriate functionalisation of one or more lipids prior to formation of the microbubble.

In the case where a chemotherapeutic agent (e.g. paclitaxel, PTX) is incorporated within the shell of the microbubble this may, for example, be dissolved in an organic solvent and added to a solution containing the lipids prior to formation of the microbubble. Evaporation of the solvent provides a dried lipid film incorporating the chemotherapeutic agent (e.g. PTX) which may be reconstituted and sonicated to provide the loaded microbubble. The lipid-chemotherapeutic agent film (e.g. lipid-PTX film) may be reconstituted in a suitable solvent, heated above the lipid transition temperature and gently sonicated to ensure full incorporation of the chemotherapeutic agent into the lipid chains. The solution may then be sparged with a suitable gas (e.g. perfluorobutane, PFB) while sonicating to prepare the final microbubble suspension.

Where the shell comprises polymer materials, such as albumin, a chemotherapeutic agent (e.g. paclitaxel) may be incorporated (e.g. embedded) within the shell of the microbubble using a double emulsion (e.g. water-in-oil-in-water) method. Using this method, the chemotherapeutic agent may be dissolved in the oil phase of the emulsion along with the polymer. Following removal of a solvent from the emulsion, the oil phase becomes a polymer shell having the chemotherapeutic agent embedded therein.

The gas within the core of the microbubble should be biocompatible. The term "gas" encompasses not only substances which are gaseous at ambient temperature and pressure, but also those which are in liquid form under these conditions. Where the "gas" is liquid at ambient temperature this will generally undergo a phase change to a gas or vapour at a temperature of 38° C. or above. For any gas which is a liquid at ambient temperature, it is generally preferred that this will undergo a phase change to a gas at a temperature between about 38 and 45° C., preferably slightly above body temperature. For example, it may undergo a phase change when subjected to a stimulus, such as ultrasound, which causes a local increase in temperature. Any reference herein to "gas" should thus be considered to encompass not only gases and liquids, but also liquid vapours and any combination thereof, e.g. a mixture of a liquid vapour in a gas.

Gases which are suitable for incorporation within the microbubbles for use according to the invention include air, nitrogen, oxygen, carbon dioxide, hydrogen; inert gases such as helium, argon, xenon or krypton; sulphur fluorides such as sulphur hexafluoride, disulphur decafluoride; low molecular weight hydrocarbons such as alkanes (e.g. methane, ethane, propane, butane), cycloalkanes (e.g. cyclopropane, cyclobutane, cyclopentane), alkenes (e.g. ethylene, propene); and alkynes (e.g. acetylene or propyne); ethers; esters; halogenated low molecular weight hydrocarbons; and mixtures thereof.

Examples of suitable halogenated hydrocarbons are those which contain one or more fluorine atoms and include, for example, bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethyl fluoride, 1,1-difluoroethane and perfluorocarbons.

Examples of suitable fluorocarbon compounds include perfluorocarbons. Perfluorocarbons include perfluoroalkanes such as perfluoromethane, perfluoroethane, perfluoropropanes, perfluorobutanes, perfluoropentanes, perfluorohexanes and perfluoroheptanes; perfluoroalkenes such as perfluoropropene, perfluorobutenes; and perfluorocycloalkanes such as perfluorocyclobutane.

Microbubbles containing perfluorinated gases, in particular, perfluorocarbons such as perfluoropropanes, perfluorobutanes, perfluoropentanes and perfluorohexanes are suitable for use in the invention due to their stability in the bloodstream.

Microbubbles containing a perfluorocarbon, particularly a perfluoroalkane, and a shell comprising a phospholipid may be used in the invention and are described in, for example, Nomikou & McHale, Cancer Lett., 296: 133-143, 2010. One example of such a microbubble is Sonidel SDM202 (available from Sonidel Ltd.). The perfluorocarbon may either be present as a gas or in liquid form. Those containing a liquid core may be prepared from nanoemulsions which may subsequently be converted to a gas microbubble upon exposure to ultrasound, e.g. as described in Rapoport et al., Bubble Sci. Eng. Technol. 1: 31-39, 2009.

In one embodiment, the microbubbles for use in the invention may carry oxygen. As oxygen is a key substrate for SDT and many cancers are hypoxic, filling the core of the bubble with oxygen gas enhances the sonodynamic effect and the amount of singlet oxygen produced.

Sonosensitisers which may be used in the invention include compounds which render target cells or tissues hyper-sensitive to ultrasound. In some cases, a sonosensitiser may be capable of converting acoustic energy (e.g. ultrasound) into ROS that result in cell toxicity. Others may render the target cell or tissues hypersensitive to ultrasound by compromising the integrity of the cell membrane. It is well known that many known sonosensitisers can facilitate photodynamic activation and can also be used to render cells or tissues hypersensitive to light.

In one embodiment of the invention the sonosensitiser may simultaneously function as an imaging agent, for example as a NIR agent. Such sensitisers offer benefit in terms of their imaging potential enabling tracking of the conjugates in vivo.

Examples of compounds suitable for use as sonosensitisers in the invention include phenothiazine dyes (e.g. methylene blue, toluidine blue), Rose Bengal, porphyrins (e.g. Photofrin®), chlorins, benzochlorins, phthalocyanines, napthalocyanines, porphycenes, cyanines (e.g. Merocyanine 540 and indocyanine green), azodipyromethines (e.g. BODIPY and halogenated derivatives thereof), acridine dyes, purpurins, pheophorbides, verdins, psoralens, hematoporphyrins, protoporphyrins and curcumins. Any known analogues or derivatives of these agents may also be used. Suitable derivatives include the pharmaceutically acceptable salts.

Preferred for use as sonosensitisers in the invention are methylene blue, Rose Bengal, indocyanine green (ICG, also known as Cardio Green), and any analogues and derivatives thereof. Particularly preferred for use in the invention is Rose Bengal. ICG has the following structure:

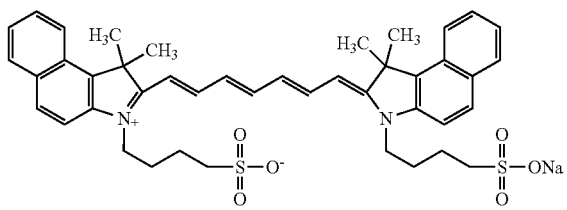

Known analogues of any of the sonosensitisers described herein may also be used in the invention. Particularly suitable are structural analogues of the cyanine-based dyes, e.g. structural analogues of ICG and their pharmaceutically acceptable salts. Examples of these include the cyanine dyes IR820 and IR783, both of which are commercially available:

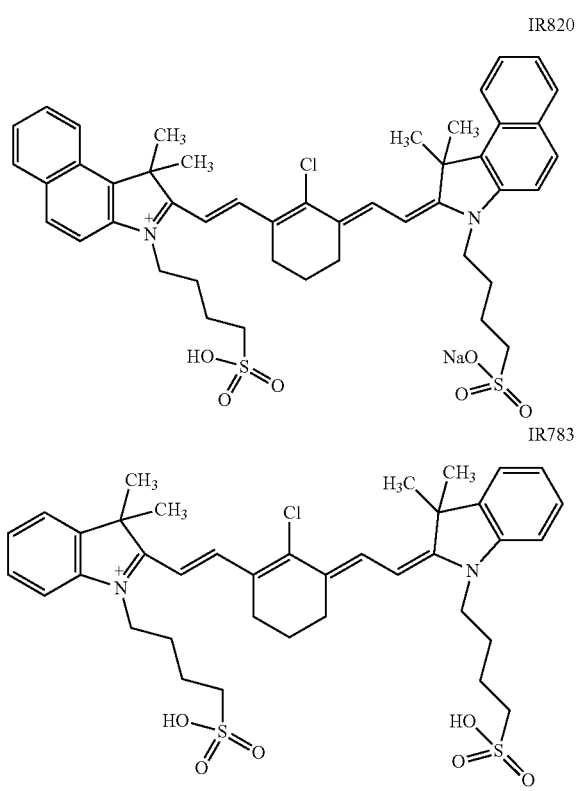

The near-infrared (NIR) absorbing fluorescent dye ICG is FDA approved for use in medical imaging. It absorbs strongly in the NIR region (750-900 nm) and has the advantage that this can be activated by light at a greater depth in human tissue (the penetration of light at 800 nm is four times greater than at 600 nm). However, the singlet oxygen generation (SOG) effectiveness of cyanine dyes such as ICG, IR820 and IR783 is relatively poor when compared to other known sensitisers such as Rose Bengal. This can be overcome by concentrating more cyanine molecules onto the microbubble.

Other attempts have been made to improve the ROS generating capability of cyanine dyes by incorporation of halogen atoms (e.g. iodine and bromine) into their structure. For example, in US 2013/0231604 (the entire contents of which are incorporated herein by reference) it is proposed that cyanine-based dyes and analogues of such dyes may be modified by incorporation of three iodine atoms on the benzene or napthalene portion of each benzazole or napthazole ring. Any of the polymethine dyes (in particular the cyanines) disclosed in this document may be used as sonosensitisers in the present invention.

In a development of the work documented in US 2013/0231604, the present inventors have prepared structural analogues of certain cyanine dyes (e.g. IR783) carrying either one or two halogen atoms (e.g. iodine or bromine, preferably iodine) on each of the benzazole rings and found these have enhanced ROS generating capability and are thus more cytotoxic to cancer cells (e.g. pancreatic cancer cells) upon ultrasound activation compared to ICG. Although not wishing to be bound by theory, the presence of the halogen atoms is believed to increase intersystem crossing (ISC) from the excited singlet to the excited triplet state due to what is known as the "heavy atom effect". The triplet excited state is then able to engage with molecular oxygen or other substrates to generate ROS. That such a level of enhanced ROS generating capability may be achieved by replacing fewer (i.e. a total of either 2 or 4) hydrogen atoms in IR783 with halogen atoms (e.g. iodine) could not be predicted in light of the teaching of US 2013/0231604.

Furthermore, as will be discussed in more detail below, the inventors have surprisingly found that when IR783 is substituted with a total of two halogen atoms (i.e. just one halogen atom, e.g. iodine, on each of the benzazole rings), the compound remains highly fluorescent and thus can also be used as a NIR imaging agent. Since any increase in ISC typically reduces the ability of a compound to emit fluorescence, this finding is unexpected. Combined, the NIR imaging potential and sensitiser potential of these particular analogues of IR783 means these compounds have "theranostic" potential, i.e. the ability to function both as a therapeutic and diagnostic agent.

Halogenated (e.g. iodinated) analogues of IR783 may be used in the invention and these may be represented by a compound of formula VII or formula VIII, or a pharmaceutically acceptable salt thereof:

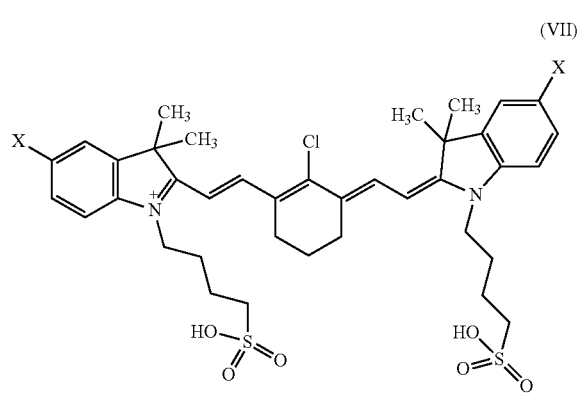

(VII)

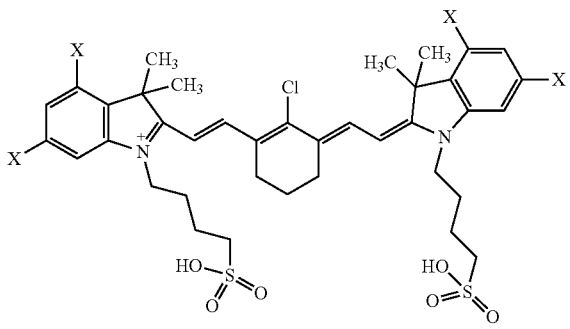

(VIII)

(wherein in formula VII and formula VIII each X is independently selected from a bromine and iodine atom, preferably wherein each X is iodine).

Suitable salts of such compounds and methods for their preparation may readily be selected by those skilled in the art. The compounds may, for example, be converted into a suitable pharmaceutically acceptable salt thereof with an inorganic or organic base. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

Preferred compounds of formula VII and VIII include the following and their pharmaceutically acceptable salts:

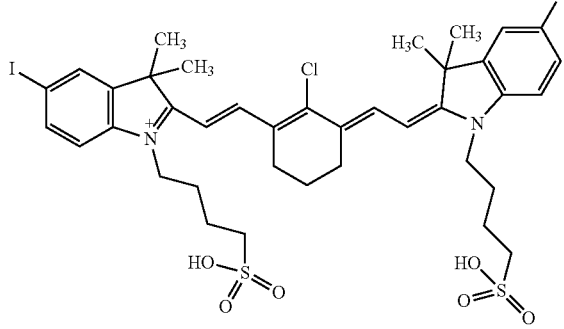

(VIIa)

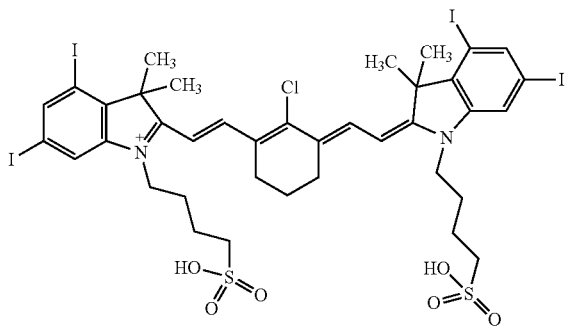

(VIIIa)

Methods for the formation of microbubbles are known in the art. Such methods include the formation of a suspension of the gas in an aqueous medium in the presence of the selected shell material. Techniques used to form the microbubble include sonication, high speed mixing (mechanical agitation), coaxial electrohydrodynamic atomisation and microfluidic processing using a T-junction (see e.g. Stride & Edirisinghe, Med. Biol. Eng. Comput., 47: 883-892, 2009). Sonication is widely used and generally preferred. This technique may be carried out using an ultrasound transmitting probe. More particularly, an aqueous suspension of the microbubble shell components is sonicated in the presence of the relevant microbubble component gas, e.g. oxygen.

Other methods which may be used to form the microbubbles include vaporisation of a nanodroplet core in a nanoemulsion (see e.g. Rapoport et al., supra). The core of such nanodroplets will typically be formed by an organic perfluorocompound which is encased by a lipid shell or a biodegradable amphiphilic block copolymer such as poly(ethylene oxide)-co-poly(L-lactide) or poly(ethylene oxide)-co-caprolactone.

Alternatively, nanoemulsions may be prepared by extrusion through sizing membranes, for example using albumin as the shell material. The droplet-to-bubble transition may be induced by physical and/or mechanical means which include heat, ultrasound and injection through a fine-gauge needle. Such microbubbles may be formed at the point of administration to the patient (e.g. during the step of administration using a fine-gauge needle) or in vivo at the desired target cells or tissues (e.g. by subjecting the nanoemulsion to ultrasound).

Administration of a nanodroplet which is capable of forming the desired microbubble complex as herein defined, either during the step of administration to the patient or post-administration (i.e. in vivo), is within the scope of the present invention. Where it is desired that the resulting microbubble contains oxygen gas, this may be provided in dissolved form in a liquid perfluorocarbon core of a phase-shift nanoemulsion.

The microbubble complexes herein described may be prepared using methods and procedures known in the art. Methods which may be used for covalently attaching the chemotherapeutic agent and/or the sonosensitising agent to a linking group include known chemical coupling techniques. The exact method used will be dependent on the exact nature of the linking group, the chemotherapeutic agent and the sonosensitising agent, specifically the nature of any pendant functional groups. If necessary, one or both components which are to be linked may be functionalised, e.g. to include reactive functional groups which may be used to couple the molecules. Suitable reactive groups include acid, hydroxy, carbonyl, acid halide, thiol and/or primary amine. Methods for the introduction of such functional groups are well known in the art.

Examples of methods which may be used to covalently bind a linking group to one or more chemotherapeutic agents and/or sonosensitising agents include, but are not limited to, the following:
  a) Carbodiimide based coupling methods. These may be used to couple linking groups containing either an amine or carboxylic acid functionality to a moiety having either a carboxylic acid or amine functionality. Such methods result in the formation of ester or amide bonds;
  b) "CLICK" reaction (i.e. 1,3-dipolar cycloaddition reaction). This may be used to react azide or acetylene functionalised linkers with a moiety having either acetylene or azide functionality;
  c) Schiff base formation (i.e. imine bond formation). This reaction may be used to bond aldehyde or amine functionalised linkers to a moiety containing amine or aldehyde functionality; and
  d) Michael addition reactions.

Linkage of the microbubble to one or more linking groups via the biotin-avidin linkage may be carried out by methods known to those skilled in the art. In such methods, both moieties will typically be biotinylated and avidin then used to form the linkage between the two. An example of a method to produce a microbubble complex according to the invention in which the microbubble is bound to the linking group via a biotin-avidin-biotin interaction is provided in scheme 2 in Example 1.

As an alternative to coupling of the linking group to a pre-formed microbubble, this may alternatively be linked to a lipid (e.g. using any of the methods described above) and that lipid may subsequently be incorporated into the lipid shell of the microbubble during its preparation.

Any of the methods herein described for preparation of the microbubble complexes form further aspects of the invention.

Any of the intermediates formed in any of the methods herein described are also considered to form part of the invention, for example any intermediates produced during the procedures outlined in Schemes 1-5 in the examples herein. Examples of such intermediates include the Gemcitabine-Biotin conjugate (4) in Scheme 1, the Biotin-Gemcitabine-Rose Bengal conjugate (9) in Scheme 2, the Biotin-Doxorubicin conjugate (3) in Scheme 3, the Biotin-Doxorubicin-Rose Bengal conjugate (9) in Scheme 4 and the Biotin-Gemcitabine-Rose Bengal conjugate (9) in Scheme 5.

The microbubble complexes herein described have properties which render these useful in methods of sonodynamic therapy.

The complexes are suitable for the treatment of disorders or abnormalities of cells or tissues within the body which are responsive to sonodynamic therapy. These include malignant and pre-malignant cancer conditions, such as cancerous growths or tumours, and their metastases; tumours such as sarcomas and carcinomas, in particular solid tumours. The invention is particularly suitable for the treatment of tumours, especially those which are located below the surface of the skin.

Examples of tumours that may be treated using the invention are sarcomas, including osteogenic and soft tissue sarcomas; carcinomas, e.g. breast, lung, cerebral, bladder, thyroid, prostate, colon, rectum, pancreas, stomach, liver, uterine, hepatic, renal, prostate, cervical and ovarian carcinomas; lymphomas, including Hodgkin and non-Hodgkin lymphomas; neuroblastoma, melanoma, myeloma, Wilm's tumour; leukemias, including acute lymphoblastic leukaemia and acute myeloblastic leukaemia; astrocytomas, gliomas and retinoblastomas. Treatment of pancreatic cancer forms a preferred aspect of the invention.

In one aspect, the complexes herein described may be used in a method of sonodynamic therapy and, simultaneously, a method of in vivo imaging (e.g. a method of diagnostic imaging). In such methods, imaging may be used to monitor payload deposition and/or accumulation of the complex (or complexes) at the target site of interest. As described above, this aspect of the invention may be realised by selection of a sonosensitiser which has imaging potential, e.g. a sonosensitiser which simultaneously functions as a NIR imaging agent. Alternatively a known imaging agent, such as a NIR imaging agent, may also be conjugated to the microbubble proposed for use in the invention. The NIR imaging agent may be conjugated (e.g. via a non-covalent linkage such as a biotin-avidin interaction) to the microbubble.

In addition to providing a means of targeting a chemotherapeutic agent and a sonosensitiser to a particular site in vivo, the methods herein described may further be exploited ex vivo. For example, in autologous bone marrow transplantation in the treatment of leukaemia, bone marrow from the patient may be treated ex vivo by molecular targeting of the microbubble complex to cancerous cells. These mixtures may then be treated with ultrasound to destroy the cancerous cells and the treated marrow may then be used to re-establish haematopoiesis in the patient following radiation treatment. Alternatively, the methods of the invention may be carried out ex vivo to remove unwanted tissues from organs harvested for conventional transplant. Surgically removed tissues may be targeted and lesions destroyed prior to autologous or heterologous re-transplantation of the treated tissue.

For use in any of the methods herein described, the microbubble complexes will generally be provided in a pharmaceutical composition together with at least one pharmaceutically acceptable carrier or excipient. Such compositions form a further aspect of the invention.

The pharmaceutical compositions for use according to the invention may be formulated using techniques well known in the art. The route of administration will depend on the intended use. Typically, these will be administered systemically and may thus be provided in a form adapted for parenteral administration, e.g. by intradermal, subcutaneous, intraperitoneal or intravenous injection. Suitable pharmaceutical forms include suspensions and solutions which contain the active microbubble complexes together with one or more inert carriers or excipients. Suitable carriers include saline, sterile water, phosphate buffered saline and mixtures thereof.

The compositions may additionally include other agents such as emulsifiers, suspending agents, dispersing agents, solubilisers, stabilisers, buffering agents, wetting agents, preserving agents, etc. The compositions may be sterilised by conventional sterilisation techniques.

Solutions containing the complexes may be stabilised, for example by the addition of agents such as viscosity modifiers, emulsifiers, solubilising agents, etc.

Preferably, the compositions for use in the invention will be used in the form of an aqueous suspension of the microbubble complexes in water or a saline solution, e.g. phosphate-buffered saline. The complexes may be supplied in the form of a lyophilised powder for reconstitution at the point of use, e.g. for reconstitution in water, saline or PBS.

The methods herein described involve administration of a therapeutically effective amount of the composition which contains the microbubble complexes. The microbubble complexes may then be allowed to distribute to the desired portion or target area of the body prior to activation. Once administered to the body, the target area is exposed to ultrasound at a frequency and intensity to achieve the desired therapeutic effect. A typical activation procedure may involve a two-step process in which the microbubbles are first ruptured by focused ultrasound thereby releasing the sonosensitiser and chemotherapeutic agent which are then able to penetrate the desired target tissue (e.g. tumour). Subsequent sono-activation of the sonosensitiser within the target cells results in production of singlet oxygen which can oxidise various cell components such as proteins, lipids, amino acids and nucleotides thereby destroying the target cells. Whilst it is envisaged that activation of the sonosensitiser will typically take place subsequent to its delivery (i.e. following burst of the microbubbles to release the sonosensitiser), delivery of the complex and activation of the sonosensitiser may nevertheless be simultaneous.

Alternatively, any of the methods herein described may involve exposure of the target area in the body to ultrasound during administration of the composition which contains the microbubble complexes, i.e. administration of the microbubble complexes and delivery of ultrasound may be carried out simultaneously. Where the half-life of the microbubble complex is low, this can avoid the situation in which a significant proportion may be removed before the target area receives the ultrasound.

The effective dose of the compositions herein described will depend on the nature of the complex, the mode of administration, the condition to be treated, the patient, etc. and may be adjusted accordingly.

The frequency and intensity of the ultrasound which may be used can be selected based on the need to achieve selective destruction of the microbubble at the target site and may, for example, be matched to the resonant frequency of the microbubble. Ultrasound frequencies will typically be in the range 20 kHz to 10 MHz, preferably 0.1 to 2 MHz. Ultrasound may be delivered as either a single frequency or a combination of different frequencies. Intensity (i.e. power density) of the ultrasound may range from about 0.1 W/cm$^2$ to about 1 kW/cm$^2$, preferably from about 1 to about 50 W/cm$^2$. Treatment times will typically be in the range of 1 ms to 20 minutes and this will be dependent on the intensity chosen, i.e. for a low ultrasound intensity the treatment time will be prolonged and for a higher ultrasound intensity the treatment time will be lower. Ultrasound may be applied in continuous or pulsed mode and may be either focused or delivered as a columnar beam.

Any radiation source capable of producing acoustic energy (e.g. ultrasound) may be used in the methods herein described. The source should be capable of directing the energy to the target site and may include, for example, a probe or device capable of directing energy to the target tissue from the surface of the body.

In cases where the ultrasound frequencies and/or intensities that are needed to achieve cavitation (or microbubble destruction) and those required to cause sonosensitiser activation are different, these different sets of ultrasound parameters (frequency/intensity) may be applied simultaneously or in a two (or multiple)-step procedure.

A further aspect of the invention relates to a method of sonodynamic treatment of cells or tissues of a patient, which method comprises:

(a) administering to the affected cells or tissues an effective amount of a composition as herein described; and
(b) subjecting said cells or tissues to ultrasound.

In the case where the sonosensitiser used is one which also responds to light, ultrasound activation may be accompanied by light activation. Photothermal activation may also additionally be employed, for example when using a NIR dye as the sonosensitiser.

In a still further aspect the invention provides a kit comprising: (i) a microbubble complex as described herein; and (ii) instructions for the use of (i) in a method of sonodynamic therapy and/or diagnostic imaging. In one embodiment of the kit, component (i) may be provided in dry form, e.g. as a lyophilised powder. In this case, the kit may also comprise a container containing a sterile, physiologically acceptable liquid, and optionally a gas, for reconstitution of the powdered form of the active, e.g. saline or PBS, and oxygen or a perfluorocarbon, respectively.

Whilst the various methods and uses according to the invention are primarily described herein in the context of administration of a "ready-to-use" microbubble complex, in an alternative embodiment a precursor of the complex may be administered. The term "precursor" as used herein is intended to refer to a precursor for the microbubble complex which is converted in vivo to it and is thus essentially equivalent thereto. Thus, for example, the term "precursor" encompasses nanoemulsions or nanodroplet formulations which are capable of conversion to the desired microbubble complex either in vivo or during administration. In one embodiment, such precursors are capable of conversion to the desired complex upon accumulation in the target tissue (e.g. tumour tissue). Following distribution to the target tissue or cells, the droplet-to-bubble transition may be triggered by methods which include ultrasound. Alternatively, the step of administration of a precursor of the complex may itself induce formation of a microbubble complex according to the invention. For example, where the precursor takes the form of a nanoemulsion, droplet-to-bubble transition may be induced by injection through a fine gauge needle or by subjecting the preparation to an appropriate phase transition stimulus, e.g. heat. Direct injection of suitable nanoemulsions into target cells or tissues, for example into tumours, and phase transition in situ forms a further aspect of the invention.

As will be appreciated, in any of the compositions, methods or uses herein described, any reference to a microbubble complex according to the invention may be replaced by a suitable "precursor" as defined herein.

Nanoemulsions or nanodroplet formulations for use as microbubble complex precursors according to the invention may be produced by appropriate modification of methods and procedures known in the art, for example those disclosed by Rapoport et al. (supra). In such formulations, the cores of nanoemulsion droplets, which may be formed by a liquid perfluorocarbon (e.g. a perfluoroalkane), are encased by walls of suitable polymeric, protein or lipid shell materials (e.g. any of the polymers described herein in relation to the microbubble complexes). Linkage of the shells of the nanodroplets to a linking group carrying a sonosensitiser and chemotherapeutic agent may be achieved using conventional methods and include any of those described above for attaching the linking group to a pre-formed microbubble. The exact method used will be dependent on the exact nature of the shell material and the linking group, specifically the nature of any pendant functional groups. If necessary, either the shell and/or the linking group may be functionalised, e.g. to include reactive functional groups which may be used to couple the moieties. Suitable reactive groups include acid, hydroxy, carbonyl, acid halide, thiol and/or primary amine. In one embodiment the shell may be functionalised with biotin and then bound to avidin to subsequently facilitate binding of a biotinylated linking group. Where it is desired that the formed microbubble will contain oxygen gas, the perfluorocarbon may act as a carrier for the oxygen in liquid form. Following formation of the complex, the perfluorocarbon liquid is saturated with oxygen which subsequently vaporises to form oxygen gas.

Incorporation of a chemotherapeutic agent (or agents) within the shell of the microbubble is described herein primarily in the context of a microbubble complex which is bound to a linking group which carries at least one additional chemotherapeutic agent and at least one sonosensitising agent. However, the inventors have recognised that this aspect of the invention has broader applicability and may be used in combination with other microbubble complexes, including the microbubble-sonosensitiser complexes which are known and described in WO 2012/143739, the entire content of which is incorporated herein by reference. It may also find use in the context of a microbubble-chemotherapeutic agent complex which comprises a microbubble attached to or otherwise associated with at least one chemotherapeutic agent. Such a complex may be used alone in any of the methods herein described, or alternatively it may be employed in combination (e.g. simultaneously) with a microbubble-sonosensitiser complex such as that described in WO 2012/143739. In these aspects of the invention the microbubble, sonosensitiser, and chemotherapeutic agents may be selected from any of those as defined herein.

Any of the microbubble complexes described herein (e.g. a microbubble-sonosensitiser complex or a microbubble-chemotherapeutic agent complex) having a chemotherapeutic agent embedded within the shell of the microbubble are in themselves novel and form further aspects of the invention. In one embodiment, the invention provides a microbubble-sonosensitiser complex having a taxol (e.g. paclitaxel) embedded within the shell of the microbubble, preferably in which the sonosensitiser is Rose Bengal. In another embodiment, the invention provides a microbubble-chemotherapeutic agent complex having a taxol (e.g. paclitaxel) embedded within the shell of the microbubble, preferably in which the chemotherapeutic agent is an antimetabolite (e.g. gemcitabine) or a topoisomerase inhibitor (e.g. doxorubicin).

In these broader aspects of the invention the sonosensitiser may be linked to the microbubble using methods known in the art, such as those described in WO 2012/143739, the entire contents of which are incorporated herein by reference.

Any of the methods disclosed in WO 2012/143739 may be applied analogously to the preparation of a microbubble-chemotherapeutic agent complex. In such methods, the components to be linked will typically be biotinylated and avidin then used to form a linkage between them. Methods for incorporation of the chemotherapeutic agent in the shell of the microbubble include any of those described herein.

Methods for the preparation of a microbubble-sonosensitiser complex or a microbubble-chemotherapeutic agent complex having a chemotherapeutic agent embedded within the shell of the microbubble which comprise the step of incorporating a chemotherapeutic agent into the microbubble shell, for example using any of the techniques herein described, faun a further aspect of the invention.

Any of the embodiments of the present disclosure relating to the nature of the microbubble, the sonosensitiser or the chemotherapeutic agent are equally applicable to these broader aspects of the invention. Similarly, any of the methods of therapy or uses herein described are equally applicable to these broader aspects of the invention.

The invention will now be described further with reference to the following non-limiting Examples and the accompanying drawings in which.

Figure 5:
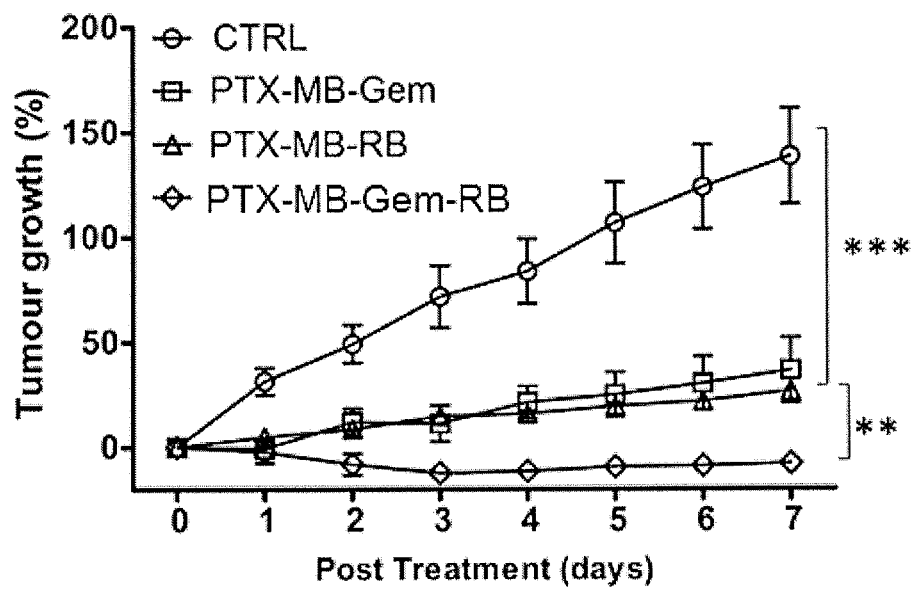

FIG. 5 shows a plot of tumour growth against time for mice bearing ectopic Mia-Paca-2 tumours treated with (i) no treatment (CTRL) (ii) PTX-MB-Gem (iii) PTX-MB-RB and (iv) PTX-MB-Gem-RB. Tumours were exposed to ultrasound during administration of the MB conjugates while the PTX-MB-RB and PTX-MB-Gem-RB received a second ultrasound exposure 30 min following injection. Treatments were administered on days 0, 1 and 2.

Figure 6:
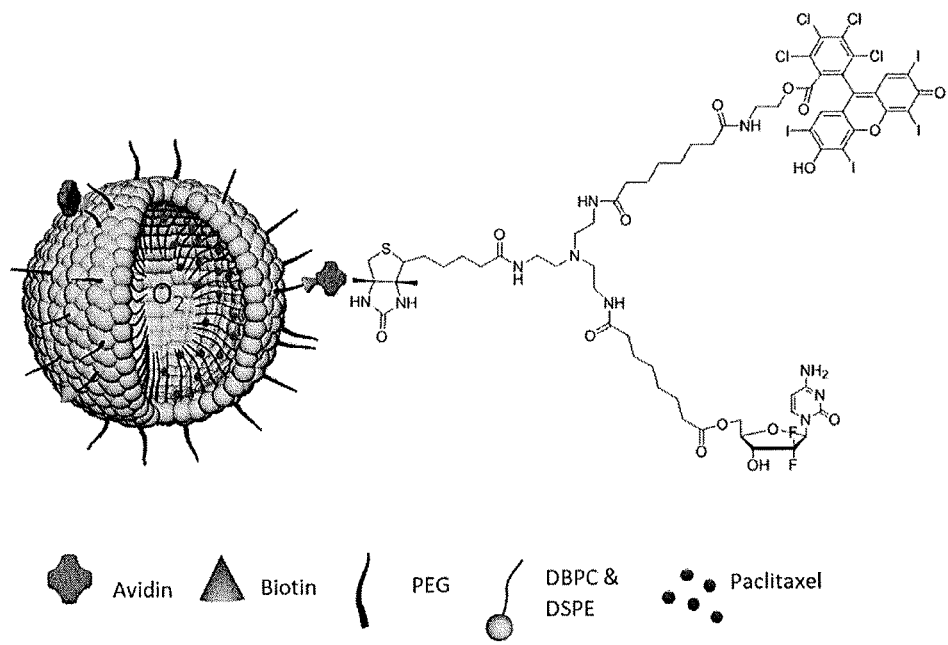

FIG. 6 shows a schematic representation of PTX/GEM/RB-MB.

Figure 7:
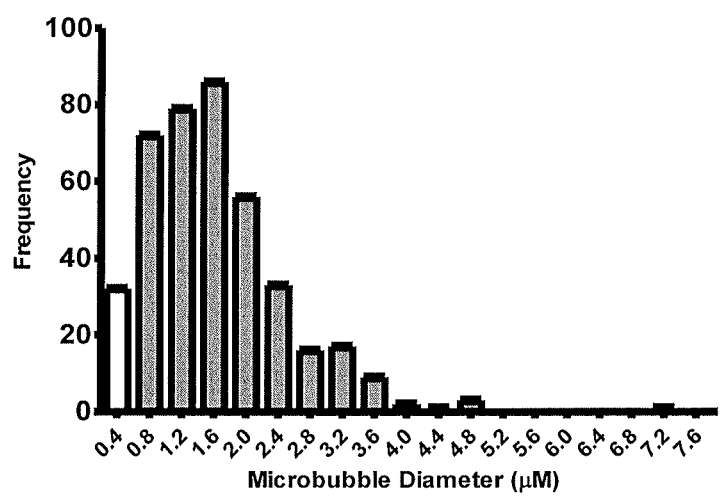

FIG. 7 shows the size distribution of PTX/GEM/RB-MB constructed from bright field and fluorescence microscope images.

Figure 8:
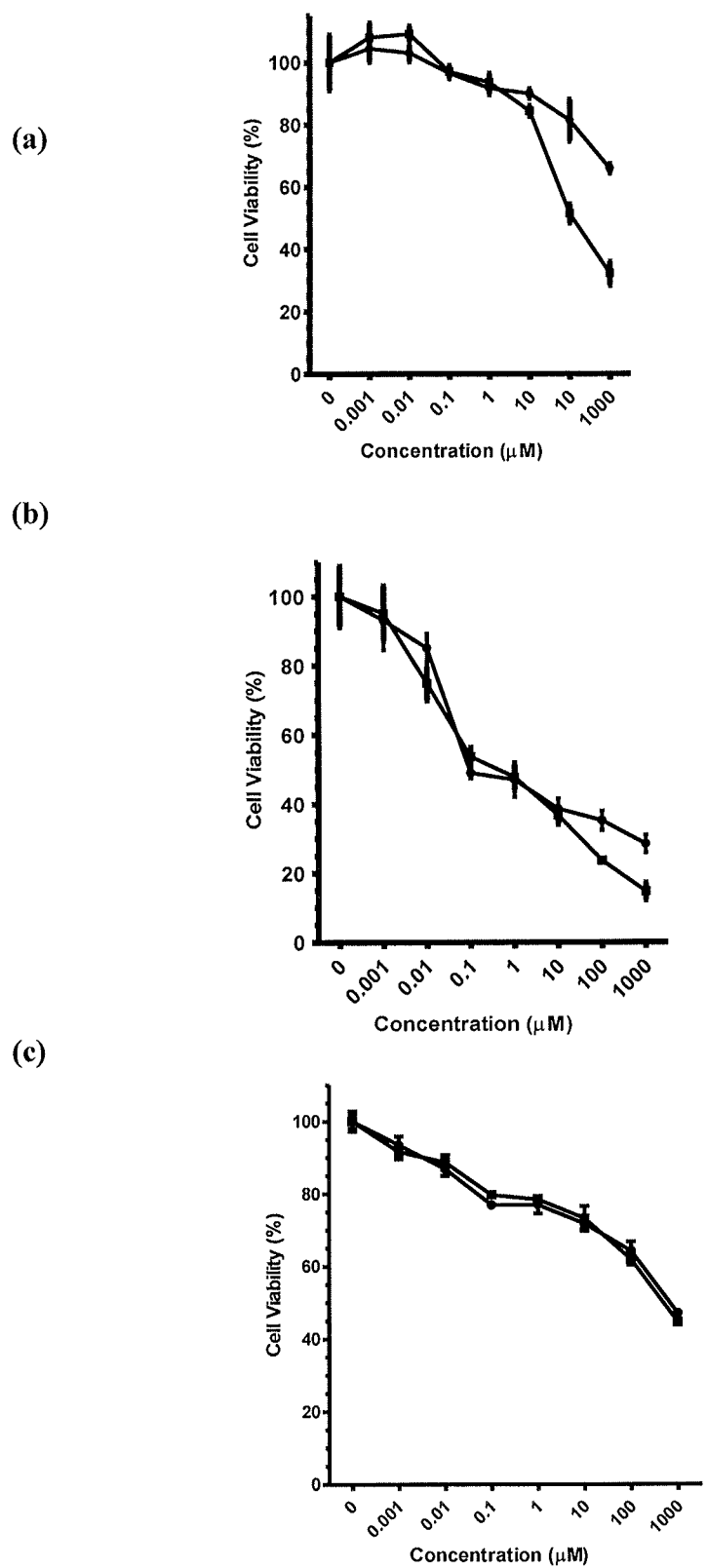

FIG. 8 shows the results of an MTT assay comparing the efficacy of biotin-GEM-RB (squares) with gemcitabine hydrochloride (circles) in Panc-1 (a) BxPc-3 (b) and Mia-PaCa-2 (c) cell lines.

Figure 9:
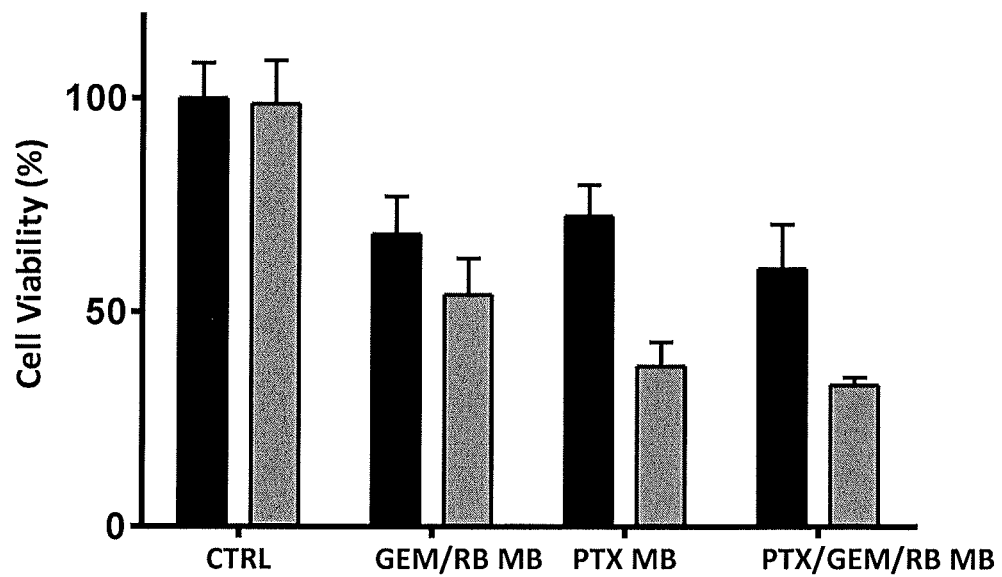

FIG. 9 shows the results of an MTT assay comparing the cell viability of Panc-1 spheroids following 48-hour incubation with of GEM/RB MBs (GEM/RB—5 µM), PTX MBs (PTX—6.6 µM) and PTX/GEM/RB MBs (PTX—6.6 µM, GEM/RB—5 µM) in Panc-1 spheroids with (grey) and without (black) ultrasound exposure.

Figure 10:
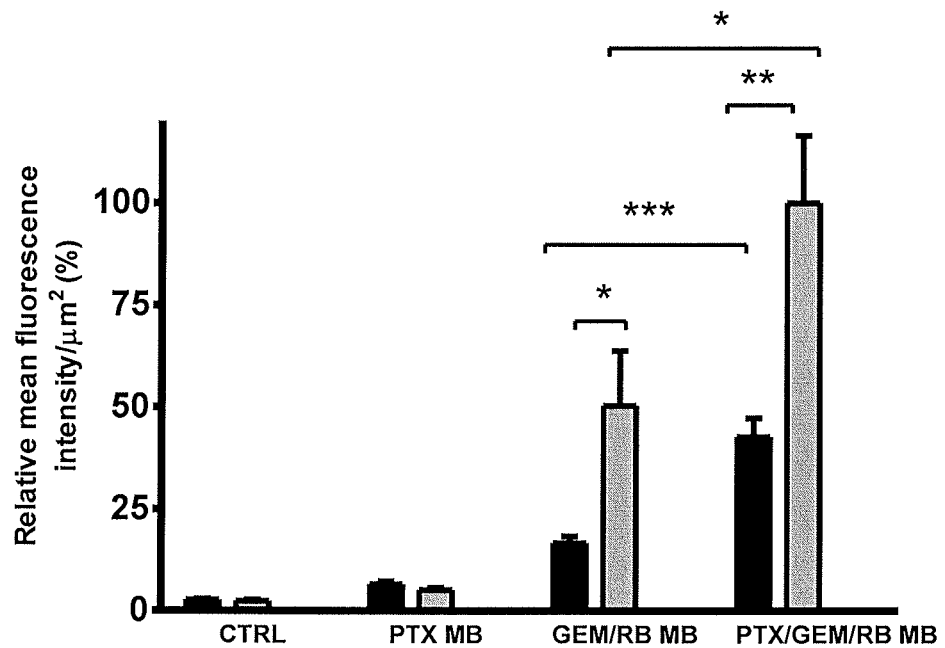

FIG. 10 shows the results of a Propidium Iodide (PI) assay comparing the cell viability of Panc-1 spheroids following 48-hour incubation with GEM/RB MBs (GEM/RB—6.8 µM), PTX MBs (PTX—5 µM) and PTX/GEM/RB MBs (PTX—5 µM, GEM/RB—6.8 µM) with (grey) and without (black) ultrasound exposure.

Figure 11:
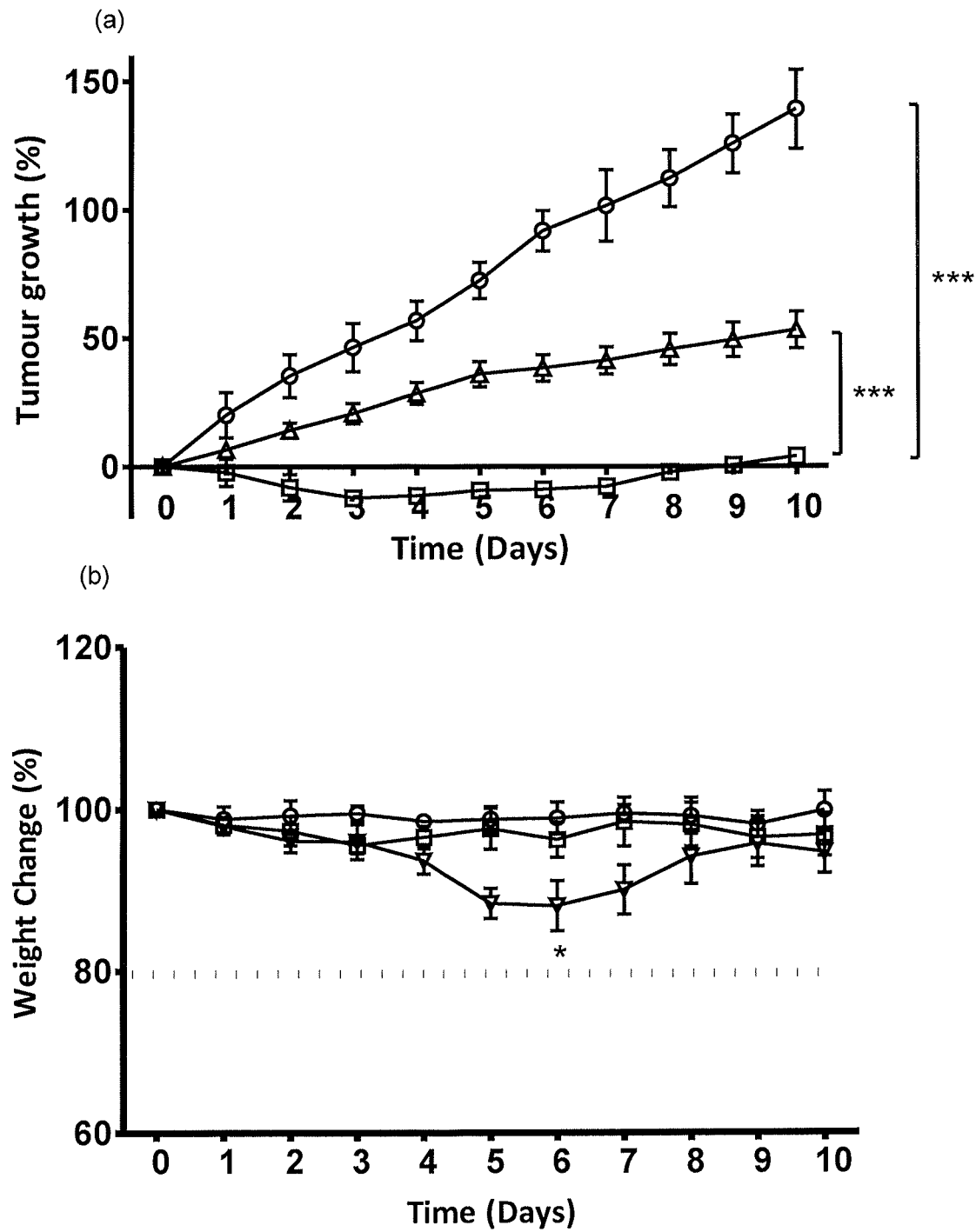

FIG. 11 shows a plot of (a) % change in tumour volume and (b) average body weight for Mia-PaCa-2 tumour bearing mice treated with (i) no treatment (circles) (ii) $O_2$MB-PTX/GEM/RB (squares) (iii) gemcitabine (triangles). The microbubble suspension ($6.86 \times 10^7 \pm 1.99 \times 10^6$ MB) was delivered as a 100 uL I.V injection (PTX—2.44±0.37 mg/Kg, GEM—0.5±0.04 mg/Kg, RB—1.85±0.14 mg/Kg). Gemcitabine hydrochloride was dissolved in sterile PBS and administered as a 100 uL I.P injection (120 mg/Kg). Ultrasound treatment was delivered for 3.5 minutes at frequency of 1 MHz, an ultrasound power density of 3.5 W/cm$^2$ and a duty cycle of 30% immediately after injection and 30 minutes following. Error bars represent±the standard error.

Figure 12:
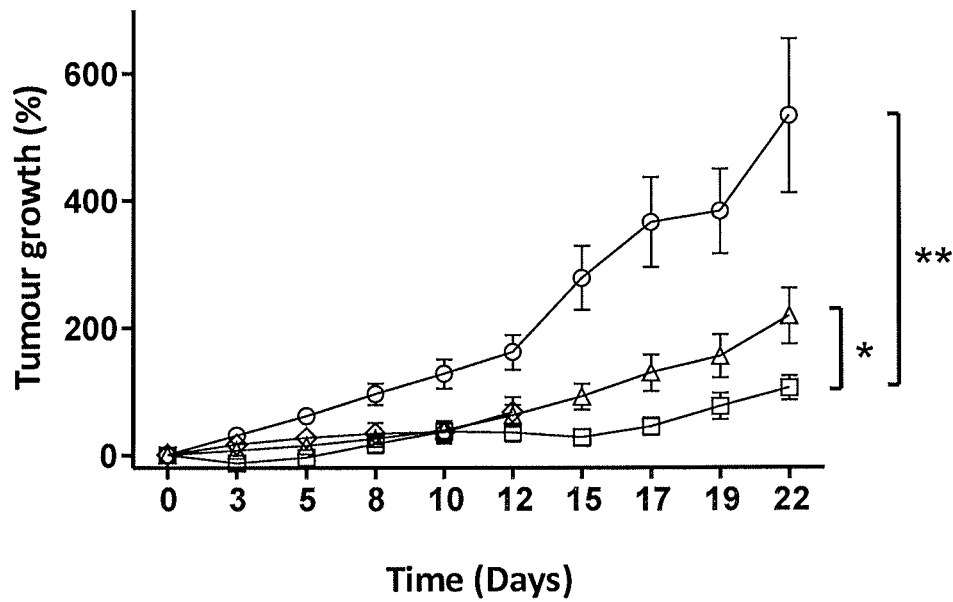

FIG. 12 shows a plot of % change in tumour volume for mice treated with (i) no treatment (circles) (ii) $O_2$MB-PTX/GEM/RB (squares) (iii) $O_2$MB-PTX (↑triangles) (v) gemcitabine +PTX in cremophorEL (diamonds). The microbubble suspensions ($O_2$MB-PTX/GEM/RB—$6.47 \times 10^7 \pm 1.86 \times 10^6$ MBs, $O_2$MB-PTX—$7.01 \times 10^7 + 1.5 \times 10^6$ MBs) were delivered as a 100 uL I.V. injection ($O_2$MB-PTX/GEM/RB—PTX—3.38±10.21 mg/Kg GEM—0.82±0.06 mg/Kg RB—3.02±0.24 mg/Kg, $O_2$MB—PTX—PTX—4.69±0.75 mg/Kg). Gemcitabine hydrochloride was dissolved in sterile PBS and administered as a 100 uL I.P. injection (120 mg/Kg). Paclitaxel was dissolved in 1 mL of ethanol, 1 mL of cremophor and 8 mL of sterile PBS and administered as a 100 uL I.V. injection. Ultrasound treatment was delivered for 3.5 minutes at frequency of 1 MHz, an ultrasound power density of 3.5 W/cm$^2$ and a duty cycle of 30% immediately after injection and 30 minutes following. Error bars represent±standard error of the mean.

Figure 13:
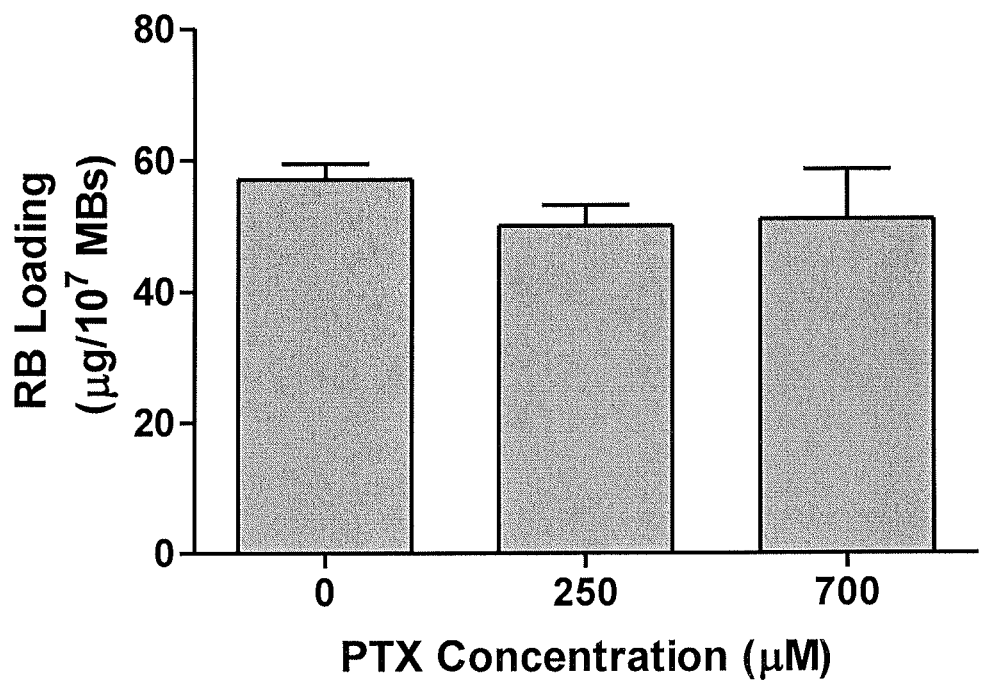

FIG. 13 is a graph showing the relative loading of biotin-RB as the concentration of paclitaxel increases from 0 to 5 mg.

Figure 14:
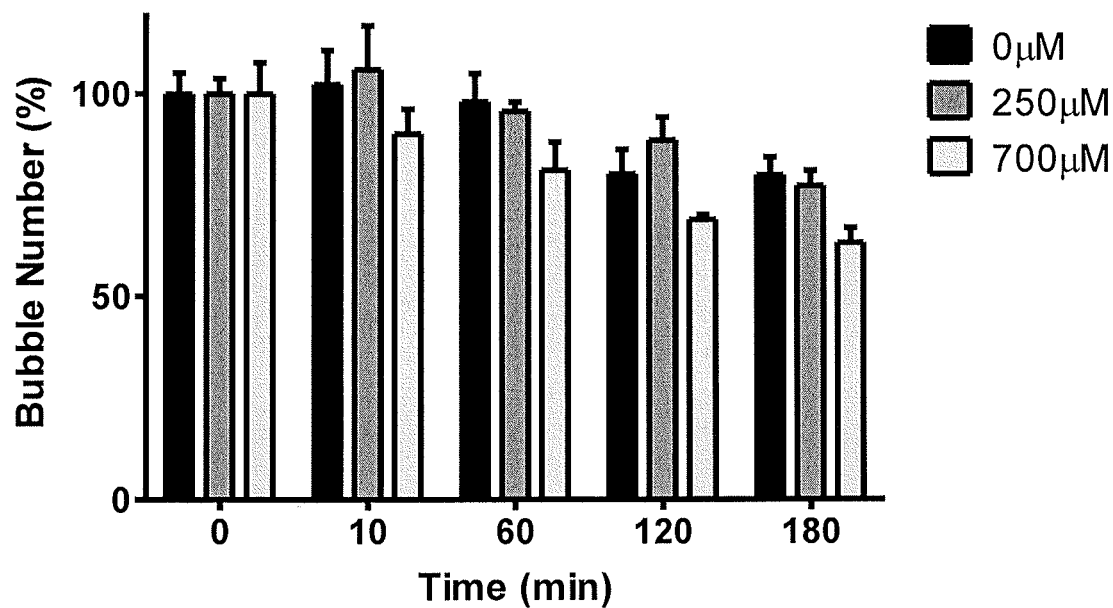

FIG. 14 is a graph showing the relative stability of MB formulations loaded with either 0 µM PTX (black bars), 250 µM PTX (dark grey bars) or 700 µM PTX (light grey bars) over a 3-hour period.

Figure 15:
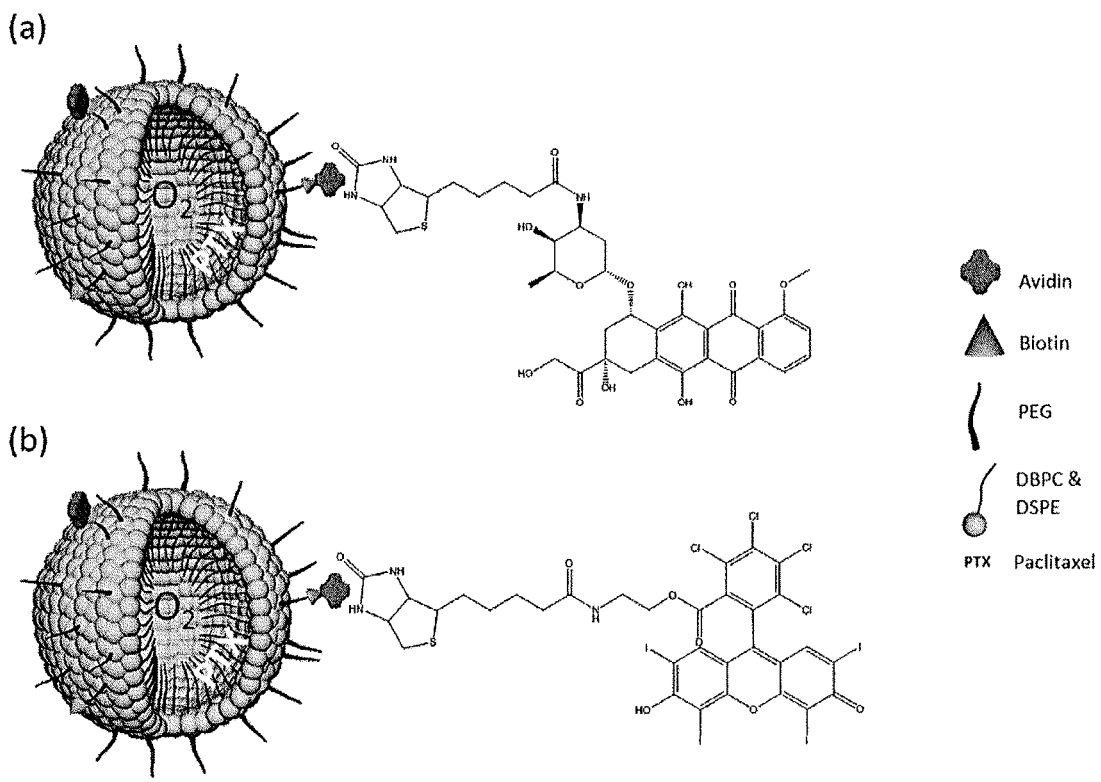

FIG. 15 is a schematic representation of a) $O_2$MB-PTX/DOX and b) $O_2$MB-PTX/RB.

Figure 16:
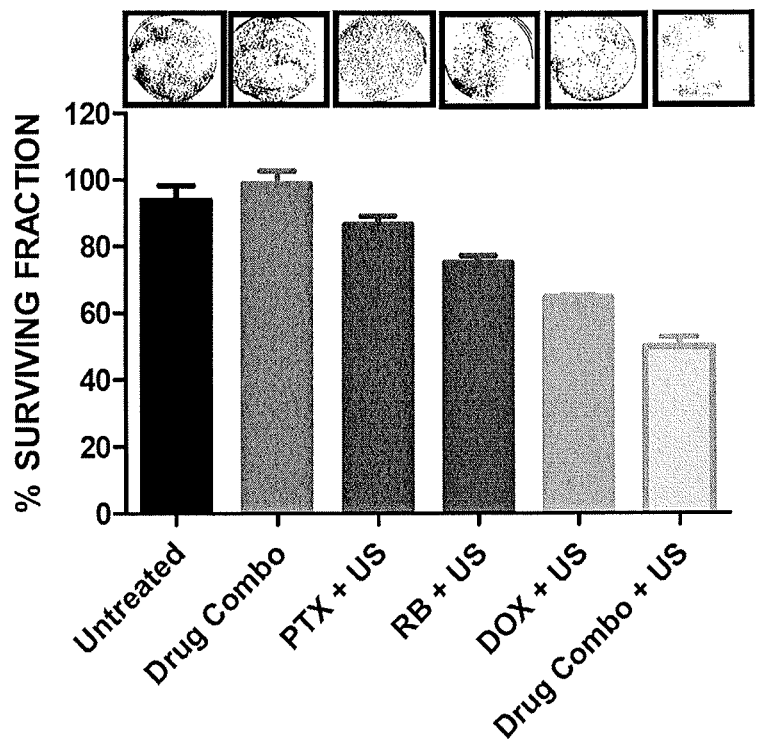

FIG. 16 is a plot showing % survival fraction from a MCF-7 colony forming assay. Cells following treatment with PTX/Dox/RB alone (Drug combo) or following treatment with ultrasound (Drug Combo+US). After treatment cells were incubated for 8 days followed by fixation and staining. Crystal violet staining was quantified via Image J.

Figure 17:
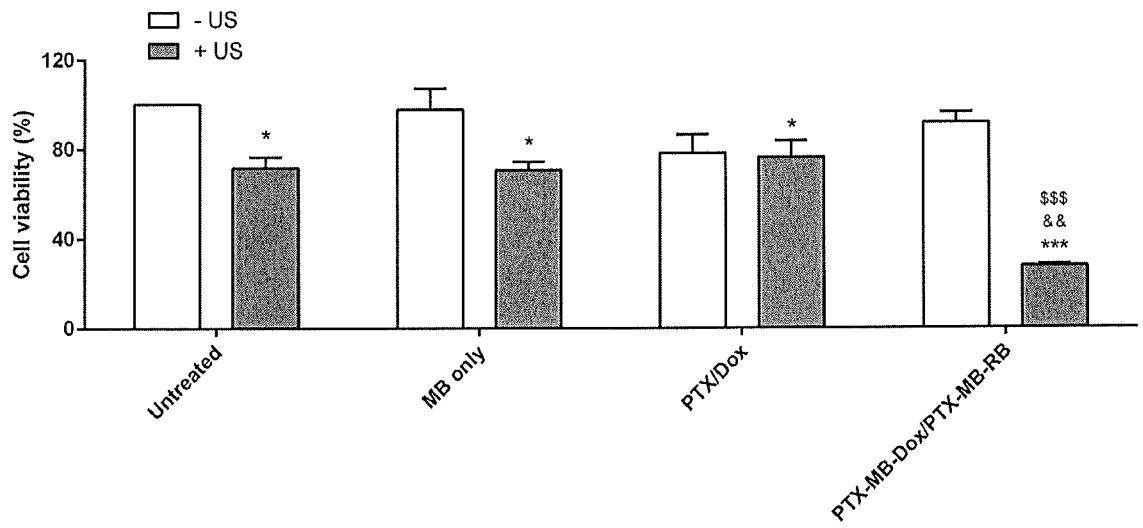

FIG. 17 is a plot showing cell viability of MCF-7 spheroids following treatment with (i) no treatment (ii) MB only (no drugs), (iii) PTX/Dox only (i.e. no MBs) or iv) PTX-MB-Dox/PTX-MB-Dox in the presence or absence of US (30 s, frequency of 1 MHz, 3.0 W/cm$^2$, 50% duty cycle. Statistical significant of samples treated with US versus untreated sample: *$p<0.05$, $p<0.01$, *$p<0.001$. Statistical significance of iv versus iii: && $p<0.01$. Statistical significance of iv treated with US versus iv untreated with US: \$\$\$ $p<0.001$. Error bars represent±the standard error, n=3.

Figure 18:
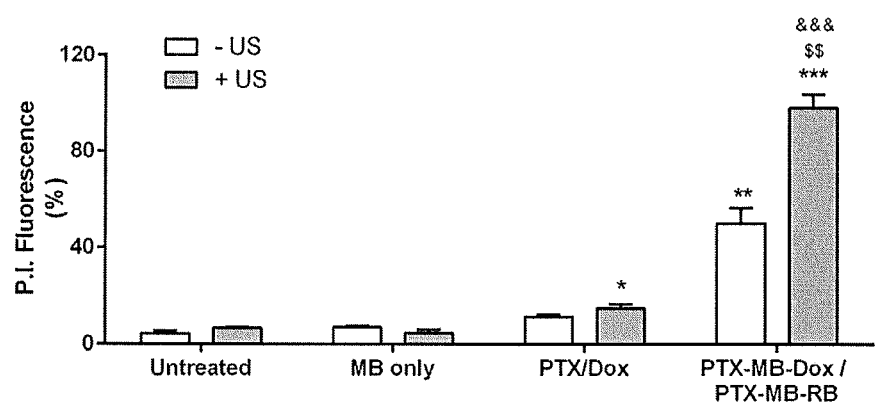

FIG. 18 is a plot showing relative PI fluorescence from fluorescence microscope images of MCF-7 spheroids treated with MB only (i.e. no MB); PTX/Dox only (i.e. no MBs); PTX-MB-Dox/PTX-MB-RB+/−US (30 s, 1 MHz, 3.0 W/cm$^2$, 50% duty cycle) and then stained with PI. Statistically significant of samples treated with US versus untreated sample: *$p<0.05$, $p<0.01$, *$p<0.001$. Statistically significance of iv versus iii: &&& $p<0.001$. Statistically significance of iv treated with US versus iv untreated with US: $p<0.01$. Error bars represent±the standard error, n=3.

Figure 19:
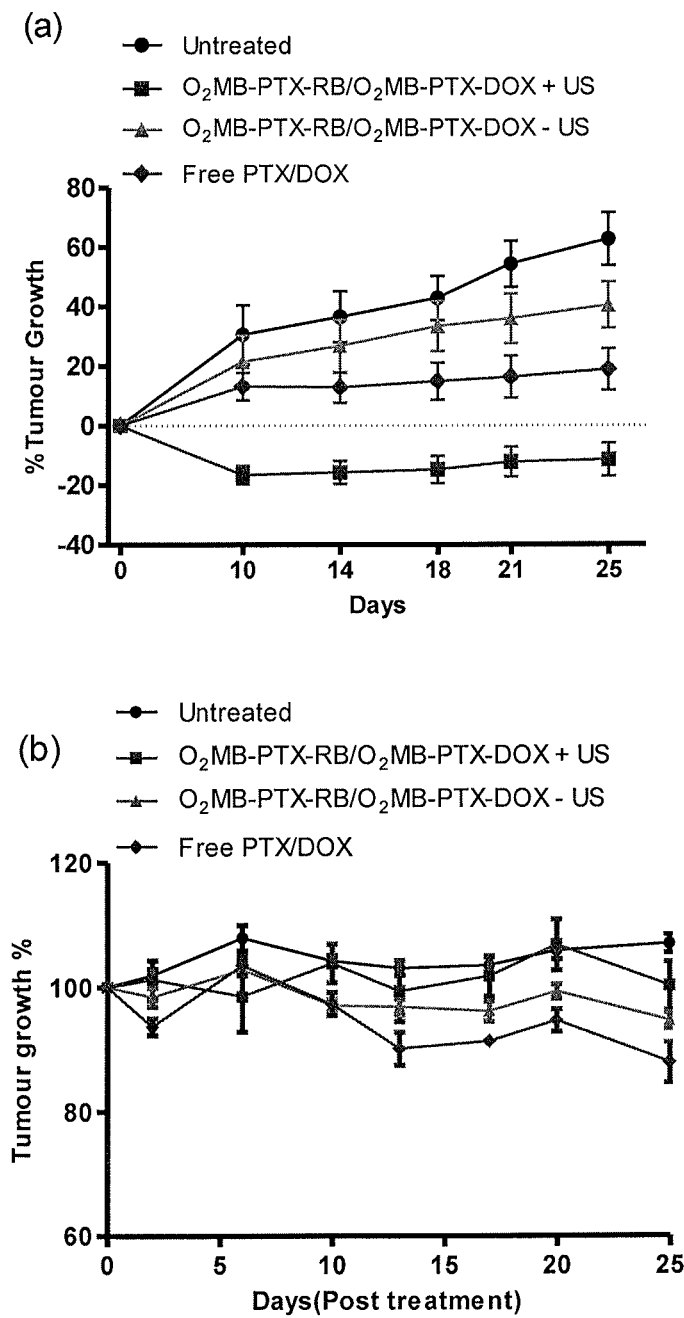

FIG. 19 shows: (a) Tumour growth delay plot in a MCF-7 Xenograft model following (1) no treatment (2) a mixed suspension (50 µL) of $O_2$MB-PTX/RB and $O_2$MB-PTX/Dox delivered by IV with US applied to the tumour during injection (3) as for (2) but without US treatment (4) $O_2$MB-PTX/Dox delivered by IV with US applied to the tumour during injection and (5) a Cremophor formulation containing free PTX and DOX. For MB treatments: [MB]=$1.2 \times 10^9$ MB/mL [PTX]=2.29 mg/kg; [DOX]=1.96 mg/kg and [RB] =5.34 mg/kg. For free PTX/DOX treatment in Cremophor: [PTX]=4.96 mg/kg and [Dox]=2.50 mg/kg. Error bars represent±SEM where n=5; and (b) Plot of animal weights recorded over the course of the experiments for each group.

EXAMPLE 1

Synthesis of Biotin-Gemcitabine (Biotin-Gem) and Biotin-Gemcitabine-Rose Bengal (Biotin-Gem-RB) Conjugates 1.1 Synthesis of Biotinylated Gemcitabine (Biotin-GEM)

Biotinylated Gemcitabine was synthesised according to scheme 1. The protocol is provided below.

Scheme 1: Synthetic scheme for the preparation of Biotin-Gem
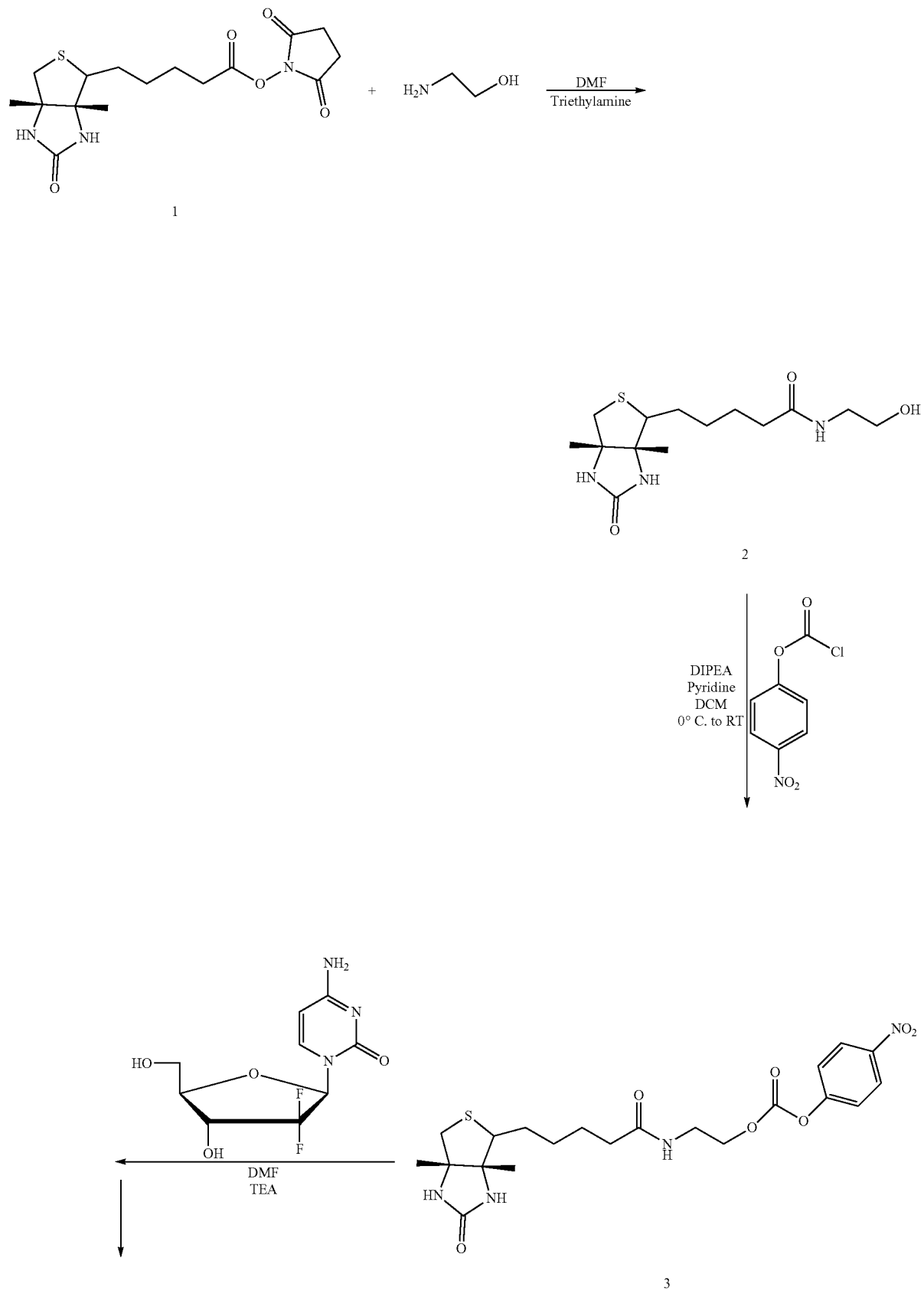

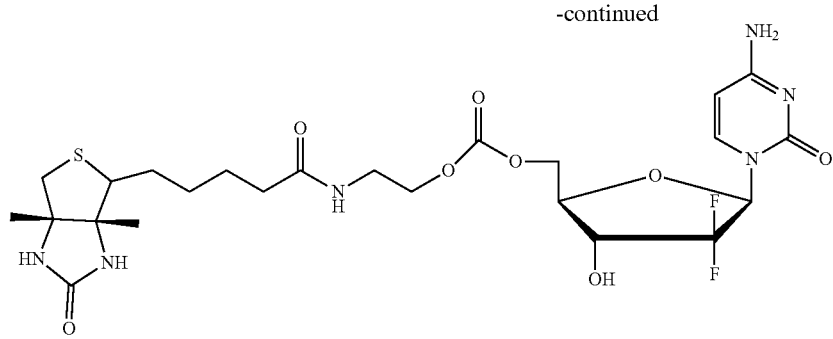

4
Gemcitabine-Biotin Conjugate

Synthesis of (2R,3R,5R)-5-(4-amino-2-oxopyrimidin-1(2H)-yl)-4,4-difluoro-3 hydroxytetrahydrofuran-2-yl)methyl (2-(5-(2-oxohexahydro-1H-thieno[3,4-d]imidazol-4-yl)pentanamido)ethyl) carbonate (4)

Compound 2 was prepared following a literature procedure (see McEwan et al. Biomaterials. 2016: 80, 20-32). To a DCM (10 mL) solution of 2 (0.28 g, 0.9 mmol), 4-nitrophenyl chloroformate (0.59 g, 2.9 mmol), DIPEA (0.50 g, 3.9 mmol) and a catalytic amount of pyridine were added at 0° C. and stirred for 24 hrs at room temperature. Then the reaction mixture was concentrated to dryness in vacuo. The crude residue containing 3 was dissolved in 20 mL DMF. To this solution, Gemcitabine (0.88 g, 2.9 mmol) in DMF (5 mL) and TEA (1 mL) were added and the mixture stirred for a further 24 hrs. After completion of reaction (monitored by TLC), excess diethyl ether (200 mL) was added to the reaction mixture and stirred for 45 min. The yellowish oil thus obtained was separated and washed three times with cold diethyl ether (50 mL×3). The crude compound was purified by PTLC using DCM/MeOH (9:1) as eluent to afford the target compound 4 (0.12 g, 22% yield).

$^1$H NMR (DMSO-d$_6$): δ7.99-7.91 (m, 3H, CH, NH$_2$), 6.41-6.33 (m, 1H, CH), 6.12-6.01 (m, 3H, CH, NH X 2), 4.30-4.16 (m, 1H, CH), 4.19-4.12 (m, 3H, CH, CH$_2$), 3.90-3.75 (m, 2H, CH$_2$), 3.69-3.58 (m, 2H, CH$_2$), 3.12-3.09 (m, 1H, CH), 2.93-2.88 (m, 2H, CH$_2$), 2.83 (brs, 1H, OH), 2.82-2.77 (m, 2H, CH X2), 2.72 (brs, 1H, NH), 2.49-2.04 (m, 2H, CH$_2$), 1.49-1.28 (m, 6H, CH$_2$ X 3).

$^{13}$C NMR (DMSO-d$_6$): 175.0 (C=O), 166.3 (C), 165.5 (C=O), 156.3 (C=O), 156.1 (C=O), 141.3 (CH), 125.3 (C), 95.2 (CH), 79.2 (CH), 67.2 (CH), 61.9 (CH), 60.2 (OCH$_2$), 55.5 (OCH$_2$), 39.6 (CH), 37.8 (CH$_2$), 35.2 (CH), 28.3 (CH$_2$), 28.0 (CH$_2$), 25.3 (CH$_2$). ESI-MS: cald for C$_{22}$H$_{30}$F$_2$N$_6$O$_8$S, 576.18; found 577.2 (M+H).

1.2 Synthesis of Biotin-Gem-RB

Biotin-Gem-RB was synthesised according to Scheme 2. The protocols for each intermediate are provided below.

Scheme 2: Synthetic scheme for the preparation of Biotin-Gem-RB

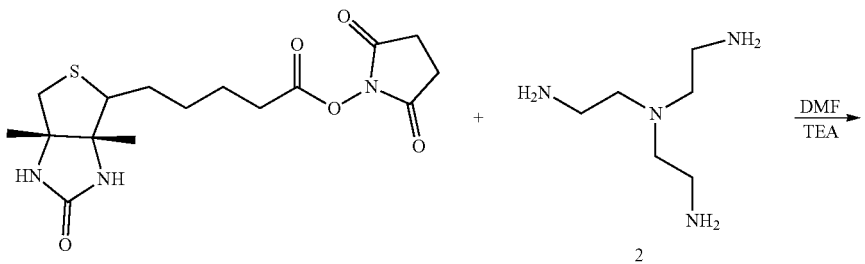

-continued
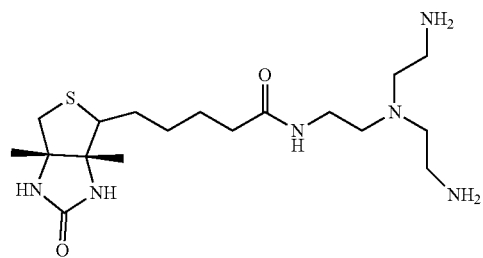
3
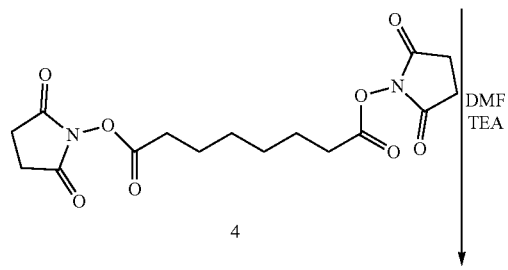
4
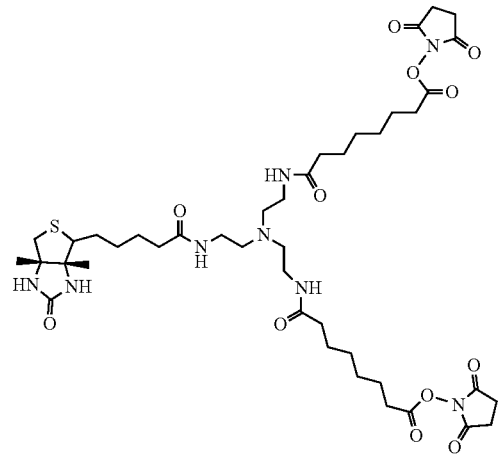
5
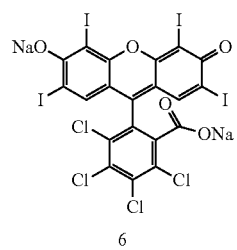
6
↓ Br—CH₂—CH₂—NH₂
DMF, TEA
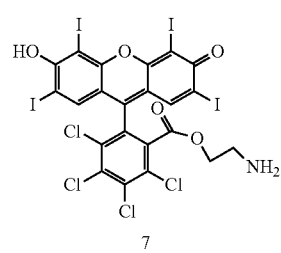 + 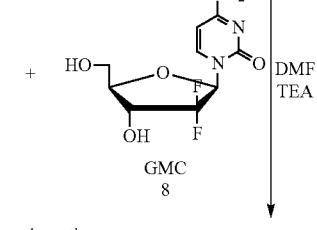
7      GMC
         8
DMF
TEA
1:1 molar ratio
one pot

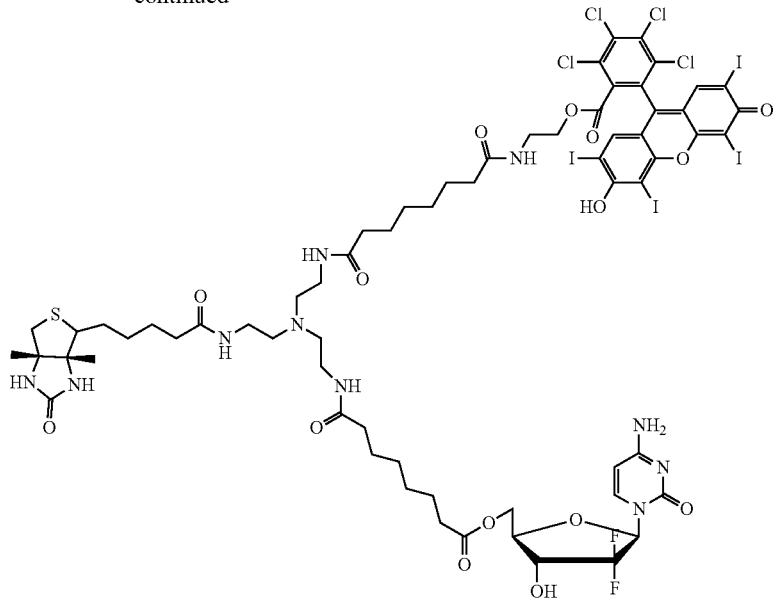

9

Synthesis of N-(2-(bis(2-aminoethyl)amino)ethyl)-5-(2-oxohexahydro-1H-thieno[3,4-d]imidazol-4-yl)pentanamide (3)

To a stirred solution of Biotin-NHS (0.5 g, 1.5 mmol) and TEA (catalytic amount) in anhydrous DMF (10 mL), a solution of tris(2-aminoethyl)amine (0.22 g, 1.5 mmol) in 5 mL of DMF was added. The reaction mixture was stirred at 0° C. under argon atmosphere. After 2 hr of stirring, another volume of TEA (catalytic amount) was added and the reaction mixture was allowed to stir overnight at room temperature. After completion of the reaction (by TLC), the excess DMF was removed under reduced pressure keeping the temperature below 45° C. and the white gummy liquid thus obtained was poured into excess diethyl ether (200 mL) and filtered. The crude product was purified by column chromatography on basic (TEA) silica gel (MeOH:DCM 1:9 to 3:7) to give 3 (0.33 g, 61% yield) as a white semi solid.

$^1$H NMR (DMSO-$d_6$): δ7.94 (brs, 1H, NH), 6.42 (brs, 1H, NH), 6.35 (brs, 1H, NH), 4.49 (brs, 4H, NH$_2$ X 2), 4.29 (s, 1H, CH), 4.12 (s, 1H, CH), 3.07-3.02 (m, 6H, CH$_2$ X 3), 2.88-2.82 (m, 1H, CH), 2.44-2.06 (m, 10H, CH$_2$ X 5), 1.59-1.48 (m, 4H, CH$_2$ X 2), 1.47-1.29 (m, 2H, CH$_2$).

ESI-MS: cald for $C_{16}H_{32}N_6O_2S$, 372.23; found 373.31 (M+H).

Synthesis of bis(2,5-dioxopyrrolidin-1-yl) 8,8'-((((2-(5-(2-oxohexahydro-1H-thieno[3,4-d]imidazol-4-yl)pentanamido)ethyl)azanediyl)bis(ethane-2,1-diyl))bis(azanediyl))bis(8-oxooctanoate) (5)

Compound 3 (0.5 g, 1.3 mmol) was dissolved in 10 mL anhydrous DMF in the presence of TEA (catalytic amount) and bis(2,5-dioxopyrrolidin-1-yl) octanedioate (4, 1 g, 2.7 mmol) was added. The reaction mixture was stirred at room temperature for 24 hrs under argon atmosphere. After completion of the reaction (by TLC), excess diethyl ether (200 mL) was added to the reaction mixture. The white precipitate thus obtained was filtered and washed three times with cold diethyl ether (50 mL×3). The crude product was purified by column chromatography on basic (TEA) silica gel (MeOH:CHCl$_3$ 2:8 to 5:5 v/v) to give 5 (0.83 g, 71% yield) as a low melting white solid.

$^1$H NMR (DMSO-$d_6$): δ7.94 (brs, 2H, NH X 2), 7.67 (brs, 1H, NH), 6.41 (brs, 1H, NH), 6.34 (brs, 1H, NH), 4.29 (s, 1H, CH), 4.12 (s, 1H, CH), 3.06-3.04 (m, 3H, CH and CH$_2$), 2.88-2.72 (m, 6H, CH$_2$ X 3), 2.71-2.63 (m, 8H, CH$_2$ X 4), 2.45-2.34 (m, 6H, CH$_2$ X 3), 2.20-2.06 (m, 10H, CH$_2$ X 5), 1.60-1.21 (m, 22H, CH$_2$ X 11). $^{13}$C NMR (DMSO-$d_6$): 172.5 (C=O), 170.7 (C=O), 163.1 (C=O), 162.7 (C=O), 61.4 (CH), 59.6 (CH), 55.8 (CH$_2$), 53.9 (NCH$_2$), 39.9 (CH$_2$), 39.8 (CH$_2$), 39.6 (CH$_2$), 37.3 (CH$_2$), 36.2 (CH$_2$), 35.6 (CH$_2$), 31.2 (CH$_2$), 28.7 (CH$_2$), 28.5 (CH$_2$), 25.8 (CH$_2$), 25.7 (CH$_2$), 25.6 (CH$_2$).

ESI-MS: cald for $C_{40}H_{62}N_8O_{12}S$, 878.4; found 901.3 (M+Na salt).

Synthesis of ((2R,3R, 5R)-5-(4-amino-2-oxopyrimidin-1 (2H)-yl)-4,4-difluoro-3-hydroxytetrahydrofuran-2-yl)methyl 4,11,19-trioxo-15-(2-(5-(2-oxohexahydro-1H-thieno[3,4-d]imidazol-4-yl)pentanamido)ethyl)-1-((2,3,4,5-tetrachloro-6-(6-hydroxy-2,4,5,7-tetraiodo-3-oxo-3H-xanthen-9-yl)benzoyl)oxy)-3,12,15,18-tetraazahexacosan-26-oate (9)

To a DMF (anhydrous, 10 mL) solution of 5 (0.4 g, 0.45 mmol) GMC-hydrochloride (8, 0.136 g, 0.45 mmol) and TEA (0.5 mL) were added at 0° C. and stirred for 24 hrs at room temperature under argon atmosphere. After completion of the reaction (monitored by GC-MS), Rose Bengal amine 7 (prepared according to McEwan et al. J. Control Release. 2015; 203, 51-56), (0.43 g, 0.45 mmol in DMF (5 mL)) and TEA (0.5 mL) were added to the reaction mixture and continued to stir for 24 hr. The progress of the reaction was monitored by mass spec analysis of the crude reaction mixture. After completion of the reaction, excess diethyl ether (200 mL) was added to the solution and stirred for 30 min. The pink red precipitate thus obtained was filtered and washes several times with cold diethyl ether (100 mL), ethyl acetate (100 mL), acetone-water mixture (10%, v/v, 100 mL) and finally with ethyl acetate-hexane mixture (50%, v/v, 100 ml) respectively to afford a pink red powder of compound 9 (0.26 g, 30% yield).

$^1$H NMR (DMSO-d$_6$): δ7.95 (brs, 2H, NH$_2$), 7.69 (s, 1H, CH, aromatic proton), 7.68 (s, 1H, CH, aromatic proton), 7.37 (s, 1H, CH), 7.32 (brs, 4H, NH X 4), 6.89 (s, 1H, CH), 6.42 (brs, 1H, NH), 6.35 (brs, 1H, NH), 6.22 (d, J=5.5 Hz, 1H, CH), 6.13 (brs, 1H, NH), 5.78-5.77 (m, 1H, CH), 5.19 (s, 1H, CH X 2), 4.9 (brs, 1H, OH), 4.30 (s, 2H, —OCH$_2$), 4.13 (s, 2H, —OCH$_2$), 3.79-3.60 (m, 3H, CH, CH$_2$), 3.39-3.32 (m, 2H, CH$_2$), 3.07 (brs, 6H, N—NHCH$_2$3), 2.94-2.84 (m, 6H, NCH$_2$ X 3), 2.81 (brs, 1H, OH), 2.45-2.46 (m, 3H, CH, CH$_2$), 2.17-2.06 (m, 10H, CH$_2$ X 5), 1.60-1.10 (m, 22H, CH$_2$ X 11).

$^{13}$C NMR (DMSO-d$_6$): 171.8 (C=O, C), 165.98 (C=O), 163.2 (C=O), 162.7 (C=O), 159.3 (CH), 155.0 (C=O), 150.5 (C), 145.8 (C), 141.2 (CH), 131.0 (C), 128.7 (C), 123.5 (C), 116.2 (C), 95.0 (CH), 80.9 (C), 69.3 (CH), 61.5 (C), 59.6 (CH$_2$), 59.4 (CH), 55.8 (CH), 51.7 (CH$_2$), 45.8 (CH$_2$), 40.2 (CH$_2$), 37.3 (CH$_2$), 37.05 (CH$_2$), 36.2 (CH$_2$), 35.5 (CH$_2$), 31.0 (CH$_2$), 28.7 (CH$_2$), 28.5 (CH$_2$), 28.2 (CH$_2$), 25.6 (CH$_2$).

ESI-MS: cald for C$_{63}$H$_{72}$Cl$_4$F$_2$I$_4$N$_{10}$O$_{15}$S, 1925.98; found 1925.90 (M–H).

EXAMPLE 2

Preparation, Stability and Loading Efficiency of Avidin-Functionalised Paclitaxel (PTX) Loaded Microbubbles (MBs)

2.1 Preparation of Lipid Stabilised MBs with PTX Incorporated within the Shell (PTX-MB)

Avidin functionalised lipid stabilised microbubbles with PTX hydrophobically incorporated in the shell were prepared by first dissolving the lipids 1,2-dibehenoyl-sn-glycero-3-phosphocholine (DBPC) (4.0 mg, 4.43 umol), 1,2-distearoyl-sn-glycero-3-phosphoethanolamine-N-[methoxy (polyethylene glycol)-2000] (DSPE-PEG(2000)) (1.35 mg, 0.481 μmol) and DSPE-PEG (2000)-biotin (1.45 mg, 0.481 μmol) in chloroform to achieve a molar ratio of 82:9:9. To this solution was added paclitaxel (5 mg, 5.86 μmol) dissolved in chloroform. The solution was heated at 40° C. for 30 minutes until the chloroform had evaporated. The dried lipid film was reconstituted in 3 mL of Ungers solution (PBS, Glycerol, Propylene glycol (8:1:1 volume ratio)) and heated on a water bath at 75° C. for 30 minutes. The suspension was then sonicated using a Microson ultrasonic cell disrupter at an amplitude of 22% for 1 minute to fully incorporate the lipids with paclitaxel. The suspension was then sparged with PFB gas whilst sonicating the suspension at an amplitude of 89% for 1 min to form the microbubble suspension. The MBs were then cooled on ice for 10 minutes followed by centrifugation at 700 rpm for 5 min to remove the excess lipids/paclitaxel present in the liquid below the bubble cake. The cake was then washed with 2 mL of Ungers solution followed by the addition of an aqueous solution of avidin (500 μL, 2.5 mg/mL). The suspension was then stirred for 5 min followed by centrifugation (700 rpm) to remove excess avidin. The MB cake was then washed again with 2 mL of Ungers solution, centrifuged (700 rpm) and the MBs isolated.

2.2 Loading of Biotin-RB, Biotin-Gem and Biotin-Gem-RB onto the Surface of Avidin Functionalised PTX-MBs A solution containing either Biotin-RB, Biotin-Gem, or Biotin-Gem-RB (500 μL, 5 mg/mL), prepared in a DMSO: Ungers solution (10:90 v/v) was added to 2 mL of PTX-MBs (2.0×10$^8$ MB/mL). The suspension was then mixed for 5 min using a rotary shaker followed by centrifugation (700 rpm) for 5 min to remove excess ligand. This coupling process was repeated one more time. The final microbubble cake was suspended in 2 mL of Ungers solution. The microbubbles were either used directly or oxygenated by sparging the suspension with oxygen gas for 2 min immediately prior to use.

2.3 Loading Capability of Avidin Functionalised PTX-MBs

To determine if the loading capacity of the avidin functionalised MBs was affected by the incorporation of PTX in the shell of the MB, three batches of PTX-MB were prepared using 0 mg, 2.5 mg or 5 mg of PTX during the MB manufacture process described in section 2.1. Each batch of MBs was then loaded with biotin-RB as described in section 2.2. The amount of Rose Bengal loaded on the surface of the MBs was then quantified using UV-Vis spectroscopy by purposely bursting a fixed amount of MBs and using a reference calibration curve. Each reaction was performed in triplicate. The reason biotin-RB was selected for use in this study was due to its inherent chromophore that made the quantification process more straight-forward.

Figure 1:
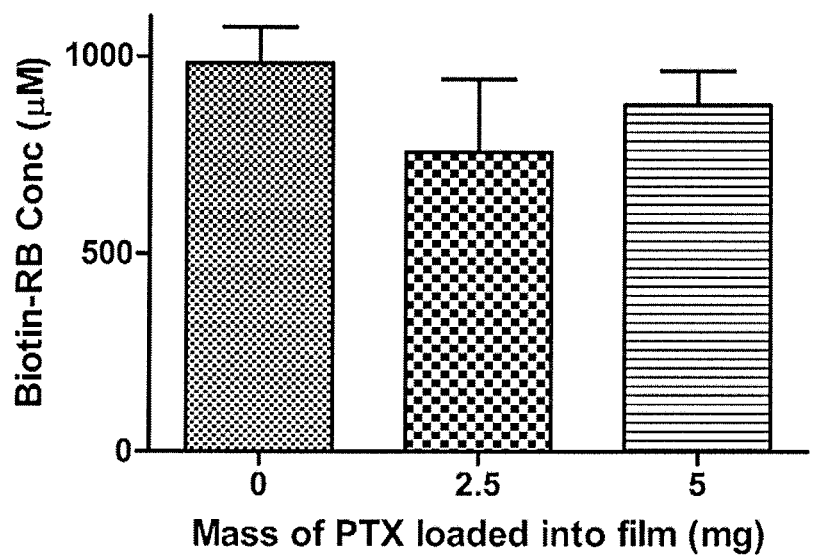
FIG. 1 shows the amount of Biotin-RB loaded onto the surface of MBs prepared using 0, 2.5 mg or 5 mg of paclitaxel (PTX).

The results from this study are shown in FIG. 1 and reveal no statistically significant difference in the loading of biotin-RB for any of the batches prepared.

These results indicate that the presence of PTX in the shell of the MBs does not affect the amount of biotinylated ligand attached to the surface.

2.4 Stability Determination of PTX-MBs

To determine the stability of PTX-MBs with a biotinylated payload attached to their surface, three batches of PTX-MB-RB MBs containing either 0, 2.5 or 5.0 mg PTX in the shell were prepared as described in section 2.3. Samples of the microbubbles (2 mL) from each batch were incubated at 37° C. for 3 hours and the MB number then counted at various time intervals (0 min, 10 min, 60 min, 120 min, and 180 min) using a haemocytometer.

Figure 2:
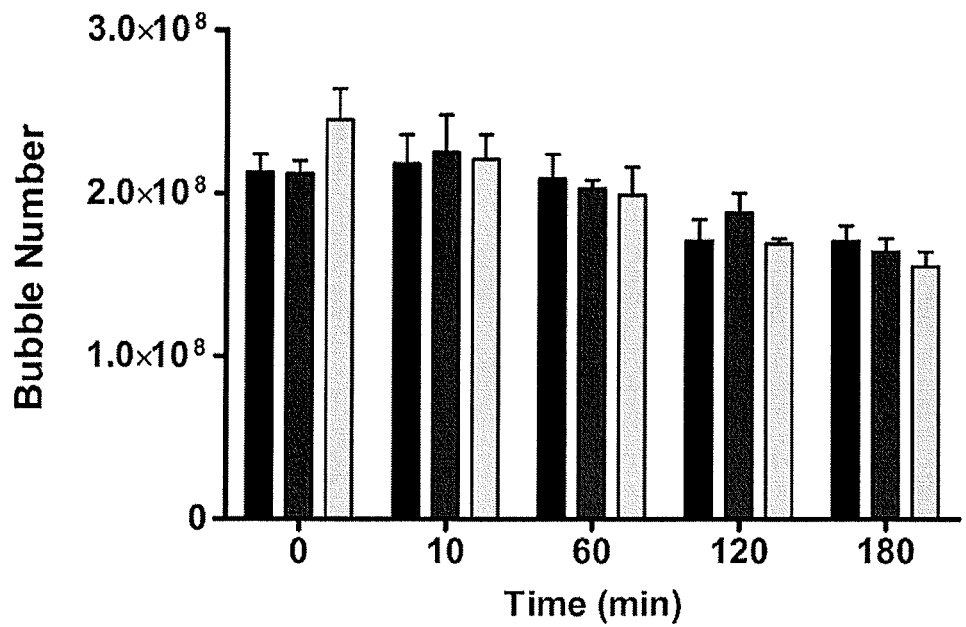
FIG. 2 shows a plot of MB number against time for three batches of MB-RB prepared using 0 mg (black bar), 2.5 mg (dark bar) or 5 mg of paclitaxel (PTX) (light grey).

The results from this study are shown in FIG. 2 and reveal no statistically significant difference in the MB number for either batch of PTX-MB-RB prepared. These results indicate that the stability of the PTX-MB-RB conjugates is unaffected by the presence of PTX in the shell of the MB.

EXAMPLE 3

Biological Testing of PTX-MB-RB, PTX-MB-Gem and PTX-MB-Gem-RB 3.1 Efficacy of Biotin-Gem and Biotin-Gem-RB in BxPC-3 Cells To ensure the antimetabolite efficacy of Biotin-Gem and Biotin-Gem-RB were unaffected by chemical modification, the cytotoxicity of the conjugates was determined in the human pancreatic adenocarcinoma cell line BxPc-3. Cells were maintained in RPMI-1640 which was supplemented with 10% (v/v) foetal bovine serum in a humidified 5% $CO_2$ atmosphere at 37° C. These cells were seeded into 96 well plates at a density of 5000 cells per well. The plates were then incubated for 24 hours followed by the addition of 100 uL of media spiked with either Gem, Biotin-Gem or Biotin-Gem-RB. The concentrations used for Biotin-Gem were 0, 0.1, 5, 10, 25, 50, 100 and 100 μM while for Biotin-Gem-RB, concentrations of 0.01 μM, 0.05 μM, 0.1 μM, 0.5 μM, 1 μM, 5 μM and 10 μM were investigated. Corresponding concentrations of Gem were used in each case. The cells were then further incubated for 48 hours before cell viability was determined using an MTT assay.

Figure 3:
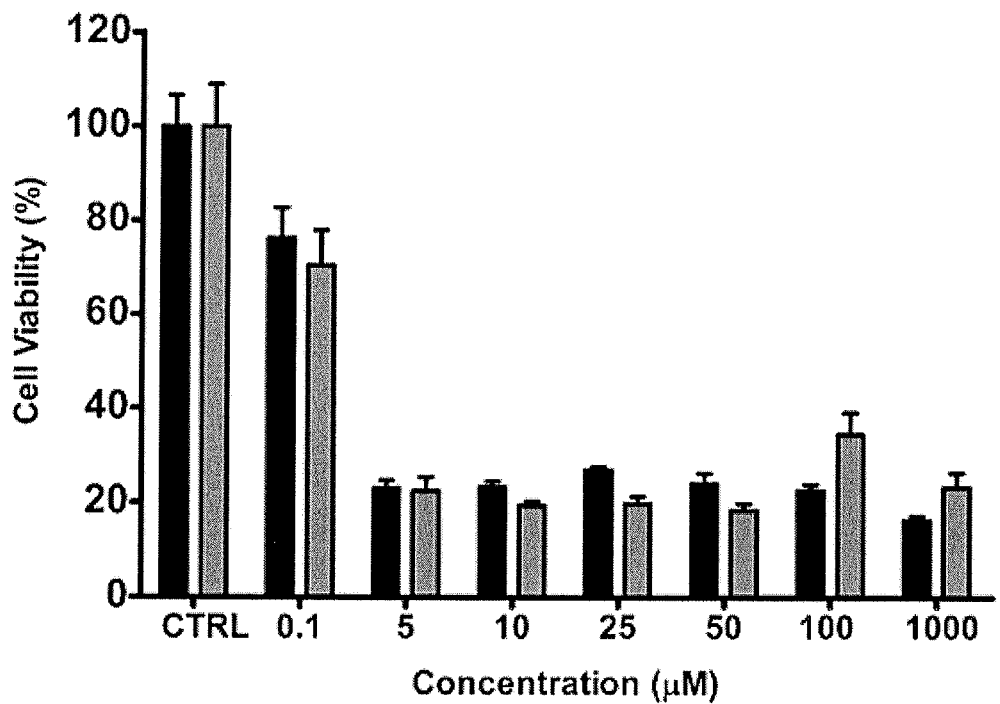
FIG. 3 shows a plot of cell viability for BxPC-3 cells treated with Gemcitabine (black) or Biotin-Gem (grey). Cell viability determined by MTT assay 48 h after incubation.
Figure 4:
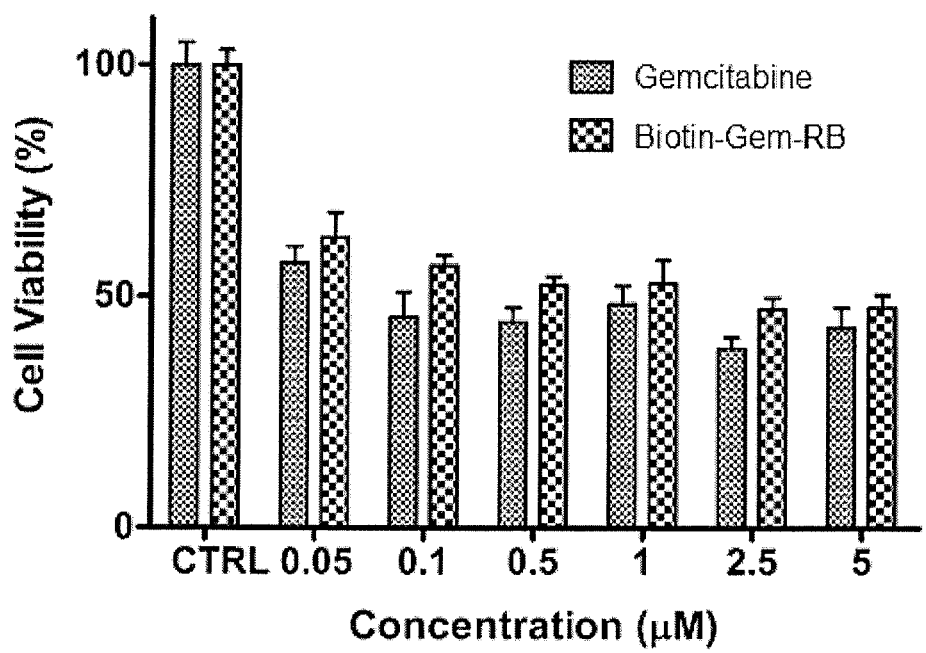
FIG. 4 shows a plot of cell viability for BxPC-3 cells treated with Gemcitabine or Biotin-Gem-RB. Cell viability determined by MTT assay 48 h after incubation.

The results from this study are shown in FIGS. 3 and 4 and reveal no statistically significant difference in efficacy for Gemcitabine compared to Biotin-Gem or Biotin-Gem-RB over the concentration ranges tested. These results indicate that chemical modification of Gemcitabine in each of these ligands does not negatively impact its efficacy.

3.2 In Vivo Efficacy of Combined Paclitaxel/Gemcitabine/SDT Treatment Delivered Using PTX-MB-Gem-RB MIA-Paca-2 cells were maintained in DMEM medium supplemented with 10% foetal calf serum and 1% penstrep in a humidified 5% $CO_2$ atmosphere at 37° C. Cells ($5\times10^6$) were re-suspended in Matrigel® and implanted subcutaneously into the rear dorsum of BALB/c SCID mice. All animals were treated humanely and in accordance with licensed procedures under the UK Animals (Scientific Procedures) Act, 1986. Once the tumours had reached an average volume of 150 mm³ animals were randomly assigned into 4 treatment groups (n=4 in each group). Animals were anaesthetised by intraperitoneal injection of Hypnorm:hypnovel:ice cold sterile water (1:2:1). Animals were treated with a 100 μL suspension containing either PTX-MB-RB ([PTX]=878 μM; [RB]=1179 μM), PTX-MB-Gem ([PTX]=846 μM; [Gem]=850 μM) or PTX-MB-Gem-RB ([PTX]=742 μM; [Gem]=489 μM; [RB]=489 μM) by intravenous injection into the tail vein. Ultrasound was applied directly to the tumour area using ultrasound gel to mediate contact during and for 3 min following injection at an ultrasound frequency of 1 MHz, an ultrasound power density of 3.5 Wcm$^{-1}$ and a duty cycle of 30% for 3.5 min. For the PTX-MB-RB and PTX-MB-Gem-RB groups, a second ultrasound treatment using the same parameters was also applied directly to the tumours after 30 min after injection. Treatments were administered on Days 0, 1, and 2. Tumour growth was monitored daily throughout the course of the treatment using callipers and tumour volume calculated using the equation: tumour volume=(W*H*L/2).

The results are shown in FIG. 5 and reveal a statistically significant reduction (p<0.001) in tumour growth for all treatment groups relative to the control. There was no significant difference in tumour growth for combined Paclitaxel-SDT (PTX-MB-RB) group compared to combined Paclitaxel-Gemcitabine (PTX-MB-Gem) treatment. However, there was a statistically significant difference in tumour growth (p<0.01) for combined Paclitaxel-Gemcitabine-SDT (PTX-MB-Gem-RB) treatment when compared to either combined Paclitaxel-SDT (PTX-MB-RB) or combined Paclitaxel-Gemcitabine (PTX-MB-Gem) treatment.

EXAMPLE 4

Preparation, Characterisation and Biological Testing of Avidin Functionalised PTX-MBs Carrying Biotin-RB, Biotin-Gem and Biotin-Gem-RB

4.1 Loading of Biotin-RB, Biotin-Gem and Biotin-Gem-RB onto the Surface of Avidin Functionalised PTX-MBs A saturated aqueous solution containing either Biotin-RB, Biotin-Gem or Biotin-Gem-RB (1 mL, 5 mg/mL) was added to 2 mL of PTX-MBs or PTX-free MBs ($6.72\times10^8$ MB/mL). The suspension was mixed for 5 min (0° C.) followed by centrifugation (700 rpm) for 3 min to remove excess ligand. The MB cake was then washed a further 3 times with PBS solution. The final microbubble cake was suspended in 2 mL of PBS solution. The microbubbles were either used directly or oxygenated by sparging the suspension with oxygen gas for 2 min immediately prior to use. The final microbubble number was determined on a haemocytometer using an optical microscope. A schematic representation of the PTX/GEM/RB-MB is shown in FIG. 6.

4.2 Size Distribution Analysis of MB Formulation

Size distribution analysis was carried out using imageJ software. The bright field image was converted to 8-bit greyscale before an automated threshold strategy was applied to eliminate out of focus MBs. Particle diameter was then calculated relative to the scale bar present in the bright field image. FIG. 7 shows the size distribution histogram constructed from the image. The average microbubble diameter was 1.54 m.

4.3 In Vitro Efficacy

Human primary pancreatic adenocarcinoma cell lines BxPc-3, Panc-1 and Mia-PaCa-2 were maintained in RPMI 1640 medium which was supplemented with 100 U/mL penicillin, 100 mg/mL streptomycin, and 10% fetal bovine serum (FBS) and Dulbecco's Modified Eagle's Medium (DMEM) containing 1 g/L glucose and supplemented with 100 U/mL penicillin, 100 mg/mL streptomycin, and 10% fetal bovine serum (FBS) respectively in a humidified 5% $CO_2$ atmosphere at 37° C. These cells were seeded into 96 well plates at a density of 5000 cells per well. The plates were then incubated for 24 hours followed by the addition of 100 μL of media spiked with Gem or Biotin-Gem-RB at concentrations ranging from 0.001-1000 μM. The cells were then further incubated for 48 hours before cell viability was determined by an MTT assay.

FIG. 8 shows the comparative efficacy of biotin-GEM-RB with commercially available gemcitabine HCl in the three pancreatic cancer cell lines: Panc-1 (a) BxPc-3 (b) and Mia-PaCa-2 (c) over a wide range of concentrations (0-1000 μM). These results show that there is no decrease in efficacy following the modification of gemcitabine and there is also a significant increase in efficacy for Panc-1 cells above 10 μM.

4.4 Culture of Panc-1 Spheroids

The human primary pancreatic carcinoma cell line PANC-1 was maintained in Dulbecco's Modified Eagle's Medium (DMEM) containing 1 g/L glucose and supplemented with 100 U/mL penicillin, 100 mg/mL streptomycin, and 10% fetal bovine serum (FBS). Cells were incubated at 37° C. in a humidified atmosphere with 5% $CO_2$. Spheroids were prepared by seeding 2000 cells (200 uL) into a pre-coated 96-well plate (60 uL 1.5% agarose per well). Spheroids were inspected daily and took 3 days to reach a treatable size.

4.5 In Vitro Cytotoxicity in Panc-1 Spheroids

Panc-1 spheroids were cultured as described above. The media in each well was replaced with either fresh drug-free media, PTX-MB (5 uM), GEM/RB-MB (6.8 µM) or PTX/GEM/RB-MB (PTX—5 µM, GEM/RB—6.8 µM). Wells were then treated individually with ultrasound (Sonidel SP100 sonoporator, 30 s, frequency—1 MHz, ultrasound power density—3.0 $W/cm^2$, duty cycle—40%). Inspection of Panc-1 spheroids following 48-hour incubation with fresh media, GEM/RB MBs, PTX MBs and PTX/GEM/RB MBs, with and without ultrasound exposure, revealed a degradation in spheroid morphology in all groups treated with drug-loaded MBs following ultrasound exposure for 30 seconds.

4.6 Total Cell Viability Assay of Spheroids

Two days after initial treatment spheroids were washed as described above. A total of 5 spheroids/replicate from each condition was collected in an Eppendorf tube, washed with PBS and then incubated with trypsin for 15 min at 37° C. The resultant cellular suspension was then incubated for 3 hours with MTT (10 µl in 100 µl of media). The absorbance was then measured at 570-690 nm using FLUOstar Omega (BMG Labtech) plate reader.

Data is expressed as % of cell viability vs. untreated sample in FIG. 9. This shows a decrease in cell viability for all groups treated with MB formulations and a further decrease when these groups were treated with ultrasound for 30 sec. Spheroids treated with PTX/GEM/RB MBs+US performed the best with a decrease in cell viability of 67% compared with untreated controls.

4.7 Propidium Iodide Staining of Spheroids

Two days after initial treatment, Panc-1 spheroids were washed four times with PBS to remove excess drug and then incubated with a solution of PBS and Propidium Iodide (Invitrogen) with a final concentration of 100 µg/mL. Spheroids were then incubated at RT for 40 min. After incubation spheroids were washed with PBS before being placed onto a glass microscope slide at which point live images were collected using a NIKON Eclipse E400 Phase contrast microscope in bright field (BF) and in fluorescence to visualise Propidium Iodide signal using 540 nm band pass excitation and 590 nm long pass emission filters, respectively. Spheroids treated with all MB formulations displayed an increased fluorescence intensity at 617 nm, and hence an increased uptake of propidium iodide (PI). Spheroids treated with either GEM/RB MBs or PTX/GEM/RB MBs showed a further increase in fluorescence intensity with the latter performing the best. A further increase in fluorescence intensity was evident in groups exposed to ultrasound for 30 sec following treatment. FIG. 10 shows an increase in PI uptake for all groups treated with MB formulations and a further increase when these groups were treated with ultrasound for 30 sec. Spheroids treated with PTX/GEM/RB MBs+US performed the best.

4.8 In Vivo Cytotoxicity Experiments

Mia-Paca-2 cells were maintained in DMEM medium and BxPc-3 cells were maintained in RPMI 1640 both supplemented with 100 U/mL penicillin, 100 mg/mL streptomycin, and 10% fetal bovine serum (FBS) in a humidified 5% $CO_2$ atmosphere at 37° C. Cells ($5 \times 10^6$) were re-suspended in Matrigel® and implanted subcutaneously into the rear dorsum of SCID (C.B-17/IcrHan®Hsd-Prkdcscid) mice. Tumours reached treatable size within 3 weeks. Tumour measurements were taken daily using callipers. Once the tumours had reached an average volume of 150 $mm^3$ animals were randomly assigned into treatment groups. Animals were anaesthetised by intraperitoneal injection of hypnorm:hypnovel:ice cold sterile water for injection (1:2:1). Animals were treated with 100 µL of either $O_2$MB-GEM-RB, $O_2$MB-PTX-GEM-RB, Paclitaxel in cremophor EL by I.V. injection into the tail vein and gemcitabine hydrochloride by I.P. injection. Ultrasound was applied directly to the tumour immediately following injection at an ultrasound frequency of 1 MHz, an ultrasound power density of 3.5 $Wcm^{-1}$ and a duty cycle of 30% for 3.5 min. A second ultrasound treatment was applied directly to the tumour 30 min following. Tumour growth was monitored daily throughout the course of the treatment.

Gemcitabine hydrochloride was dissolved in sterile PBS and administered as a 100 uL I.P injection (120 mg/Kg). Ultrasound treatment was delivered for 3.5 minutes at frequency of 1 MHz, an ultrasound power density of 3.5 $W/cm^2$ and a duty cycle of 30% immediately after injection and 30 minutes following.

The plots in FIG. 11(*a*) show that mice treated with PTX/GEM/RB MBs followed by ultrasound exposure had a statistically significant reduction in tumour growth. Tumour growth was controlled continually within this group throughout the 10-day experiment. The response shown by this group also compared favourably with mice treated with a clinical dose of the current standard of therapy for pancreatic cancer (gemcitabine). FIG. 11(*b*) shows that mice treated with PTX/GEM/RB MBs showed no significant reduction in body weight when compared to untreated controls indicating that not only is the treatment efficacious but also well tolerated. In contrast, mice treated with the clinical dose of gemcitabine showed a significant decrease in body weight of 12% at day 6.

The plots in FIG. 12 show that mice treated with PTX/GEM/RB MBs followed by ultrasound exposure had a statistically significantly decrease in rate of tumour growth. Tumour growth was controlled continually within this group throughout the 10-day experiment. The response shown by this group also compared favourably with mice treated with a clinical dose of the current standard combination therapy for pancreatic cancer (gemcitabine+paclitaxel).

4.9 Determination of the Concentration of PTX and Biotin-Gem-RB and Loading Capacity of RB Three batches of PTX/RB MBs were prepared as described previously with 0, 2.5 or 5 mg of PTX added to the lipid film and with the same amount of biotin rose bengal added. After subsequent washing, the concentration of rose bengal was derived using standard UV spectrophotometry measuring at 550 nm. This experiment was done in triplicate. PTX concentration was determined by reverse phase HPLC using a Phenomenex $C_{18}$ column (250×4.6 mm, 5 µm), a mobile phase consisting of acetonitrile:water (1:1 v/v), and a detection wavelength of 227 nm. The retention time of the analyte was 9 min. The loading of Biotin-Gem-RB was determined using UV spectrophotometry with an analyte absorbance wavelength of 560 nm.

FIG. 13 shows the relative loading of biotin-RB as the concentration of paclitaxel increases from 0 to 5 mg. This shows that as the concentration of paclitaxel loaded within the acyl chains of the phospholipid shell increases, the relative loading capacity for biotin-RB does not significantly decrease.

4.10 Stability of PTX-MBs

PTX-MBs were prepared as described previously with 0, 2.5 or 5 mg of PTX added to the lipid film. After subsequent washing the MB number was determined using a haemocytometer on an optical microscope. An initial reading was taken immediately after MB synthesis and then 10, 60, 120 and 180 min following. PTX concentration was determined using reverse phase HPLC as described previously.

The results in FIG. 14 show that as the concentration of PTX within the acyl chains of the phospholipid MBs increase, the relative stability of the formulation does not significantly decrease.

EXAMPLE 5

Preparation and Biological Testing of Paclitaxel (PTX) Loaded Microbubbles (MBs) Carrying Biotin-Doxorubicin (Biotin-Dox) or Biotin-Rose Bengal (Biotin-RB) Conjugates

5.1 Reagents and Materials 1,2-dibehenoyl-sn-glycero-3-phosphocholine (DBPC) and 1,2-distearoyl-sn-glycero-3-phosphoethanolamine-N-[methoxy(polyethylene glycol)-2000] (DSPE-PEG(2000)) and DSPE-PEG(2000)-biotin were purchased from Avanti Polar Lipids (Alabaster, Alabama, USA). Oxygen gas was purchased from BOC Industrial Gases UK and perfluorobutane (PFB) was purchased from Apollo Scientific Ltd. Phosophate Buffered Saline (PBS) was purchased from Gibco, Life Technologies, UK. Glycerol and propylene glycol (1 kg, hydrolysed) were purchased from Sigma Aldrich (UK). Optical microscope images were obtained using a Leica DM500 optical microscope. Rose Bengal sodium salt, NHS-biotin, gemcitabine, MTT assay kit, avidin, chloroacetic acid, 4-dimethylaminopyridine (DMAP), hydroxybenzotriazole (HOBt), N,N'-dicyclohexylcarbodiimide (DCC), anhydrous dimethylformamide (DMF), and ethanol were purchased from Sigma Aldrich (UK) at the highest grade possible. Biotin, di(N-succinimidyl) carbonate and 2-aminoethanol were purchased from Tokyo Chemical Industry UK Ltd.

5.2 Synthesis of Biotin-Dox

Biotinylated Doxorubicin (Biotin-Dox) (3) was synthesised according to scheme 3. The protocol is provided below.

Scheme 3: Synthetic scheme for the synthesis of Biotin-Dox

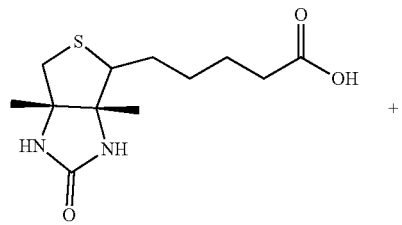

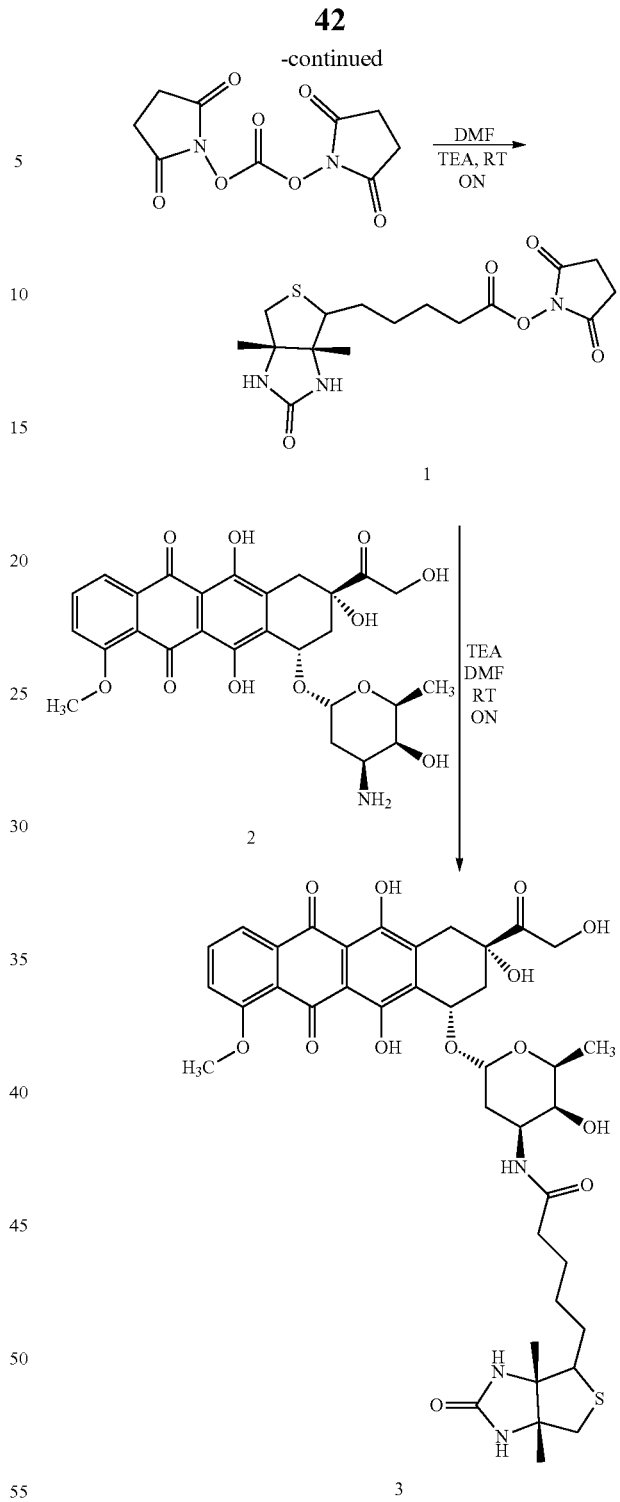

To an ice cold solution of biotin-N-hydroxysuccinimide ester (1, 0.14 g, 0.41 mmmol) in DMF (10 ml) was added doxorubicin (2, 0.3 g, 0.41 mmol) under nitrogen atmosphere. After stirring for 30 min, triethylamine (0.5 ml, 2 mmol) was added to this reaction mixture and was allowed to stir for another 12 hrs at room temperature. The reaction was monitored by TLC (Merck Silica 60, HF 254, 20:80 methanol-dichloromethane v/v). After completion of the reaction, excess diethyl ether (100 ml) was added to the reaction mixture. The red solid thus obtained was filtered and washed three times with diethyl ether (50 ml×3). This red solid was then subjected to PTLC purification using methanol-dichloromethane (20:80, v/v) as an eluent to obtain 0.25 g (Yield=78%) of 3. An analytical sample was obtained from a recrystallization of this product from ethanol.

$^1$H NMR (DMSO-$d_6$) δ:7.84 (d, J=7.5 Hz, 2H, aromatic), 7.58 (d, J=7.5 Hz, 1H, aromatic), 6.36 (s, 1H, NH), 6.29 (s, 1H, NH), 5.37 (brs, 1H, OH), 5.22 (brs, 1H, OH), 4.87 (s, 2H, —CH$_2$—OH), 4.51 (brs, 2H, OH X2), 4.36-4.33 (m, 1H, CH), 4.25-4.22 (m, 1H, CH), 4.16-4.13 (m, 1H, CH), 3.99 (s, 3H, OCH$_3$), 3.60-3.58 (m, 1H, CH), 3.55 (brs, 2H, OH X2), 3.10-3.00 (m, 4H, CH$_2$ X1, CH X2), 2.88-2.54 (m, 3H, CH$_2$ X 1, CH), 2.20-2.00 (m, 1H, CH), 1.63-1.50 (m, 4H, CH$_2$ X 2), 1.42-1.22 (m, 11H, CH$_3$ X 1, CH$_2$X 4). $^{13}$CNMR (DMSO-$d_6$): 177.6, 176.9, 174.8, 166.4, 163.0, 161.2, 153.7, 152.7, 137.4, 132.4, 120.4, 119.4, 99.5, 97.8, 80.15, 75.1, 72.7, 66.4, 61.4, 59.5, 55.7, 47.8, 33.8, 31.9, 28.9, 28.8, 28.5, 28.4, 24.9, 19.8, 17.6, 17.1.

ESMS (M-H]: calculated for $C_{37}H_{43}I_2N_3O_{13}S$=769.25, found=767.9.

5.3 Preparation of Oxygen Carrying Microbubbles Loaded with PTX in the Shell and Either Biotin-Dox or Biotin-RB Attached to the MB Surface Avidin-functionalised lipid-stabilised microbubbles with PTX hydrophobically incorporated in the shell were prepared by dissolving 1,2-dibehenoyl-sn-glycero-3-phosphocholine (DBPC) (4.0 mg, 4.44 umol), 1,2-distearoyl-sn-glycero-3-phosphoethanolamine-N-[methoxy(polyethylene glycol)-2000] (DSPE-PEG(2000)) (1.35 mg, 0.481 umol) and DSPE-PEG (2000)-biotin (1.45 mg, 0.481 umol) in chloroform to achieve a molar ratio of 82:9:9. To this solution was added paclitaxel (5 mg, 5.86 µmol) dissolved in chloroform (100 uL). The solvent was removed under vacuum at room temperature yielding a translucent film. The dried lipid film was reconstituted in 2 mL of a solution containing PBS, Glycerol and Proplyene glycol (8:1:1 volume ratio) and heated in a water bath at 80° C. for 30 minutes. The suspension was then sonicated using a Microson ultrasonic cell disrupter at an amplitude of 22% for 30 seconds to fully suspend paclitaxel. The suspension was then sparged with PFB gas whilst sonicating the suspension at an amplitude of 89% for 1 minute to form the microbubbles. The MBs were then cooled on ice for 10 minutes followed by centrifugation at 700 rpm for 3 min and removal of the subnatant to remove the excess lipids/paclitaxel. The cake was then washed a further 2 times before an aqueous solution of avidin (10 mg/mL) was added. The suspension was then stirred for 5 min (0° C.) followed by centrifugation (700 rpm) to remove unbound avidin. The MB cake was then washed again and suspended in PBS solution. A saturated aqueous solution containing either Biotin-Dox or biotin-RB (1 mL, 5 mg/mL) was added to 2 mL of PTX-MBs (7.52×10$^8$ MB/mL). The suspension was mixed for 5 min (0° C.) followed by centrifugation (700 rpm) for 3 min to remove excess ligand. The MB cake was then washed a further 3 times with PBS solution. The final microbubble cake was suspended in 2 mL of PBS solution. The microbubbles were oxygenated by sparging the suspension with oxygen gas for 2 min immediately prior to use. The final microbubble number was determined on a haemocytometer using an optical microscope. FIG. 15 is a schematic representation of a) O$_2$MB-PTX/DOX b) O$_2$MB-PTX/RB.

5.4 Colony Forming Assay to Determine the Cytotoxicity of Dox, PTX, SDT and Combinations of Each in MCF-7 Cells In this study, the concentration of each individual drug used was intentionally sub-lethal, so that any benefit obtained by the combination treatment could easily be identified. In addition, as the action of ultrasound can influence the cellular uptake of drugs as a result of sonoporation, cells treated with Dox or PTX were also exposed to ultrasound, to control for any potential ultrasound mediated effects on cell viability as a result of sonoporation. Following treatment, cell viability was determined using a colony forming assay.

MCF-7 cells were seeded (5×10$^3$) in a 96 well plate, 24 hours later cells were treated with free drug as a single treatment of PTX (1 nM), Dox (10 nM), RB (10 nM) or combination treatment for 3 hours followed by media replacement. Selected wells were treated with ultrasound delivered using a Sonidel SP100 sonoporator (1 MHz, 30 seconds, 3 Wcm$^{-2}$, duty cycle=50%, and PRF=100 Hz). The following day cells were pooled from 2 wells and seeded in a 6 well plate. Plates were placed in an incubator for 7 days. Media was removed from wells, fixation/staining solution was added at room temperature for 20 minutes. Fixative/staining solution contained: 0.5 g crystal violet (0.05%), 27 ml 37% formaldehyde, 100 ml 10×PBS (X1), 10 mL methanol (1%) and 863 mL of distilled water. Solution was removed and washed under running water. Pictures were taking using a high-resolution camera and colony formation was analysed via Image J.

The results are shown in FIG. 16 and reveal no reduction in colony formation for cells treated with a combination of PTX, Dox and Rose Bengal (drug combo) in the absence of ultrasound compared to untreated cells. Treatment of cells with PTX+US, RB+US (i.e. SDT) or Dox+US reduced colony number by 7.3, 18.8 and 29.3% respectively compared to untreated cells, while cells treated with combined PTX, Dox and RB+US reduced in colony number by 44.0%. The lack of efficacy for the combined drug cocktail in the absence of US was not surprising as sub-lethal doses of the drugs were used. However, the significant improvement in efficacy following exposure to US suggests sonoporation effects improve the uptake of these drugs enabling a cytotoxic effect to be observed. The fact that the greatest reduction in cell viability was observed for the combined PTX, Dox and SDT treatment group indicates that these three treatments complement each other and improve the cytotoxic effect observed.

5.5 Preparation of MCF-7 Spheroids

The human breast cancer MCF-7 cell line was purchased from American Type Culture Collection (ATCC, Rockville, MD, USA). MCF-7 cells were cultured in DMEM medium supplemented with 10% FBS (Gibco), 100 µg/ml streptomycin (Gibco) and maintained in a humidified 5% CO$_2$ atmosphere at 37° C. 3D spheroids were generated by growing MCF-7 cells in Carrier Plate (ULA) from PerkinElmer. Briefly, 8000 MCF-7 were seeded in 100 µl of media in each well. 24 h after the seeding, 100 µl of media was added to each well and plates were incubated at 37° C. with 5% CO$_2$ for 3 days to allow cell assembly. Media was changed every 3-4 days by removing 100 μl of old media and replacing it with 100 μl of fresh media.

5.6 Chemo-Sonodynamic Therapy Treatment of MCF-7 Spheroids Using MB-PTX-Dox MB-PTX-RB±Ultrasound After 3 days of incubation, spheroids were divided into groups and treated according to the following conditions: untreated spheroids, spheroids treated only with MB (no drugs), spheroids treated with PTX/Dox only (i.e. no MB) ([PTX]=0.34 μM, [DOX]=1 μM), spheroids treated with a PTX-MB-Dox/PTX-MB-RB ([DOX]=1 μM, [RB]=10 μM). Where required, individual wells were then placed in direct contact with the emitting surface a Sonidel SP100 sonoporator with ultrasound gel used to mediate contact. Each well was treated with ultrasound (US) for 30 s, using a frequency of 1 MHz, an US power density of 3.0 W/cm$^2$ and a duty cycle of 50% (pulse frequency=100 Hz). At the end of each treatment plates were placed in incubator in a humidified 5% $CO_2$ atmosphere at 37° C. for 3 h and then wells washed three times and fresh media added. An MTT assay (APPLICHEM LIFESCIENCE) was used to determine cell viability 48 h after the treatment. Briefly, five spheroids/replicate from each condition were collected in an Eppendorf tube, washed with PBS and then incubated with trypsin for 15 min at 37° C. The resultant cellular suspension was then incubated for 3 h with MTT (10 μl n 100 μl of media). The absorbance was then measured at 570-690 nm using FLUOstar Omega (BMG Labtech) plate reader. Data is expressed as % of cell viability vs. untreated sample.

Moreover, at the end of each treatment, Propidium Iodide (PI) staining was performed in order to investigate cellular damage on spheroid crown. Briefly, spheroids were washed four times with PBS to remove excess of media and then incubated with a solution of PBS and PI (Invitrogen) with a final concentration of 100 μg/ml. Spheroids were then incubated in the dark at RT for 40 min. At the end of incubation, spheroids were washed three times with PBS, to remove the excess of PI, and then live images were collected using a NIKON Eclipse E400 Phase contrast microscope in bright field and in fluorescence to see PI using 540 nm band pass excitation and 590 nm long pass emission filters, respectively. Moreover, fluorescence signal was evaluated with NIS-Elements BR 3.2 Imaging software, considering a total of 3 different spheroids per condition. Image J software was used to quantify PI fluorescence, expresses as % of PI fluorescence/μm$^2$. Furthermore, in order to investigate the effect of each treatment on spheroid morphology, volume was calculated for each spheroid by using the formula: volume=$4/3\pi r^3$.

As shown in FIG. 17, a statistically significant reduction of cells viability (p<0.05) was observed when 3D MCF-7 spheroids were exposed only to US treatment, or previously exposed to MB only or to PTX/Dox and then exposed to US. However, an increased reduction in cell viability was observed when MCF-7 3D spheroids were treated with a combination of PTX-MB-Dox/PTX-MB-Dox and then exposed to US (p<0.001), compared to spheroids treated only with PTX-MB-Dox/PTX-MB-Dox (p<0.001) and compared to spheroids treated with free drugs, i.e. PTX/Dox, and then exposed to US (p<0.01).

Results from the P.I. staining experiments revealed a slightly different trend from those observed in the MTT assay. P.I. is a DNA selective permeable dye that passes freely through the compromised plasma membranes of dead cells but does not permeate the membrane of living cells. In contrast to the MTT assay experiments, where a single cell suspension of the spheroid was analysed post-treatment, intact spheroids were examined following P.I staining. The bright field and fluorescent images from each treatment group were recorded with the fluorescence intensity quantified and plotted in FIG. 18. Bright red P.I. fluorescence was observed for spheroids treated with the $O_2$MB-PTX-Dox/$O_2$MB-PTX-RB+US group which was significantly more intense than any of the other groups. Surprisingly and in contrast to results from the MTT assay, the P.I. fluorescence intensity from the $O_2$MB-PTX-Dox/$O_2$MB-PTX-RB group in the absence of US was significantly more intense than that for the PTX/Dox+US group. It was also noticeable that the mean volume of spheroids treated with O2MB-PTX-Dox/O2MB-PTX-RB+US was significantly smaller than in any of the other groups including those spheroids treated with O2MB-PTX-Dox/O2MB-PTX-RB in the absence of US. Combined, the intense P.I. fluorescence and size reduction observed for spheroids treated with MB mediated chemosonodynamic therapy, in addition to the reduced cell viability observed from the MTT assay experiments, highlight the effectiveness of this approach in this particular model of breast cancer.

5.7 Cytotoxicity of Chemo-Sonodynamic Therapy In Vivo Using $O_2$MB-PTX-Dox/O2MB-PTX-RB±Ultrasound Subcutaneous MCF-7 tumours were established in recipient mice and a mixed suspension of the $O_2$MB-PTX-Dox/$O_2$MB-PTX-RB formulations administered by IV injection. During injection, ultrasound was positioned at the tumour to disrupt the MBs, release the payloads and activate SDT, where appropriate. To fully evaluate the effectiveness of the MB delivered treatments, a group of animals were also treated with a combination of free PTX/Dox (i.e. no MB attached).

All animals employed in this study were treated in accordance with the licenced procedures under the UK Animals (Scientific Procedures) Act 1986. Mia PaCa-2 cells (5×10$^6$) in 100 μL Matrigel were sub-cutaneously implanted into the rear dorsum of SCID (CB17/Icr-Prkdcscid/IcrIcoCrl) mice. Tumours started to form approximately 1-2 weeks after cell implantation. Once the tumour became palpable, dimensions were measured using Vernier callipers. Tumour volume was calculated using the equation tumour volume=(length×width×width)/2. Once tumours reached approximately 65 mm$^3$±4.20 animals were grouped and treatment commenced. Group 1 was untreated, group 2 a mixed suspension (50 μL) of $O_2$MB-PTX/RB and $O_2$MB-PTX/Dox delivered by IV with US applied to the tumour during injection. Group 3 received the same MB treatment as group 2 but without US. Group 4 received $O_2$MB-PTX/Dox delivered by IV with US applied to the tumour during injection and group 5 a cremaphor solution containing free PTX and DOX. Ultrasound was delivered using a Sonidel SP100 sonoporator (3.5 Wcm$^{-2}$, 1 MHz, 30% duty cycle, and PRF=100 Hz; PNP=0.48 MPa; MI=0.48) during and after injection (for a total of 3.5 min) with a second 3.5 min ultrasound exposure 30 min following injection. Treatments, tumour measurements and body weights were carried out and recorded once per week.

The tumour growth delay plot is shown in FIG. 19 and reveals a significant reduction in tumour volume for animals treated with PTX-MB-Dox/PTX-MB-RB+US, with tumours being 6.96% smaller when compared to their pre-treatment size, 25 days after the initial treatment. In contrast, tumours in animals treated with the same PTX-MB-Dox/PTX-MB-RB formulation in the absence of ultrasound grew by 43.15% over the same time period. These results suggest that Ultrasound Targeted Microbubble Destruction (UTMD) enables a greater proportion of drugs to be localised in the tumour yielding a significantly improved therapeutic effect. Indeed, the effect of PTX-MB-Dox/PTX-MB-RB+US was also significantly better that observed following treatment using the free PTX/Dox combination which grew by 24.77% at day 25, despite receiving a 16.8 and 98.4% increased dose of PTX and Dox respectively.

Combined, these results corroborate the in vitro efficacy results and highlight the effectiveness of MB delivered chemo-sonodynamic therapy as a targeted treatment for breast cancer. In addition to the improved efficacy offered by this approach, the treatment was also well tolerated with the body weight of animals in the MB treated groups mapping closely to that of untreated animals. In contrast, there was a 12.1% drop in body-weight for animals treated with free PTX/Dox over the course of the experiment. This reduction in body weight most likely results from toxicity exhibited by the free drugs or the Cremophor EL vehicle required to deliver PTX. Cremophor EL is known to produce undesirable side-effects and while poorly tolerated, is necessary to enable the dispersion of hydrophobic PTX in aqueous solution. Therefore, the ability to avoid the necessity of such a toxic vehicle by incorporating PTX within the MB shell is an added advantage.

EXAMPLE 7

Preparation of Biotin-Doxorubicin-Rose Bengal Conjugate

A tri-podal Biotin-Doxorubicin-Rose Bengal conjugate (Biotin-Dox-RB) was synthesised according to Scheme 4:

Scheme 4: Synthetic scheme for the preparation of Biotin-Dox-RB

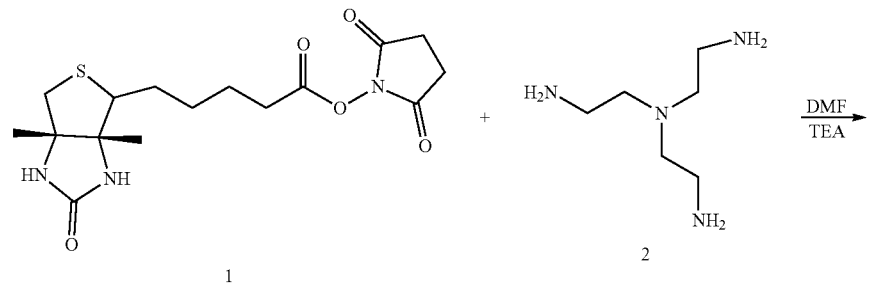

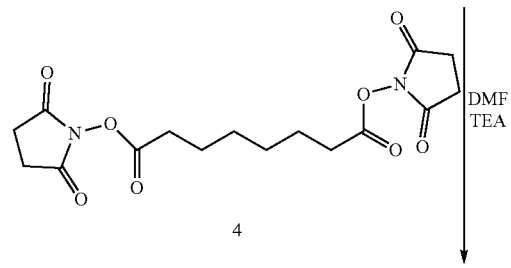

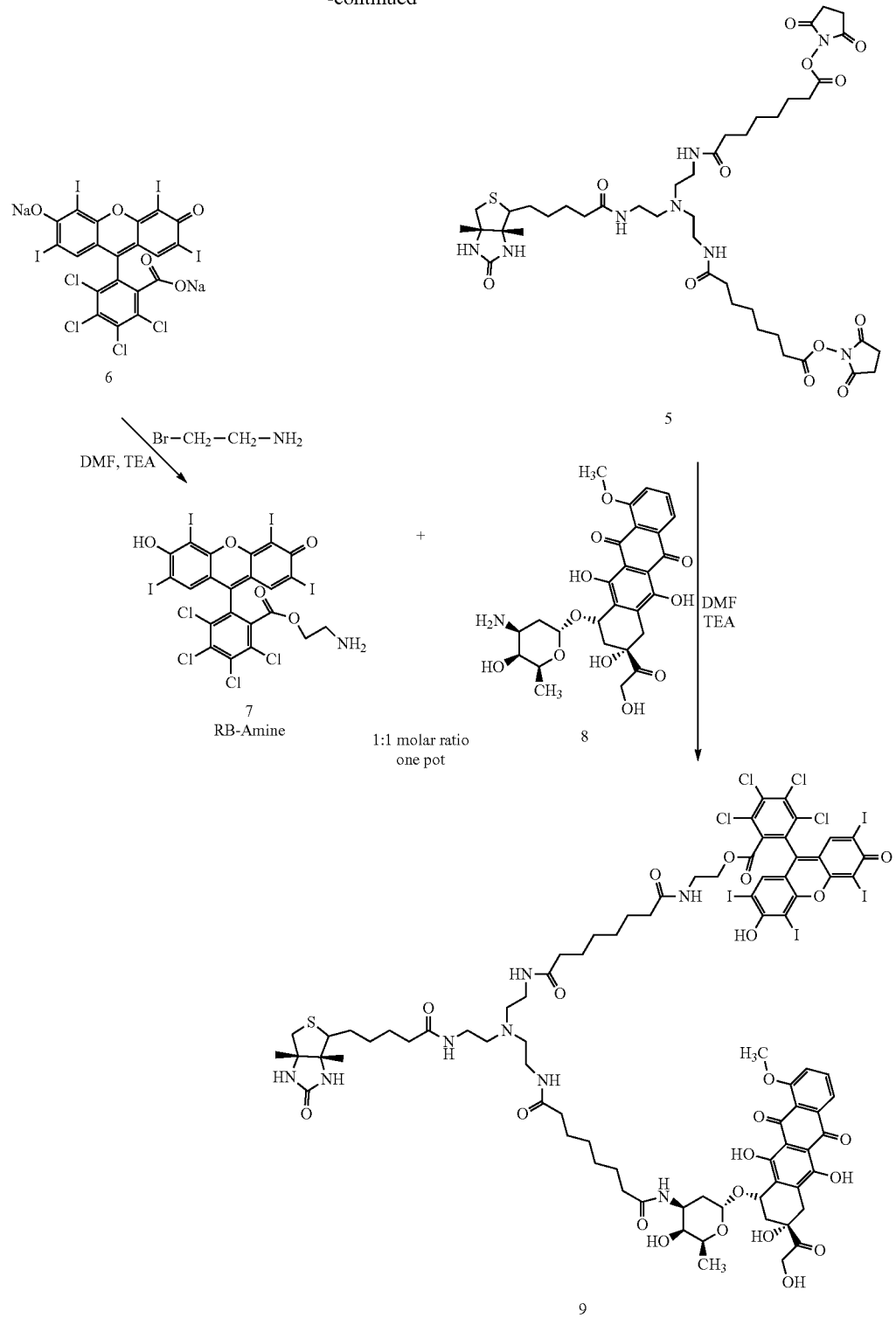

7.1 Synthesis of N-(2-(bis(2-aminoethyl)amino)ethyl)-5-(2-oxohexahydro-1H-thieno[3,4-d]imidazol-4-yl)pentanamide (3)

To a stirred solution of Biotin-NHS (0.5 g, 1.5 mmol) and TEA (catalytic amount) in anhydrous DMF (10 mL), a solution of tris(2-aminoethyl)amine (0.22 g, 1.5 mmol) in 5 mL of DMF was added. The reaction mixture was stirred at 0° C. under argon atmosphere. After 2 hr of stirring, another volume of TEA (catalytic amount) was added and the reaction mixture was allowed to stir overnight at room temperature. After completion of the reaction (by TLC), the excess DMF was removed under reduced pressure keeping the temperature below 45° C. and the white gummy liquid thus obtained was poured into excess diethyl ether (200 mL) and filtered. The crude product was purified by column chromatography on basic (TEA) silica gel (MeOH:DCM 1:9 to 3:7) to give 3 (0.33 g, 61% yield) as a white semi solid.

$^1$H NMR (DMSO-d$_6$): δ7.94 (brs, 1H, NH), 6.42 (brs, 1H, NH), 6.35 (brs, 1H, NH), 4.49 (brs, 4H, NH$_2$ X 2), 4.29 (s, 1H, CH), 4.12 (s, 1H, CH), 3.07-3.02 (m, 6H, CH$_2$ X 3), 2.88-2.82 (m, 1H, CH), 2.44-2.06 (m, 10H, CH$_2$ X 5), 1.59-1.48 (m, 4H, CH$_2$ X 2), 1.47-1.29 (m, 2H, CH$_2$). ESI-MS: cald for C$_{16}$H$_{32}$N$_6$O$_2$S, 372.23; found 373.31 (M+H).

7.2 Synthesis of bis(2,5-dioxopyrrolidin-1-yl) 8,8'-(((((2-(5-(2-oxohexahydro-1H-thieno[3,4-d]imidazol-4-yl)pentanamido)ethyl)azanediyl)bis(ethane-2,1-diyl))bis(azanediyl))bis(8-oxooctanoate) (5)

Compound 3 (0.5 g, 1.3 mmol) was dissolved in 10 mL anhydrous DMF in the presence of TEA (catalytic amount) and bis(2,5-dioxopyrrolidin-1-yl) octanedioate (4, 1 g, 2.7 mmol) was added to it. The reaction mixture was stirred at room temperature for 24 hrs under argon atmosphere. After completion of the reaction (by TLC), excess diethyl ether (200 mL) was added to the reaction mixture. The white precipitate thus obtained was filtered and washed three times with cold diethyl ether (50 mL×3). The crude product was purified by column chromatography on basic (TEA) silica gel (MeOH:CHCl$_3$ 2:8 to 5:5 v/v) to give 5 (0.83 g, 71% yield) as a low melting white solid.

$^1$H NMR (DMSO-d$_6$): δ7.94 (brs, 2H, NH X 2), 7.67 (brs, 1H, NH), 6.41 (brs, 1H, NH), 6.34 (brs, 1H, NH), 4.29 (s, 1H, CH), 4.12 (s, 1H, CH), 3.06-3.04 (m, 3H, CH and CH$_2$), 2.88-2.72 (m, 6H, CH$_2$ X 3), 2.71-2.63 (m, 8H, CH$_2$ X 4), 2.45-2.34 (m, 6H, CH$_2$ X 3), 2.20-2.06 (m, 10H, CH$_2$ X 5), 1.60-1.21 (m, 22H, CH$_2$ X 11). $^{13}$C NMR (DMSO-d$_6$): 172.5 (C=O), 170.7 (C=O), 163.1 (C=O), 162.7 (C=O), 61.4 (CH), 59.6 (CH), 55.8 (CH$_2$), 53.9 (NCH$_2$), 39.9 (CH$_2$), 39.8 (CH$_2$), 39.6 (CH$_2$), 37.3 (CH$_2$), 36.2 (CH$_2$), 35.6 (CH$_2$), 31.2 (CH$_2$), 28.7 (CH$_2$), 28.5 (CH$_2$), 25.8 (CH$_2$), 25.7 (CH$_2$), 25.6 (CH$_2$). ESI-MS: cald for C$_{40}$H$_{62}$N$_8$O$_{12}$S, 878.4; found 901.3 (M+Na salt).

7.3 Synthesis of 26-(((2S,3S,4S,6R)-3-hydroxy-2-methyl-6-(((1S,3S)-3,5,12-trihydroxy-3-(2-hydroxyacetyl)-10-methoxy-6,11-dioxo-1,2,3,4,6,11-hexahydrotetracen-1-yl)oxy)tetrahydro-2H-pyran-4-yl) amino)-4,11,19,26-tetraoxo-15-(2-(5-(2-oxohexahydro-1H-thieno[3,4-d]imidazol-4-yl)pentanamido)ethyl)-3,12,15,18-tetraazahexacosyl 2,3,4,5-tetrachloro-6-(6-hydroxy-2,4,5,7-tetraiodo-3-oxo-3H-xanthen-9-yl)benzoate (9)

To a DMF (anhydrous, 10 mL) solution of 5 (0.4 g, 0.45 mmol) Doxorubicin-hydrochloride (8, 0.26 g, 0.45 mmol) and TEA (0.5 mL) were added at 0° C. and stirred for 24 hrs at room temperature under argon atmosphere. After completion of the reaction (monitored by GC-MS), Rose Bengal amine 7 (prepared separately according to literature procedure), 0.46 g, 0.45 mmol} in DMF (5 mL) and TEA (0.5 mL) were added to the reaction mixture and continued to stir for 24 hrs. The progress of the reaction was monitored by GC-MS analysis of the crude reaction mixture. After completion of reaction, excess diethyl ether (200 mL) was added to the solution and stirred for 30 min. The dark red precipitate thus obtained was filtered and washes several times with cold diethyl ether (100 mL), ethyl acetate (100 mL), acetone-water mixture (10%, v/v, 100 mL) and finally with ethyl acetate-hexane mixture (50%, v/v, 100 ml) respectively to afford a red powder of compound 9 (0.28 g, 28% yield).

$^1$H NMR (DMSO-d$_6$):7.93 (s, 2H, Ar—CH), 7.90-7.85 (m, 2H, Ar—CH), 7.66 (brs, 5H, NH), 7.45 (s, 1H, 6.39 (brs, 1H, NH), 6.33 (brs, 1H, NH), 5.41-5.39 (m, 1H, CH), 5.19-5.18 (m, 4H, —CH$_2$ X 2), 4.93-4.71 (m, 3H, CH X 3), 4.55 (s, 3H, —OCH$_3$), 4.27-3.90 (m, 4H, CH X 4), 3.04-2.97 (m, 8H, CH$_2$ X 4), 2.80-2.77 (m, 2H, CH$_2$), 2.48-2.43 (m, 8H, CH$_2$ X 4), 2.03 (brs, 12H, CH$_2$ X 6), 1.43 (brs, 12H, CH$_2$ X 6), 1.14-1.11 (m, 13H, CH$_2$ X 5, CH$_3$ X 1). $^{13}$C NMR (DMSO-d$_6$): 220.1, 177.3, 172.5, 172.2, 171.5, 168.9, 163.2, 162.7, 157.3, 156.6, 154.6, 153.7, 150.3, 138.5, 136.5, 135.6, 133.0, 110.7, 101.9, 97.6, 96.3, 89.2, 79.3, 76.7, 66.8, 63.5, 61.4, 60.5, 59.6, 57.5, 55.8, 53.9, 51.9, 40.4, 40.2, 37.4, 36.5, 36.2, 35.6, 31.2, 28.7, 28.4, 28.3, 25.7. ESI-MS: cald for C$_{81}$H$_{90}$Cl$_4$I$_4$N$_8$O$_{22}$S, 2209.12; found 2208.02 (M–H).

EXAMPLE 8

Alternative Method for the Synthesis of Biotin-Gemcitabine-Rose Bengal Conjugate A Biotin-Gemcitabine-Rose Bengal (Biotin-Gem-RB) conjugate was synthesised according to Scheme 5:

Scheme 5: Synthetic scheme for the Preparation of Biotin-Gem-RB

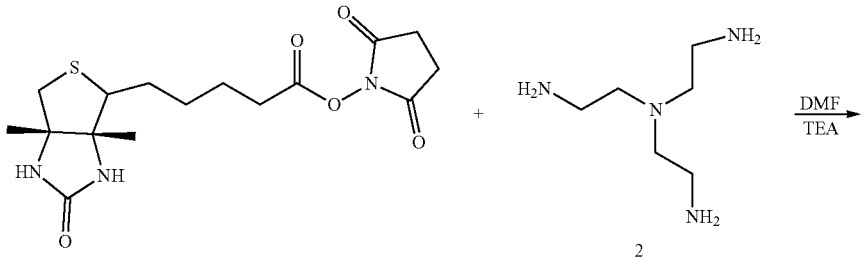

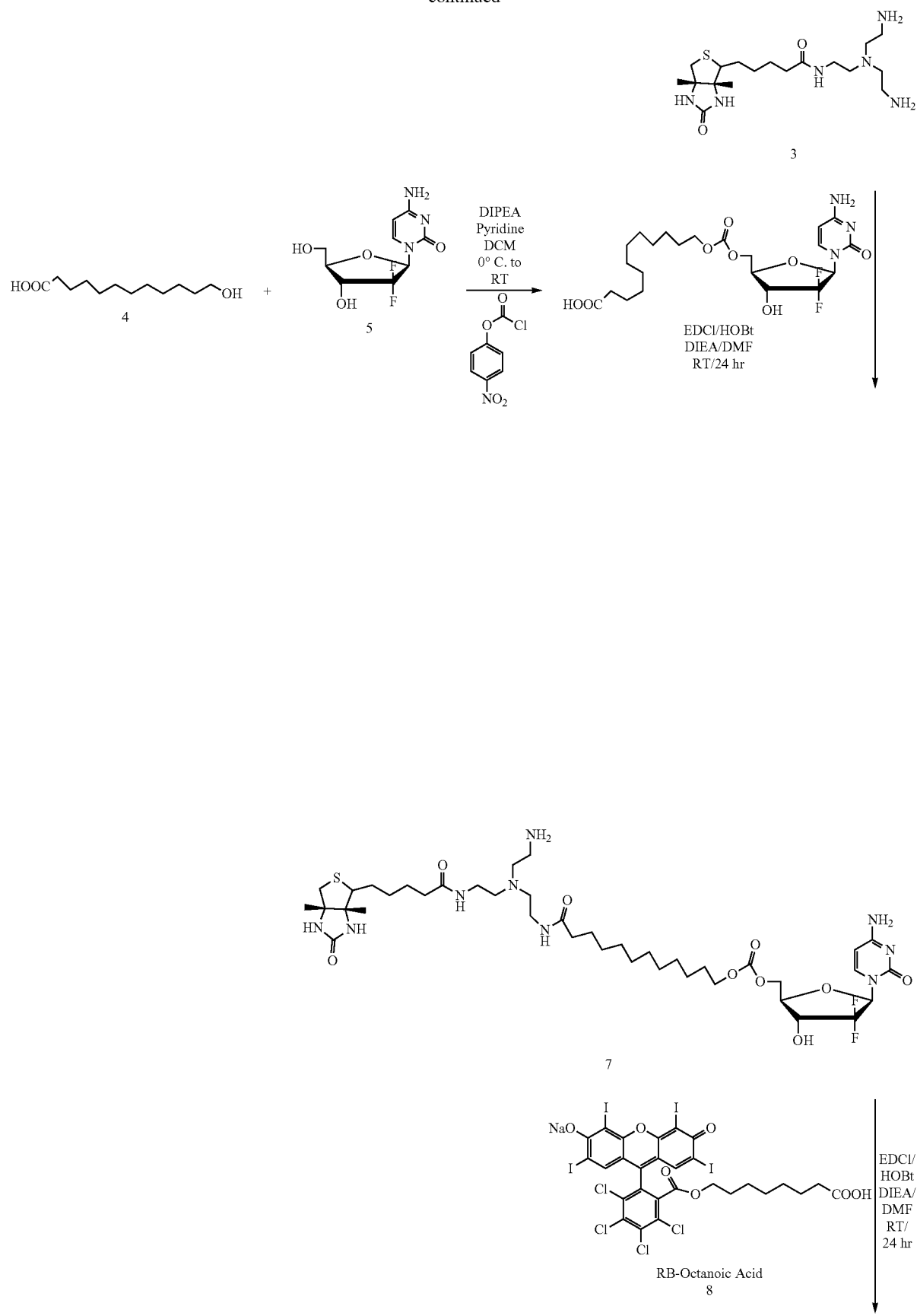

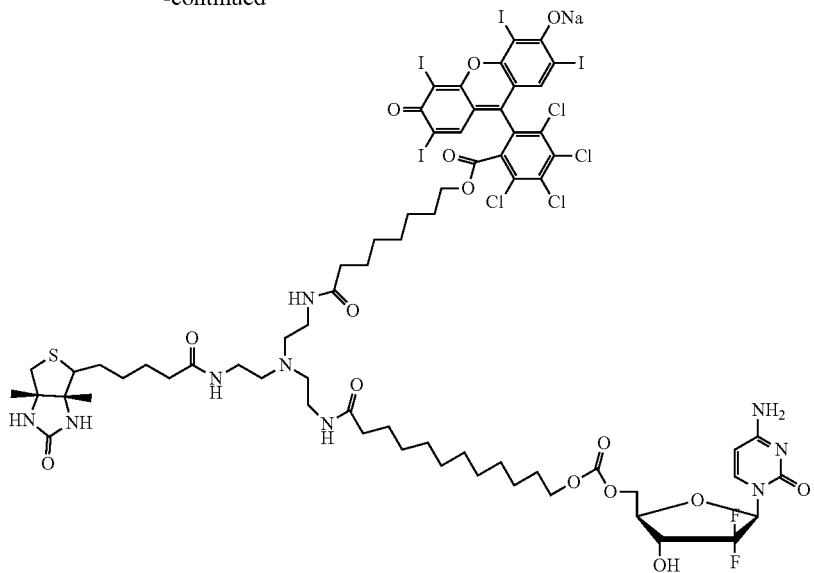

9

8.1 Synthesis of N-(2-(bis(2-aminoethyl)amino) ethyl)-5-(2-oxohexahydro-1H-thieno[3,4-d]imidazol-4-yl)pentanamide (3)

Compound 3 was synthesized according to the procedure described in Example 1.

8.2 Synthesis of 7-(((((2R,3R,5R)-5-(4-amino-2-oxopyrimidin-1(2H)-yl)-4,4-difluoro-3-hydroxytetrahydrofuran-2-yl)methoxy)carbonyl)oxy)heptanoic acid (6)

To a DCM (10 mL) solution of 4 (1 g, 4.6 mmol), 4-nitrophenyl chloroformate (2.79 g, 13.8 mmol), DIPEA (2.38 g, 18.4 mmol) and a catalytic amount of pyridine were added at 0° C. and stirred for 5 h at room temperature. Then the reaction mixture was concentrated in vacuo. The crude residue was dissolved in DMF (10 mL). To this solution, GMC hydrochloride (4.1 g, 13.8 mmol) in DMF (5 mL) and TEA (2 mL) were added and continued to stir for 24 h. The progress of the reaction was monitored by GC-MS analysis of the crude reaction mixture. After completion of reaction, excess diethyl ether (200 mL) was added to the reaction mixture. The yellowish oil thus obtained was separated and purified by flash chromatography using MeOH/CHCl$_3$ (5%, v/v) as eluent. Compound 6 was isolated as a sticky yellow liquid. (1.5 g, Yield=64.3%).

$^1$H NMR (DMSO-d$_6$): δ10.5 (brs, 1H, —COOH), 7.63 (d, J=7.5 Hz, 1H, —CH), 7.41 (brs, 2H, —NH$_2$), 6.20 (d, J=7.5 Hz, 1H, —CH), 5.18 (brs, 1H, —CH), 3.71-3.55 (m, 5H, —CH$_2$X2, —CHX1), 2.36 (brs, 2H, —CH$_2$), 1.23-1.17 (m, 18H, —CH$_2$ X 9).

$^{13}$C NMR (DMSO-d$_6$): 172.1, 166.0, 155.1, 154.9, 153.6, 123.5, 95.2, 95.0, 80.8, 69.1, 68.8, 33.6, 29.4, 29.3, 29.2, 28.9, 28.8, 25.5, 25.4.

ESI-MS: cald for C$_{22}$H$_{33}$F$_2$N$_3$O$_8$, 504.2; found 527.0 (M+Na salt).

8.3 Synthesis of 1-((2R,3R,5R)-5-(4-amino-2-oxopyrimidin-1(2H)-yl)-4,4-difluoro-3-hydroxytetrahydrofuran-2-yl)-3,16,24-trioxo-20-(2-(5-(2-oxohexahydro-1H-thieno[3,4-d]imidazol-4-yl) pentanamido)ethyl)-2,4-dioxa-17,20,23-triazahentriacontan-31-yl 2,3,4,5-tetrachloro-6-(6-hydroxy-2,4,5,7-tetraiodo-3-oxo-3H-xanthen-9-yl) benzoate (9)

EDCl, HCl (0.4 g, 2.0 mmol), and DIPEA (0.45 g, 3.5 mmol) were added to a solution of the acid 6 (0.34 g, 0.6 mmol), compound 3 (0.25 g, 0.6 mmol) and HOBt (0.27 g, 2.0 mmol) in anhydrous DMF (50 mL) and stirred for 24 hrs at room temperature under nitrogen. The progress of the reaction was monitored by GC-MS analysis of the crude reaction mixture. After completion of reaction, RB-Octanoic Acid, 8 (prepared according to the literature procedure, 0.8 g, 0.7 mmol) in 5 mL of DMF was added to the reaction mixture followed by a catalytic amount of DIPEA and continued to stir for 24 h at room temperature. After completion of reaction, excess diethyl ether (200 mL) was added to the reaction mixture and stirred for 30 min. The pink red precipitate thus obtained was filtered and was washed several times with cold diethyl ether (100 mL), ethyl acetate (100 mL), acetone-water mixture (10%, v/v, 100 mL) and finally with ethyl acetate-hexane mixture (50%, v/v, 100 ml) respectively to afford a pink red powder of compound 9 (0.63 g, 45% yield).

$^1$H NMR (DMSO-d$_6$): δ7.86 (s, 2H, Ar—CH), 7.73 (d, J=7.0 Hz, 1H, CH), 7.39 (brs, 3H, NH X 3), 6.40-6.34 (m, 2H, NH X2), 6.03 (s, 1H, CH), 5.72 (d, J=7.0 Hz, 1H, CH), 4.22 (s, 1H, CH), 4.05 (brs, 3H, CH$_2$, CH X2), 3.86 (brs, 1H, OH), 3.81-3.50 (m, 6H, CH X 2, CH$_2$ X 2), 3.02-2.86 (m, 8H, CH$_2$ X 4), 2.80-2.00 (m, 12H, CH$_2$ X 6), 1.52-0.81 (m, 32H, CH$_2$ X 16).

$^{13}$C NMR (DMSO-d$_6$): 172.6, 171.6, 169.9, 168.9, 166.0, 163.2, 162.7, 155.1, 141.5, 141.1, 123.5, 98.9, 96.4, 95.0, 83.9, 80.8, 70.2, 69.1, 68.9, 68.7, 61.4, 59.6, 59.2, 54.2, 54.0, 48.9, 46.0, 38.0, 37.3, 36.1, 35.5, 31.1, 28.9, 28.6, 28.3, 25.7.

ESI-MS: cald for $C_{66}H_{79}Cl_4F_2I_4N_9O_{15}S$, 1955.03; found 1956.5 (M+H).

The invention claimed is:

1. A microbubble complex which comprises a microbubble attached to a plurality of linking groups, each linking group having three branches wherein a first branch of the linking group is bound to the microbubble, a second branch of the linking group is linked to a chemotherapeutic agent and a third branch of the linking group is linked to a sonosensitising agent, wherein said chemotherapeutic agent is an anti-metabolite or an anthracycline, and said sonosensitising agent is selected from the group consisting of phenothiazine dyes, Rose Bengal, porphyrins, chlorins, benzochlorins, phthalocyanines, napthalocyanines, porphycenes, cyanines, azodipyromethines, acridine dyes, purpurins, pheophorbides, verdins, psoralens, hematoporphyrins, protoporphyrins and curcumins.

2. A complex as claimed in claim 1, wherein each linking group is bound to the microbubble via a non-covalent linkage.

3. A complex as claimed in claim 1, wherein each linking group is bound to the sonosensitising agent and to the chemotherapeutic agent via covalent bonds.

4. A complex as claimed in claim 1, wherein each linking group comprises an organic group comprising a chain of up to about 200 atoms.

5. A complex as claimed in claim 1, wherein each linking group comprises a branched $C_{30-50}$ alkylene chain optionally substituted by one or more groups selected from $C_{1-3}$ alkyl, —O($C_{1-3}$)alkyl, and —OR' (where R' is H or $C_{1-6}$ alkyl); and in which one or more —$CH_2$— groups of the alkylene chain may be replaced by a group independently selected from —O—, —CO—, —C(O)O—, —NR"— and —NR"CO— (where each R" is independently H or $C_{1-6}$ alkyl).

6. A complex as claimed in claim 1, wherein each linking group is terminally substituted by biotin or a biotin residue.

7. A complex as claimed in claim 1, wherein each linking group has the following structure:

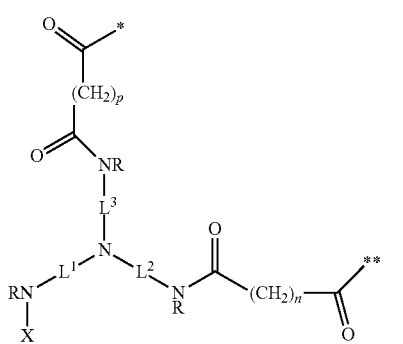

(I)

wherein:
$L^1$, $L^2$ and $L^3$ are each independently —($CH_2$)q- in which q is an integer from 1 to 4;
each R is independently either H or $C_{1-6}$ alkyl;
n is an integer from 2 to 10;
p is an integer from 2 to 10;
X is a functional group capable of binding to a microbubble or to a 'functionalised' microbubble;
* denotes the point of attachment of the linking group to a sonosensitising agent, a 'functionalised' sonosensitising agent, or a residue of a sonosensitising agent; and
** denotes the point of attachment of the linking group to a chemotherapeutic agent, a 'functionalised' chemotherapeutic agent, or a residue of a chemotherapeutic agent.

8. A complex as claimed in claim 1, wherein each linking group has the following structure:

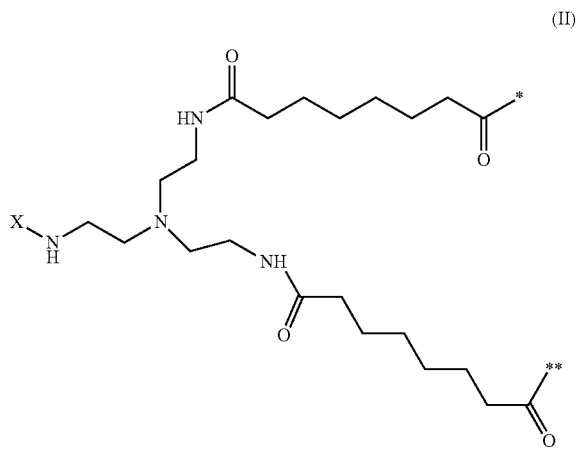

(II)

wherein:
X is a functional group capable of binding to a microbubble or to a 'functionalised' microbubble;
* denotes the point of attachment of the linking group to a sonosensitising agent, a 'functionalised' sonosensitising agent, or a residue of a sonosensitising agent; and
** denotes the point of attachment of the linking group to a chemotherapeutic agent, a 'functionalised' chemotherapeutic agent, or a residue of a chemotherapeutic agent.

9. A complex as claimed in claim 1, wherein each linking group has the following structure:

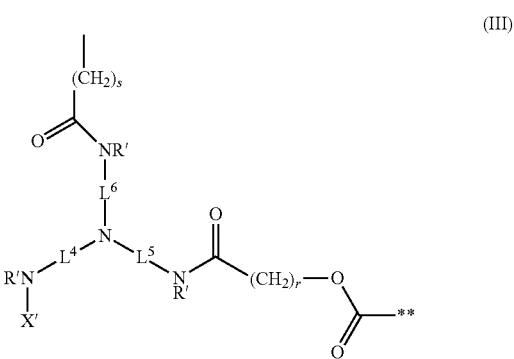

(III)

wherein:
$L^4$, $L^5$ and $L^6$ are each independently —($CH_2$)t— in which t is an integer from 1 to 4;
each R' is independently either H or $C_{1-6}$ alkyl;
r is an integer from 2 to 10;
s is an integer from 2 to 10;
X' is a functional group capable of binding to a microbubble or to a 'functionalised' microbubble;
* denotes the point of attachment of the linking group to a sonosensitising agent, a 'functionalised' sonosensitising agent, or a residue of a sonosensitising agent; and

** denotes the point of attachment of the linking group to a chemotherapeutic agent, a 'functionalised' chemotherapeutic agent, or a residue of a chemotherapeutic agent.

10. A complex as claimed in claim 1, wherein each linking group has the following structure:

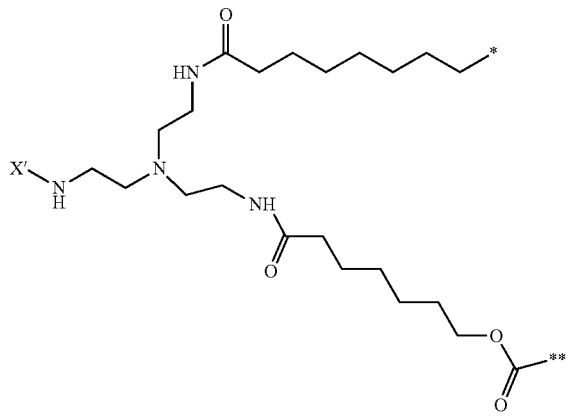

(IV)

wherein:

X' is a functional group capable of binding to a microbubble or to a 'functionalised' microbubble;

* denotes the point of attachment of the linking group to a sonosensitising agent, a 'functionalised' sonosensitising agent, or a residue of a sonosensitising agent; and

** denotes the point of attachment of the linking group to a chemotherapeutic agent, a 'functionalised' chemotherapeutic agent, or a residue of a chemotherapeutic agent.

11. A complex as claimed in claim 1, wherein each linking group has the following structure:

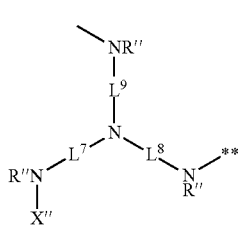

(V)

wherein:

$L^7$, $L^8$ and $L^9$ are each independently —$(CH_2)_u$— in which u is an integer from 1 to 4;

each R" is independently either H or $C_{1-6}$ alkyl;

X" is a functional group capable of binding to a microbubble or to a 'functionalised' microbubble;

* denotes the point of attachment of the linking group to a sonosensitising agent, a 'functionalised' sonosensitising agent, or a residue of a sonosensitising agent; and

** denotes the point of attachment of the linking group to a chemotherapeutic agent, a 'functionalised' chemotherapeutic agent, or a residue of a chemotherapeutic agent.

12. A complex as claimed in claim 1, wherein each linking group has the following structure:

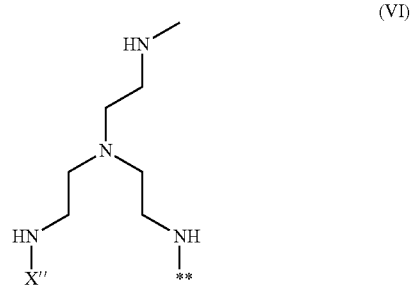

(VI)

wherein:

X" is a functional group capable of binding to a microbubble or to a 'functionalised' microbubble;

* denotes the point of attachment of the linking group to a sonosensitising agent, a 'functionalised' sonosensitising agent, or a residue of a sonosensitising agent; and

** denotes the point of attachment of the linking group to a chemotherapeutic agent, a 'functionalised' chemotherapeutic agent, or a residue of a chemotherapeutic agent.

13. A complex as claimed in claim 1, wherein the microbubble comprises a shell having incorporated therein one or more additional chemotherapeutic agents.

14. A complex as claimed in claim 13, wherein said one or more additional chemotherapeutic agents are selected from the following: antifolates; 5-fluoropyrimidines; cytidine analogues; purine antimetabolites; alkylating agents; non-classical alkylating agents; platinum analogues; antitumour antibiotics; bioreductive drugs; anthracyclines; topoisomerase I inhibitors; topoisomease II inhibitors; antimicrotubule agents such as vinca alkaloids, taxols, and epothilones; antioestrogens; antiandrogens; aromatase inhibitors; antiangiogenic or hypoxia targeting drugs; antivascular agents; tyrosine kinase inhibitors; oncogene or signalling pathway targeting agents; agents targeting stress proteins; autophagy targeting agents; proteasome targeting agents; telomerase inhibitors; histone deacetylase inhibitors; DNA methyl transferase inhibitors; alkyl sulfonates; aziridines; ethylenimines and methylamelamines; nitrogen mustards; nitrosureas; purine analogues; pyrimidine analogues; androgens; anti-adrenals, and immune checkpoint inhibitors; and pharmaceutically acceptable salts, derivatives or analogues of any of these compounds or anti-metabolites.

15. A complex as claimed in claim 13, wherein said additional chemotherapeutic agent is an anti-microtubule agent.

16. A complex as claimed in claim 1, wherein the microbubble comprises a shell which retains a gas.

17. A complex as claimed in claim 1 which comprises a microbubble having a diameter in the range of from 0.1 to 100 μm.

18. A complex as claimed in claim 1, wherein the microbubble has a shell comprising one or more phospholipids, each optionally linked to one or more polymers.

19. A complex as claimed in claim 1, wherein the microbubble is biotinylated and, optionally, further avidin-functionalised.

20. A complex as claimed in claim 1, wherein the sonosensitising agent is Rose Bengal, methylene blue, indocyanine green, or an analogue thereof.

21. A complex as claimed in claim 1, wherein the microbubble is linked to one or more structures selected from: formula (9) as shown in Scheme 2 (Biotin-Gem-RB), formula (9) as shown in Scheme 4 (Biotin-Dox-RB), and formula (9) as shown in Scheme 5 (Biotin-Gem-RB).

* * * * *